(12) United States Patent
Chen et al.

(10) Patent No.: US 7,838,498 B2
(45) Date of Patent: Nov. 23, 2010

(54) BENZYLIC GLYCOSIDE DERIVATIVES AND METHODS OF USE

(75) Inventors: Yuanwei Chen, North Haven, CT (US); Yan Feng, Shanghai (CN); Baihua Xu, Shanghai (CN); Binhua Lv, Shanghai (CN); Brian Seed, Derry, NH (US); Michael J. Hadd, San Diego, CA (US); Huawei Cheng, Shanghai (CN); Zelin Sheng, Belle Mead, NJ (US); Min Xu, Shanghai (CN); Congna Wang, Shanghai (CN); Jiyan Du, Shanghai (CN); Lili Zhang, Shanghai (CN); Ge Xu, Shanghai (CN); Yuelin Wu, Shanghai (CN)

(73) Assignee: Theracos, Inc., Sunnyvale, CA (US)

( * ) Notice: Subject to any disclaimer, the term of this patent is extended or adjusted under 35 U.S.C. 154(b) by 304 days.

(21) Appl. No.: 12/060,767

(22) Filed: Apr. 1, 2008

(65) Prior Publication Data

US 2008/0242596 A1    Oct. 2, 2008

Related U.S. Application Data

(60) Provisional application No. 60/909,672, filed on Apr. 2, 2007.

(51) Int. Cl.
*A01N 43/04* (2006.01)
*A61K 31/70* (2006.01)
*C07H 1/00* (2006.01)

(52) U.S. Cl. .................................. 514/23; 536/1.11
(58) Field of Classification Search .................. None
See application file for complete search history.

(56) References Cited

U.S. PATENT DOCUMENTS

| | | | |
|---|---|---|---|
| 6,414,126 B1 | 7/2002 | Ellsworth et al. | |
| 6,683,056 B2 | 1/2004 | Washburn et al. | |
| 6,936,590 B2 | 8/2005 | Washburn et al. | |
| 7,022,725 B2 | 4/2006 | Momose et al. | |
| 7,094,763 B2 | 8/2006 | Rybczynski et al. | |
| 2005/0014704 A1 | 1/2005 | Frick et al. | |
| 2005/0187168 A1 | 8/2005 | Eickelmann et al. | |
| 2005/0209166 A1 | 9/2005 | Eckhardt et al. | |
| 2005/0209309 A1 | 9/2005 | Sato et al. | |
| 2005/0233988 A1 | 10/2005 | Nomura et al. | |
| 2006/0122126 A1 | 6/2006 | Imamura et al. | |
| 2006/0166899 A1 | 7/2006 | Teranishi et al. | |
| 2006/0234954 A1 | 10/2006 | Urbanski | |
| 2006/0247179 A1 | 11/2006 | Fushimi et al. | |

FOREIGN PATENT DOCUMENTS

| | | |
|---|---|---|
| WO | WO 98/31897 A1 | 7/1998 |
| WO | WO 2005/085237 A1 | 9/2005 |
| WO | WO 2006/011469 A1 | 2/2006 |
| WO | WO 2006/073197 A1 | 7/2006 |
| WO | WO 2006/108842 A1 | 10/2006 |

OTHER PUBLICATIONS

Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
Blazejewski, J-C. et al., "2-Trifluoromethoxyethyl Triflate: A Versatile Trifluoromethoxyethyl Carrier," *Journal of Organic Chemistry*, 2001, vol. 66, pp. 1061-1063.
International Search Report mailed on Jun. 26, 2008, for PCT Application No. PCT/US08/59047 filed on Apr. 1, 2008, 2 pages.

\* cited by examiner

*Primary Examiner*—Traviss C McIntosh, III
(74) *Attorney, Agent, or Firm*—Townsend and Townsend and Crew LLP

(57) ABSTRACT

Provided are compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

37 Claims, 15 Drawing Sheets

R = F, Cl, Br, CF$_3$, CHF$_2$, alkenyl, alkynyl
A = O, S, NH, SO, SO$_2$, methylene, difluoromethylene
Halo = Cl, Br, I
n = 1-6

R = F, Cl, Br, CF$_3$, CHF$_2$, alkenyl, alkynyl
A = O, S, NH, SO, SO$_2$, methylene, difluoromethylene
Halo = Cl, Br, I
n = 1-6

R = Alkenyloxyalkoxy, alkynyloxyalkoxy, alkenyloxyalkyl, alkynyloxyalkyl
A = O, S, NH, SO, $SO_2$, methylene, difluoromethylene
Halo, $Halo^1$ = F, Cl, Br, I R = H, alkyl
Y = H, alkyl, alkenyl, alkynyl, alkyloxyalkyl, alkenyloxyalkyl, alkynyloxyalkyl
A = O, S, NH, SO, $SO_2$, methylene, difluoromethylene
Halo = Cl, Br, I
n = 0-5

US 7,838,498 B2

BENZYLIC GLYCOSIDE DERIVATIVES AND METHODS OF USE

CROSS-REFERENCE TO RELATED APPLICATION

This application claims the benefit of U.S. Provisional Application Ser. No. 60/909,672 filed Apr. 2, 2007, the disclosure of which is incorporated herein by reference.

STATEMENT AS TO RIGHTS TO INVENTIONS MADE UNDER FEDERALLY SPONSORED RESEARCH AND DEVELOPMENT

NOT APPLICABLE

BACKGROUND OF THE INVENTION

According to the World Health Organization, approximately 150 million people worldwide have diabetes mellitus. The two principal forms of diabetes are type 1 diabetes, in which the pancreas fails to produce insulin, and type 2 diabetes, in which the body fails to respond properly to the insulin produced (insulin resistance). Accounting for about 90% of all diabetes cases, type 2 diabetes is by far the most common. In both types of diabetes, the absence of insulin action or proper response to insulin results in elevated levels of serum glucose (hyperglycemia). Serious complications associated with diabetes include retinopathy (leading to visual impairment or blindness), cardiovascular disease, nephropathy, neuropathy, ulcers and diabetic foot disease.

Individuals with type 1 diabetes currently require insulin therapy. While in many cases type 2 diabetes can be managed with diet and exercise, drug intervention also frequently is required. Besides insulin, which is needed by about one-third of patients with type 2 diabetes, current antidiabetic therapies include biguanides (which decrease glucose production in the liver and increase sensitivity to insulin), sulfonylureas and meglitinides (which stimulate insulin production), alpha-glucosidase inhibitors (which slow starch absorption and glucose production), and thiazolidinediones (which increase insulin sensitivity). These medicines are often used in combination, and even then may not provide adequate glycemic control or may produce undesired side effects. Such side effects include lactic acidosis (biguanides), hypoglycemia (sulfonylureas), and edema and weight gain (thiazolidinediones). Therefore, new antidiabetic agents providing improved glycemic control and lacking these adverse effects are highly desired.

One promising target for therapeutic intervention in diabetes and related disorders is the glucose transport system of the kidneys. Cellular glucose transport is conducted by either facilitative ("passive") glucose transporters (GLUTs) or sodium-dependent ("active") glucose cotransporters (SGLTs). SGLT1 is found predominantly in the intestinal brush border, while SGLT2 is localized in the renal proximal tubule and is reportedly responsible for the majority of glucose reuptake by the kidneys. Recent studies suggest that inhibition of renal SGLT may be a useful approach to treating hyperglycemia by increasing the amount of glucose excreted in the urine (Arakawa K, et al., Br J Pharmacol 132:578-86, 2001; Oku A, et al., Diabetes 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer R, et al., J Am Soc Nephrol 14:2873-82, 2003). Therefore, compounds which inhibit SGLT, particularly SGLT2, are promising candidates for use as antidiabetic drugs. Compounds previously described as useful for inhibiting SGLT include C-glycoside derivatives (such as those described in U.S. Pat. Nos. 6,414,126, 6,936,590, US20050209166, US20050233988, WO2005085237, U.S. Pat. No. 7,094,763, US20060122126 and WO2006108842), O-glycoside derivatives (such as those described in U.S. Pat. No. 6,683,056, US20050187168, US20060166899, US20060234954 and US20060247179), cyclohexane derivatives (such as those described in WO2006011469), and thio-glucopyranoside derivatives (such as those described in US20050209309 and WO2006073197).

BRIEF SUMMARY OF THE INVENTION

The present invention provides compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

DETAILED DESCRIPTION OF THE INVENTION

Definitions

Figure 1:
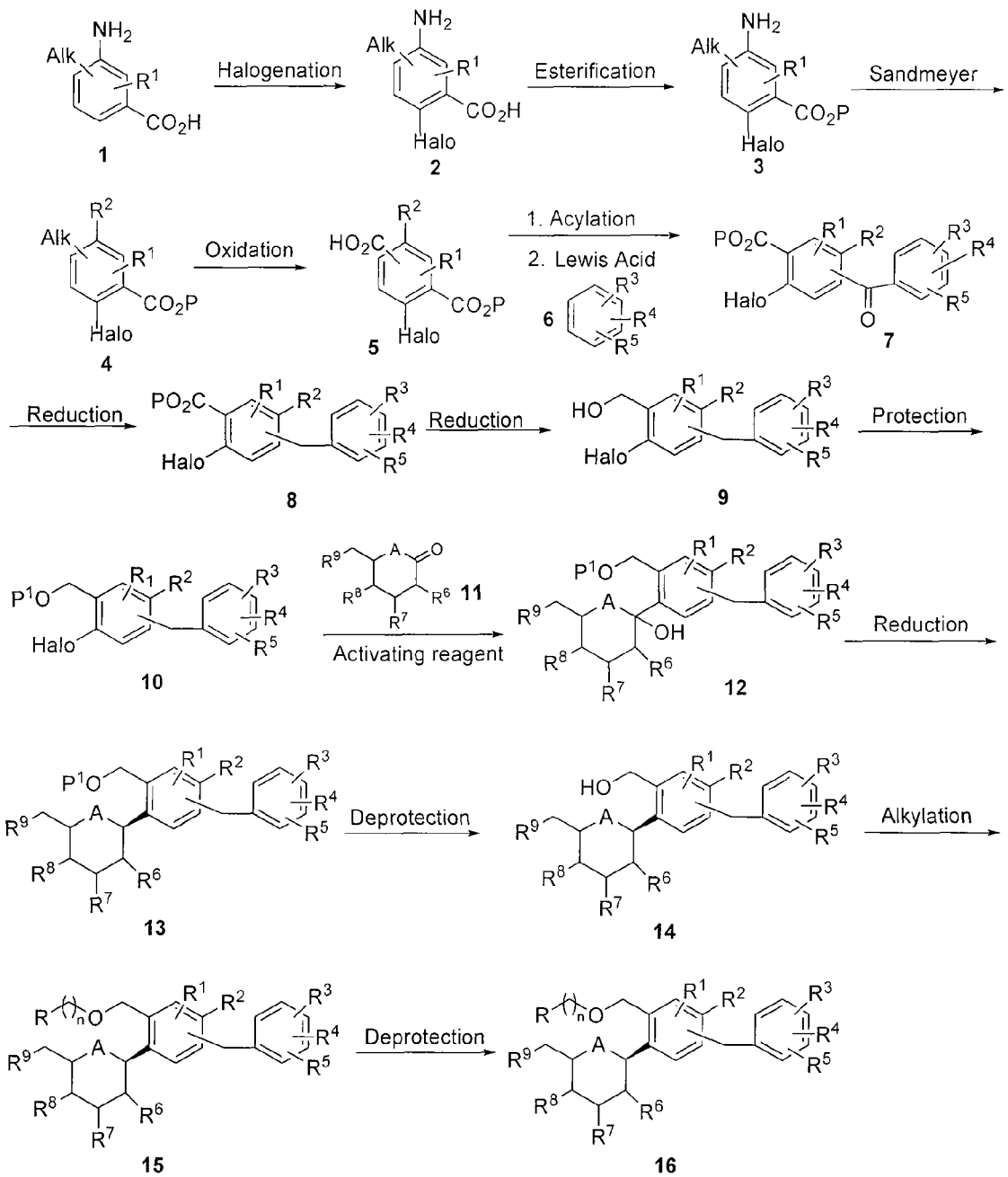
FIGS. 1-8 provide generic synthesis schemes for compounds of the invention.

As used herein, the term "halo" means a monovalent halogen radical or atom selected from fluoro, chloro, bromo and iodo. Preferred halo groups are fluoro, chloro and bromo.

As used herein, the term "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected from the group consisting of halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxy, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, unless otherwise indicated, the term "alkyl" alone or in combination refers to a monovalent saturated aliphatic hydrocarbon radical having the indicated number of carbon atoms. The radical may be a linear or branched chain and, where specified, optionally substituted with one to three suitable substituents as defined above. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional suitable substituents include halo, methoxy, ethoxy, cyano, nitro and amino.

As used herein, unless otherwise indicated, the term "alkenyl" alone or in combination refers to a monovalent aliphatic hydrocarbon radical having the indicated number of carbon atoms and at least one carbon-carbon double bond. The radical may be a linear or branched chain, in the E or Z form, and where specified, optionally substituted with one to three suitable substituents as defined above. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional suitable substituents include halo, methoxy, ethoxy, cyano, nitro and amino.

As used herein, unless otherwise indicated, the term "alkynyl" alone or in combination refers to a monovalent aliphatic hydrocarbon radical having the indicated number of carbon atoms and at least one carbon-carbon triple bond. The radical may be a linear or branched chain, and where specified, optionally substituted with one to three suitable substituents as defined above. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional suitable substituents include halo, methoxy, ethoxy, cyano, nitro and amino.

As used herein, unless otherwise indicated, the term "cycloalkyl" alone or in combination refers to a monovalent alicyclic saturated hydrocarbon radical having three or more carbons forming a carbocyclic ring, and where specified, optionally substituted with one to three suitable substituents as defined above. Illustrative examples of cycloalkyl groups include, but are not limited to, cyclopropyl, cyclobutyl, cyclopentyl, cyclohexyl, cycloheptyl, cyclooctyl, cyclononyl and the like. Preferred optional suitable substituents include halo, methyl, ethyl, methoxy, ethoxy, cyano, nitro and amino.

As used herein, unless otherwise indicated, the term "cycloalkenyl" alone or in combination refers to a monovalent alicyclic hydrocarbon radical having three or more carbons forming a carbocyclic ring and at least one carbon-carbon double bond, and where specified, optionally substituted with one to three suitable substituents as defined above. Illustrative examples of cycloalkenyl groups include, but are not limited to, cyclopentenyl, cyclohexenyl and the like. Preferred optional suitable substituents include halo, methyl, ethyl, methoxy, ethoxy, cyano, nitro and amino.

As used herein, unless otherwise indicated, the terms "alkylene", "alkenylene", "alkynylene", "cycloalkylene" and "cycloalkenylene" refer to a divalent hydrocarbon radical that is formed by removal of a hydrogen atom from an alkyl, alkenyl, alkynyl, cycloalkyl or cycloalkenyl radical, respectively, as such terms are defined above.

As used herein, unless otherwise indicated, the term "aryl" alone or in combination refers to a monovalent aromatic hydrocarbon radical having six to ten carbon atoms forming a carbocyclic ring, and where specified, optionally substituted with one to three suitable substituents as defined above. Illustrative examples of aryl groups include, but are not limited to, phenyl, naphthyl, tetrahydronaphthyl, indanyl and the like. Preferred aryl groups are phenyl and naphthyl, optionally mono- or disubstituted by identical or different suitable substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the term "heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, tetrahydropyranyl, and the like.

As used herein, unless otherwise indicated, the term "heteroaryl" alone or in combination refers to a monovalent aromatic heterocyclic radical having two to nine carbons and one to four heteroatoms selected from N, S and O forming a five- to ten-membered monocyclic or fused bicyclic ring, and where specified, optionally substituted with one to three suitable substituents as defined above. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Preferred optional suitable substitutions include one or two identical or different substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the terms "alkoxy" and "alkyloxy" alone or in combination refer to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, unless otherwise indicated, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "carbamoyl" refers to a monovalent radical of the form —C(O)NH(R), wherein R is hydrogen, $C_1$-$C_6$ alkyl, $C_2$-$C_6$ alkenyl, $C_3$-$C_6$ cycloalkyl, or aryl as such terms are defined above.

As used herein, unless otherwise indicated, the terms "di-($C_1$-$C_3$ alkyl)amino" and "di-($C_1$-$C_6$ alkyl)amino" alone or in combination refer to an amino group that is substituted with two groups independently selected from $C_1$-$C_3$ alkyl or $C_1$-$C_6$ alkyl, respectively.

As used herein, the terms "treating" and "treatment" refer to delaying the onset of, retarding or reversing the progress of, or alleviating or preventing either the disease or condition to which the term applies, or one or more symptoms of such disease or condition.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity.

As used herein, the term "compound" refers to a molecule produced by any means including, without limitation, synthesis in vitro or generation in situ or in vivo.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington. The Science and Practice of Pharmacy, 21$^{st}$ Ed., Gennaro, Ed., Lippencott Williams & Wilkins (2003). As discussed therein, immediate and nonimmediate release can be defined kinetically by reference to the following equation:

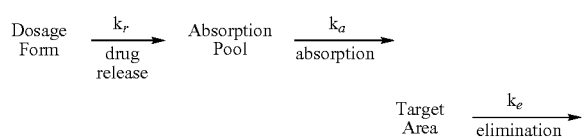

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the term "delayed release" refers to a pharmaceutical preparation that passes through the stomach intact and dissolves in the small intestine.

General

The present invention provides compounds having an inhibitory effect on sodium-dependent glucose cotransporter SGLT, preferably SGLT2. Some compounds according to the present invention also have an inhibitory effect on sodium-dependent glucose cotransporter SGLT1. Owing to their ability to inhibit SGLT, the compounds of the present invention are suitable for the treatment and/or prevention of any and all conditions and diseases that are affected by inhibition of SGLT activity, particularly SGLT2 activity. Therefore, the compounds of the present invention are suitable for the prevention and treatment of diseases and conditions, particularly metabolic disorders, including but not limited to type 1 and type 2 diabetes mellitus, hyperglycemia, diabetic complications (such as retinopathy, nephropathy [e.g., progressive renal disease], neuropathy, ulcers, micro- and macroangiopathies, and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases.

The present invention also provides pharmaceutically acceptable salts and prodrugs of compounds according to the present invention.

The present invention further provides pharmaceutical compositions comprising an effective amount of a compound or mixture of compounds according to the present invention, or a pharmaceutically acceptable salt or prodrug thereof, in a pharmaceutically acceptable carrier.

The present invention further provides synthetic intermediates and processes for preparing the compounds of the present invention.

The present invention also provides methods of using the compounds according to the present invention, independently or in combination with other therapeutic agents, for treating diseases and conditions which may be affected by SGLT inhibition.

The present invention also provides methods of using the compounds according to the present invention for the preparation of a medicament for treating diseases and conditions which may be affected by SGLT inhibition.

DETAILED EMBODIMENTS

Compounds and Preparative Methods

In one aspect, the present invention provides for compounds of Formula I:

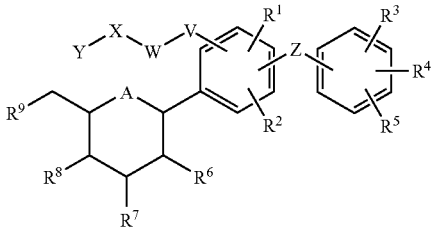

I wherein

A represents oxygen; sulfur; SO; SO$_2$; methylene optionally substituted with one to two substituents independently selected from halo, hydroxy, C$_1$-C$_6$ alkyl, C$_1$-C$_6$ alkoxy, C$_3$-C$_6$ cycloalkyl and C$_3$-C$_6$ cycloalkyloxy; C$_3$-C$_5$ 1,1-cycloalkylene optionally substituted with one to two substituents independently selected from halo, C$_1$-C$_6$ alkyl, C$_1$-C$_6$ alkoxy, C$_3$-C$_6$ cycloalkyl and C$_3$-C$_6$ cycloalkyloxy; or NR$^a$;

V represents oxygen; sulfur; SO; SO$_2$; or a single bond;

W represents C$_1$-C$_6$ alkylene, C$_2$-C$_6$ alkenylene, C$_2$-C$_6$ alkynylene, C$_3$-C$_{10}$ cycloalkylene or C$_5$-C$_{10}$ cycloalkenylene;

wherein alkylene, alkenylene, alkynylene, cycloalkylene and cycloalkenylene groups optionally may be partly or completely fluorinated and may be mono- or disubstituted by identical or different substituents selected from chlorine, hydroxy, C$_1$-C$_3$ alkyl, C$_1$-C$_3$ alkoxy, C$_3$-C$_6$ cycloalkyl, C$_3$-C$_6$ cycloalkyloxy, C$_5$-C$_{10}$ cycloalkenyl or C$_5$-C$_{10}$ cycloalkenyloxy, and in cycloalkylene and cycloalkenylene groups one or two methylene groups are optionally replaced independently of one another by O, S, CO, SO, SO$_2$ or NR$^b$, and one or two methyne groups are optionally replaced by N;

X represents oxygen; sulfur; SO; or SO$_2$;

Y represents C$_1$-C$_6$ alkyl, C$_1$-C$_6$ haloalkyl, C$_1$-C$_6$ hydroxyalkyl, C$_2$-C$_6$ alkenyl, C$_2$-C$_6$ alkynyl, C$_3$-C$_{10}$ cycloalkyl, C$_5$-C$_{10}$ cycloalkenyl, (C$_5$-C$_{10}$ cycloalkenyl)C$_1$-C$_3$ alkyl, (C$_3$-C$_{10}$ cycloalkyl)C$_2$-C$_4$ alkenyl, C$_3$-C$_6$ cycloalkylidenemethyl, (C$_5$-C$_{10}$ cycloalkenyl)C$_2$-C$_4$ alkenyl, (C$_1$-C$_4$ alkyloxy)C$_1$-C$_3$ alkyl, (C$_2$-C$_4$ alkenyloxy)C$_1$-C$_3$ alkyl, (C$_3$-C$_{10}$ cycloalkyloxy)C$_1$-C$_3$ alkyl, (C$_5$-C$_{10}$ cycloalkenyloxy)C$_1$-C$_3$ alkyl, (C$_1$-C$_4$ alkylamino)C$_1$-C$_3$ alkyl, di-(C$_1$-C$_3$ alkylamino)C$_1$-C$_3$ alkyl, (C$_1$-C$_6$ alkyl)carbonyl(C$_1$-C$_3$)alkyl, (C$_2$-C$_6$ alkenyl)carbonyl(C$_1$-C$_3$)alkyl, (C$_2$-C$_6$ alkynyl)carbonyl(C$_1$-C$_3$)alkyl, (arylcarbonyl)C$_1$-C$_3$ alkyl, (heteroarylcarbonyl)C$_1$-C$_3$ alkyl, (C$_1$-C$_6$ alkylsulfonyl)C$_1$-C$_3$ alkyl, (C$_2$-C$_6$ alkenylsulfonyl)C$_1$-C$_3$ alkyl, (C$_2$-C$_6$ alkynylsulfonyl)C$_1$-C$_3$ alkyl, (arylsulfonyl)C$_1$-C$_3$ alkyl, (heteroarylsulfonyl)C$_1$-C$_3$ alkyl, (C$_1$-C$_6$ alkyl)aminocarbonyl(C$_1$-C$_3$)alkyl, (C$_2$-C$_6$ alkenyl)aminocarbonyl(C$_1$-C$_3$)alkyl, (C$_2$-C$_6$ alkynyl)aminocarbonyl(C$_1$-C$_3$)alkyl, (arylaminocarbonyl)C$_1$-C$_3$ alkyl, (heteroarylaminocarbonyl)C$_1$-C$_3$ alkyl, (C$_1$-C$_6$ alkyl)carbonyl, (C$_2$-C$_6$ alkenyl)carbonyl, (C$_2$-C$_6$ alkynyl)carbonyl, arylcarbonyl or heteroarylcarbonyl;

wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, C$_1$-C$_3$ alkyl, C$_1$-C$_3$ alkoxy, C$_3$-C$_6$ cycloalkyl, C$_3$-C$_6$ cycloalkyloxy, C$_5$-C$_{10}$ cycloalkenyl, C$_5$-C$_{10}$ cycloalkenyloxy, and NR$^b$R$^c$, and in cycloalkyl and cycloalkenyl groups or portions one or two methylene groups are optionally replaced independently of one another by O, S, CO, SO, SO$_2$ or NR$^b$, and one or two methyne groups are optionally replaced by N, wherein the heterocycle formed by said optional replacement is other than heteroaryl, and wherein when V represents oxygen, sulfur or a single bond and W represents C$_1$-C$_6$ alkylene, C$_2$-C$_6$ alkenylene or C$_2$-C$_6$ alkynylene, then Y is other than C$_1$-C$_6$ alkyl;

or X represents NR$^a$ and Y represents C$_1$-C$_6$ alkylsulfonyl, C$_2$-C$_6$ alkenylsulfonyl, C$_2$-C$_6$ alkynylsulfonyl, arylsulfonyl, heteroarylsulfonyl, C$_1$-C$_6$ alkylsulfinyl, arylsulfinyl, heteroarylsulfinyl, (C$_1$-C$_6$ alkyl)carbonyl, (C$_2$-C$_6$ alkenyl)carbonyl, (C$_2$-C$_6$ alkynyl)carbonyl, arylcarbonyl, heteroarylcarbonyl, (C$_1$-C$_6$ alkyl)aminocarbonyl, (C$_2$-C$_6$ alkenyl)aminocarbonyl, (C$_2$-C$_6$ alkynyl)aminocarbonyl, arylaminocarbonyl, heteroarylaminocarbonyl, (C$_1$-C$_6$ alkylsulfonyl)C$_1$-C$_3$ alkyl, (C$_2$-C$_6$ alkenylsulfonyl)C$_1$-C$_3$ alkyl, (C$_2$-C$_6$ alkynylsulfonyl)C$_1$-C$_3$ alkyl, (arylsulfonyl)C$_1$-C$_3$ alkyl, (heteroarylsulfonyl)C$_1$-C$_3$ alkyl, (C$_1$-C$_6$ alkylsulfinyl)C$_1$-C$_3$ alkyl, (arylsulfinyl)C$_1$-C$_3$ alkyl, (heteroarylsulfinyl)C$_1$-C$_3$ alkyl, (C$_1$-C$_6$ alkyl)aminocarbonyl(C$_1$-C$_3$)alkyl, (C$_2$-C$_6$ alkenyl)$_a$-aminocarbonyl(C$_1$-C$_3$)alkyl, (C$_2$-C$_6$ alkynyl)aminocarbonyl(C$_1$-C$_3$)alkyl, (arylaminocarbonyl)C$_1$-C$_3$ alkyl or (heteroarylaminocarbonyl)C$_1$-C$_3$ alkyl;

wherein alkyl, alkenyl and alkynyl portions may be partly or completely fluorinated, and when R$^a$ represents H or (C$_1$-C$_4$ alkyl)carbonyl, then Y is other than (C$_1$-C$_6$ alkyl)carbonyl or arylcarbonyl;

Z represents oxygen; sulfur; SO; SO$_2$; 1,1-cyclopropylene; carbonyl; or methylene optionally substituted with one to two substituents independently selected from halo, hydroxy, C$_1$-C$_6$ alkyl, C$_1$-C$_6$ alkoxy, C$_3$-C$_6$ cycloalkyl and C$_3$-C$_6$ cycloalkyloxy;

R$^1$ represents hydrogen, halo, C$_1$-C$_6$ alkyl, C$_2$-C$_6$ alkenyl, C$_2$-C$_6$ alkynyl, C$_3$-C$_{10}$ cycloalkyl, (C$_3$-C$_{10}$)cycloalkyl-(C$_1$-C$_3$)alkyl, (C$_2$-C$_4$ alkenyl)C$_1$-C$_3$ alkyloxy, (C$_2$-C$_4$ alkynyl)C$_1$-C$_3$ alkyloxy, (C$_3$-C$_{10}$ cycloalkyl)C$_2$-C$_4$ alkenyl, C$_3$-C$_6$ cycloalkylidenemethyl, (C$_3$-C$_{10}$ cycloalkyloxy)C$_1$-C$_3$ alkyl, C$_5$-C$_{10}$) cycloalkenyl, (C$_5$-C$_{10}$)cycloalkenyl-(C$_1$-C$_3$)alkyl, (C$_1$-C$_4$ alkyloxy)C$_1$-C$_3$ alkyl, (C$_1$-C$_4$ alkylamino)C$_1$-C$_3$ alkyl, di-(C$_1$-C$_3$ alkylamino)C$_1$-C$_3$ alkyl, aryl, heteroaryl, (C$_1$-C$_4$ alkyl)carbonyl, arylcarbonyl, heteroarylcarbonyl, hydroxycarbonyl, aminocarbonyl, (C$_1$-C$_4$ alkyl)aminocarbonyl, di-(C$_1$-C$_3$ alkyl)aminocarbonyl, pyrrolidin-1-ylcarbonyl, piperidin-1-ylcarbonyl, morpholin-4-ylcarbonyl, piperazin-1-ylcarbonyl, 4-(C$_1$-C$_4$ alkyl)piperazin-1-ylcarbonyl, (C$_1$-C$_4$ alkyloxy)carbonyl, amino, C$_1$-C$_4$ alkylamino, di-(C$_1$-C$_3$ alkyl)amino, pyrrolidin-1-yl, piperidin-1-yl, morpholin-4-yl, piperazin-1-yl, 4-(C$_1$-C$_4$ alkyl)piperazin-1-yl, (C$_1$-C$_4$ alkyl)carbonylamino, arylcarbonylamino, C$_1$-C$_4$ alkylsulfonylamino, arylsulfonylamino, heteroarylcarbonylamino, C$_1$-C$_6$ alkyloxy, C$_3$-C$_{10}$ cycloalkyloxy, C$_5$-C$_7$ cycloalkenyloxy, aryloxy, heteroaryloxy, (aryl)C$_1$-C$_3$ alkyloxy, (heteroaryl)C$_1$-C$_3$ alkyloxy, C$_1$-C$_4$ alkylsulfanyl, C$_1$-C$_4$ alkylsulfinyl, C$_1$-C$_4$ alkylsulfonyl, C$_3$-C$_{10}$ cycloalkylsulfanyl, C$_3$-C$_{10}$ cycloalkylsulfinyl, C$_3$-C$_{10}$ cycloalkylsulfonyl, C$_5$-C$_{10}$ cycloalkenylsulfanyl, C$_5$-C$_{10}$ cycloalkenylsulfinyl, C$_5$-C$_{10}$ cycloalkenylsulfonyl, arylsulfanyl, arylsulfinyl, arylsulfonyl, hydroxy, cyano or nitro;

wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, C$_1$-C$_3$ alkoxy and C$_1$-C$_3$ alkyl, and in cycloalkyl and cycloalkenyl groups or portions one or two methylene groups are optionally replaced independently of one another by O, S, CO, SO or SO$_2$, and in N-heterocycloalkyl groups or portions a methylene group optionally may be replaced by CO or $SO_2$;

$R^2$ represents hydrogen, halo, hydroxy, $C_1$-$C_4$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_4$ alkyloxy, $C_3$-$C_{10}$ cycloalkyloxy, cyano or nitro, wherein alkyl and cycloalkyl groups or portions optionally may be mono- or polysubstituted by fluorine, or in the event that $R^1$ and $R^2$ are bound to two adjacent C atoms of the phenyl ring, $R^1$ and $R^2$ may be joined together such that R and $R^2$ together form a $C_3$-$C_5$ alkylene, $C_3$-$C_5$ alkenylene or butadienylene bridge, which may be partly or completely fluorinated and may be mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methyne groups optionally may be replaced by N;

$R^3$ represents hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$)alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_3$-$C_{10}$ cycloalkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_3$-$C_{10}$ cycloalkyl)$C_2$-$C_4$ alkenyl, $C_3$-$C_6$ cycloalkylidenemethyl, aryl, heteroaryl, ($C_1$-$C_4$ alkyl) carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl) piperazin-1-ylcarbonyl, hydroxycarbonyl, ($C_1$-$C_4$ alkyloxy) carbonyl, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, heteroaryl-carbonylamino, $C_1$-$C_4$ alkylsulfonylamino, arylsulfonylamino, $C_1$-$C_6$ alkyloxy, $C_3$-$C_{10}$ cycloalkyloxy, $C_5$-$C_7$ cycloalkenyloxy, aryloxy, heteroaryloxy, ($C_2$-$C_4$ alkenyl)$C_1$-$C_3$ alkyloxy, ($C_2$-$C_4$ alkynyl)$C_1$-$C_3$ alkyloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, amino, hydroxy, cyano or nitro, wherein alkyl, alkenyl, alkynyl, cycloalkyl and cycloalkenyl groups or portions optionally may be partly or completely fluorinated and mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by O, S, CO, SO or $SO_2$, and in N-heterocycloalkyl groups or portions a methylene group optionally may be replaced by CO or $SO_2$;

$R^4$ independently represents hydrogen, halo, cyano, nitro, hydroxy, $C_1$-$C_3$ alkyl, $C_3$-$C_{10}$ cycloalkyl, $C_1$-$C_3$ alkyloxy or $C_3$-$C_{10}$ cycloalkyloxy, wherein alkyl and cycloalkyl groups or portions optionally may be mono- or polysubstituted by fluorine, or if $R^3$ and $R^4$ are bound to two adjacent C atoms of the phenyl ring, $R^3$ and $R^4$ optionally may be joined together such that $R^3$ and $R^4$ together form a $C_3$-$C_5$ alkylene, $C_3$-$C_5$ alkenylene or butadienylene bridge, which may be partly or completely fluorinated and mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methyne groups may be replaced by N;

$R^5$ independently represents hydrogen, halo, cyano, nitro, hydroxy, $C_1$-$C_3$ alkyl, $C_3$-$C_{10}$ cycloalkyl or $C_1$-$C_3$ alkyloxy, wherein alkyl and cycloalkyl groups or portions optionally may be mono- or polysubstituted by fluorine; and $R^6$, $R^7$, $R^8$ and $R^9$ each independently represent hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, ($C_3$-$C_{10}$ cycloalkyl)carbonyloxy, hydrogen, halo, $C_1$-$C_6$ alkyl, $C_2$-$C_6$ alkenyl, $C_2$-$C_6$ alkynyl, ($C_3$-$C_{10}$)cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, $C_3$-$C_7$ cycloalkyloxy, $C_5$-$C_7$ cycloalkenyloxy, aryloxy, heteroaryloxy, ($C_3$-$C_7$)cycloalkyl-($C_1$-$C_3$) alkyloxy, ($C_5$-$C_7$)cycloalkenyl-($C_1$-$C_3$)alkyloxy, aryl-($C_1$-$C_3$)alkyloxy, heteroaryl-($C_1$-$C_3$)alkyloxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkyloxy)carbonyl, aminocarbonyl-($C_1$-$C_3$)alkyl, ($C_1$-$C_4$ alkyl)aminocarbonyl-($C_1$-$C_3$) alkyl, di-($C_1$-$C_3$ alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$)alkyl, ($C_3$-$C_7$)cycloalkyloxy-($C_1$-$C_3$)alkyl, ($C_5$-$C_7$) cycloalkenyloxy-($C_1$-$C_3$)alkyl, aryloxy-($C_1$-$C_3$)alkyl, heteroaryloxy-($C_1$-$C_3$)alkyl, $C_1$-$C_4$ alkylsulfonyloxy, arylsulfonyloxy, aryl-($C_1$-$C_3$)alkyl-sulfonyloxy, trimethylsilyloxy, t-butyldimethylsilyloxy, or cyano;

wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^b$, O, S, CO, SO or $SO_2$;

$R^a$ independently represents H, $C_1$-$C_6$ alkyl, $C_3$-$C_6$ cycloalkyl or ($C_1$-$C_4$ alkyl)carbonyl, wherein alkyl and cycloalkyl groups or portions optionally may be partly or completely fluorinated;

$R^b$ independently represents H, $C_1$-$C_4$ alkyl or ($C_1$-$C_4$ alkyl)carbonyl, wherein alkyl groups or portions optionally may be partly or completely fluorinated;

$R^c$ independently represents H, $C_1$-$C_4$ alkyl, $C_3$-$C_6$ cycloalkyl, $CHR^dR^e$, $SO_2R^d$, $C(O)OR^d$ or $C(O)NR^dR^e$, wherein alkyl and cycloalkyl groups optionally may be partly or completely fluorinated; and $R^d$ and $R^e$ each independently represent H or $C_1$-$C_6$ alkyl, wherein alkyl groups optionally may be partly or completely fluorinated.

The style used above and hereinafter, in which a bond of a substituent on a phenyl group is shown ending near the center of the phenyl ring, denotes, unless otherwise stated, that this substituent may be bound to any free position of the phenyl group bearing a hydrogen atom.

The present invention includes all tautomers and stereoisomers of compounds of Formula I, either in admixture or in pure or substantially pure form. The compounds of the present invention can have asymmetric centers at the carbon atoms, and therefore the compounds of Formula I can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

The present invention also provides for the prodrugs of compounds of Formula I. Prodrugs of compounds of the invention include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates may be formed, for example, by reacting one or more hydroxyl groups of compounds of Formula I with alkyl, alkoxy or aryl substituted acylating reagents using methods known to those of skill in the art to produce methyl carbonates, acetates, benzoates, pivalates and the like. Illustrative examples of prodrug esters of the compounds of the present invention include, but are not limited to, compounds of Formula I having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)-ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy)ethyl, N—(($C_1$-$C_5$)alkoxycarbonyl)aminomethyl, 1-(N—(($C_1$-$C_5$)alkoxycarbonyl)amino)ethyl, 3-phthalidyl, 4-crotonolactonyl, gamma-butyrolacton-4-yl, di-N,N-($C_1$-$C_2$)alkylamino($C_2$-$C_3$)alkyl (e.g., beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl. Oligopeptide modifications and biodegradable polymer derivatives (as described, for example, in Int. J. Pharm. 115, 61-67, 1995) are within the scope of the invention. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, "Design of Prodrugs," Elsevier, 1985; and "Bioreversible Carriers in Drug Design," ed. Edward Roche, American Pharmaceutical Association and Pergamon Press, 1987.

The present invention also provides for the pharmaceutically acceptable salts of compounds of Formula I and prodrugs thereof. The acids that can be used as reagents to prepare the pharmaceutically acceptable acid addition salts of the basic compounds of this invention are those which form non-toxic acid addition salts, i.e., salts containing pharmacologically acceptable anions (such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (1,1'-methylene-bis-2-hydroxy-3-naphthoate) salts). The bases that can be used as reagents to prepare the pharmaceutically acceptable base salts of the acidic compounds of the present invention are those that form non-toxic base salts with such compounds, including, but not limited to, those derived from pharmacologically acceptable cations such as alkali metal cations (e.g., potassium, lithium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines (e.g., methylamine, ethylamine, propylamine, dimethylamine, triethanolamine, diethylamine, t-butylamine, t-octylamine, trimethylamine, triethylamine, ethylenediamine, hydroxyethylamine, morpholine, piperazine, dehydroabietylamine, lysine and guanidine).

The present invention also includes isotopically-labeled compounds of Formula I, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2H$, $^3H$, $^{13}C$, $^{14}C$, $^{15}N$, $^{18}O$, $^{17}O$, $^{18}F$, $^{35}S$ and $^{36}Cl$). Isotopically-labeled compounds of Formula I and prodrugs thereof, as well as isotopically-labeled, pharmaceutically acceptable salts of compounds of Formula I and prodrugs thereof, are within the scope of the present invention. Isotopically-labeled compounds of the present invention are useful in assays of the tissue distribution of the compounds and their prodrugs and metabolites; preferred isotopes for such assays include $^3H$ and $^{14}C$. In addition, in certain circumstances substitution with heavier isotopes, such as deuterium ($^2H$), can provide increased metabolic stability, which offers therapeutic advantages such as increased in vivo half-life or reduced dosage requirements. Isotopically-labeled compounds of this invention and prodrugs thereof can generally be prepared according to the methods described herein by substituting an isotopically-labeled reagent for a non-isotopically labeled reagent.

In preferred embodiments, A represents oxygen or sulfur. In particularly preferred embodiments, A represents oxygen.

In preferred embodiments, V represents oxygen, sulfur or a single bond. In particularly preferred embodiments, V represents oxygen or a single bond.

In certain preferred embodiments, W represents $C_1$-$C_6$ alkylene or $C_3$-$C_{10}$ cycloalkylene;
wherein alkylene and cycloalkylene groups may be partly or completely fluorinated and may be mono- or disubstituted by identical or different substituents selected from chlorine, hydroxy, $C_1$-$C_3$ alkyl or $C_1$-$C_3$ alkoxy, and
in cycloalkylene groups one or two methylene groups are optionally replaced independently of one another by O, S, CO, SO, $SO_2$ or $NR^b$;
In particularly preferred embodiments, W represents $C_1$-$C_6$ alkylene.

In certain preferred embodiments, X represents oxygen or sulfur.

In certain preferred embodiments, Y represents $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, $C_5$-$C_{10}$ cycloalkenyl, ($C_1$-$C_4$ alkyloxy)$C_1$-$C_3$ alkyl, ($C_2$-$C_4$ alkenyloxy)$C_1$-$C_3$ alkyl or ($C_3$-$C_{10}$ cycloalkyloxy)$C_1$-$C_3$ alkyl;
wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkyl and $C_1$-$C_3$ alkoxy, and
in cycloalkyl and cycloalkenyl groups or portions one or two methylene groups are optionally replaced independently of one another by O, S, CO, SO, $SO_2$ or $NR^b$, and one or two methyne groups are optionally replaced by N, wherein the heterocycle formed by said optional replacement is other than heteroaryl;

In preferred embodiments, Z represents oxygen, sulfur, or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy. In particularly preferred embodiments, Z represents methylene.

In certain preferred embodiments, $R^1$ represents hydrogen, halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein alkyl and cycloalkyl groups or portions may be partly or completely fluorinated. In particularly preferred embodiments, $R^1$ represents hydrogen, halo or $C_1$-$C_6$ alkyl.

In certain preferred embodiments, $R^2$ represents hydrogen, hydroxy, halo, $C_1$-$C_4$ alkyl, or $C_1$-$C_4$ alkyloxy. In particularly preferred embodiments, $R^2$ represents hydrogen or halo.

In preferred embodiments, $R^3$ represents hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein alkyl and cycloalkyl groups or portions optionally may be partly or completely fluorinated, and in cycloalkyl groups one or two methylene groups are optionally replaced independently of one another by O, S, CO, SO or $SO_2$. In particularly preferred embodiments, $R^3$ represents hydrogen, halo, $C_1$-$C_6$ alkyl, $C_1$-$C_6$ alkyloxy, $C_2$-$C_6$ alkenyl, $C_2$-$C_6$ alkynyl, $C_3$-$C_{10}$ cycloalkyl, or $C_3$-$C_{10}$ cycloalkyloxy, wherein alkyl and cycloalkyl groups or portions optionally may be partly or completely fluorinated, and in cycloalkyl groups a methylene group is optionally replaced by O, S, CO, SO or $SO_2$.

In preferred embodiments, $R^4$ and $R^5$ independently represent hydrogen, halo, hydroxy, cyano, nitro, $C_1$-$C_3$ alkyl, $C_3$-$C_{10}$ cycloalkyl or $C_1$-$C_3$ alkoxy. In particularly preferred embodiments, $R^4$ and $R^5$ independently represent hydrogen, hydroxy or halo.

In preferred embodiments, $R^6$, $R^7$, $R^8$ and $R^9$ each independently represent hydroxy, halo, ($C_1$-$C_6$ alkyl)carbonyloxy, ($C_1$-$C_6$ alkyl)oxycarbonyloxy, arylcarbonyloxy, aryl-($C_1$-$C_3$ alkyl)carbonyloxy, ($C_3$-$C_{10}$ cycloalkyl)carbonyloxy, $C_1$-$C_6$ alkyl, $C_1$-$C_6$ alkyloxy, ($C_3$-$C_7$)cycloalkyloxy, aryloxy or ($C_3$-$C_7$)cycloalkyl-($C_1$-$C_3$)alkyloxy, wherein alkyl and cycloalkyl groups or portions may be partly or completely fluorinated. In particularly preferred embodiments, $R^6$, $R^7$, $R^8$ and $R^9$ each represent hydroxy.

As noted above, still other preferred embodiments are represented by Formula IA:

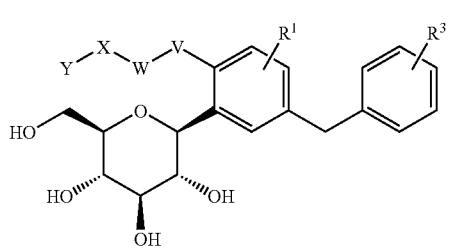

IA wherein, V represents oxygen or a single bond;
W represents $C_1$-$C_6$ alkylene;
X represents oxygen or sulfur;
Y represents $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, $C_5$-$C_{10}$ cycloalkenyl, ($C_1$-$C_4$ alkyloxy)$C_1$-$C_3$ alkyl, ($C_2$-$C_4$ alkenyloxy)$C_1$-$C_3$ alkyl or ($C_3$-$C_{10}$ cycloalkyloxy)$C_1$-$C_3$ alkyl;
wherein alkyl, alkenyl, alkynyl, cycloalkyl and cycloalkenyl groups or portions optionally may be partly or completely fluorinated and may be mono- or disubstituted by identical or different substituents selected from chlorine, hydroxy, $C_1$-$C_3$ alkyl and $C_1$-$C_3$ alkoxy, and
in cycloalkyl and cycloalkenyl groups or portions one or two methylene groups are optionally replaced independently of one another by O, S, CO, SO, $SO_2$ or $NR^b$, and one or two methyne groups are optionally replaced by N, wherein the heterocycle formed by said optional replacement is other than heteroaryl;
$R^1$ represents hydrogen, halo, $C_1$-$C_6$ alkyl or $C_3$-$C_{10}$ cycloalkyl; and
$R^3$ represents hydrogen, halo, hydroxy, $C_1$-$C_6$ alkyl, $C_1$-$C_6$ alkyloxy, $C_2$-$C_6$ alkenyl, $C_2$-$C_6$ alkynyl, $C_3$-$C_{10}$ cycloalkyl, or $C_3$-$C_{10}$ cycloalkyloxy, wherein alkyl and cycloalkyl groups or portions optionally may be partly or completely fluorinated, and in cycloalkyl groups a methylene group is optionally replaced by O, S, CO, SO or $SO_2$.

As noted above, still other particularly preferred embodiments are represented by Formula IB:

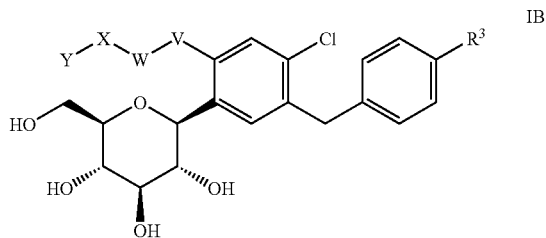

IB wherein, V represents oxygen or a single bond;
W represents $C_1$-$C_6$ alkylene;
X represents oxygen or sulfur;
Y represents $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, ($C_1$-$C_4$ alkyloxy) $C_1$-$C_3$ alkyl, ($C_2$-$C_4$ alkenyloxy)$C_1$-$C_3$ alkyl or ($C_3$-$C_{10}$ cycloalkyloxy)$C_1$-$C_3$ alkyl;
wherein alkyl, alkenyl, alkynyl and cycloalkyl groups or portions optionally may be partly or completely fluorinated and may be mono- or disubstituted by identical or different substituents selected from chlorine, hydroxy, $C_1$-$C_3$ alkyl and $C_1$-$C_3$ alkoxy, and
in cycloalkyl groups or portions one or two methylene groups are optionally replaced independently of one another by O, S, CO or $NR^b$;
$R^3$ represents ethyl, ethenyl, ethynyl or ethoxy.

In another aspect, the present invention includes the compounds of Formula I and pharmaceutically acceptable salts, prodrugs and/or isotopically labeled compounds thereof, wherein alkyl, alkenyl, alkynyl, cycloalkyl, cycloalkenyl, aryl and heteroaryl groups or portions are optionally substituted with one to three suitable substituents as defined above.

In other aspects, the present invention provides intermediates and processes useful for preparing the intermediates below as well as the compounds of Formula I, and pharmaceutically acceptable salts and prodrugs thereof.

Such processes are outlined in the following general preparative methods depicted in Schemes VI-III (FIGS. 1-8), with more detailed particular examples being presented below in the experimental section describing the working examples. By following the general preparative methods discussed below, or employing variations or alternative methods, the compounds of the invention can be readily prepared by the use of chemical reactions and procedures known to those of skill in the art. Unless otherwise specified, the variables (e.g., R groups) denoting groups in the general methods described below have the meanings as hereinbefore defined.

Those of skill in the art will recognize that compounds of the invention with each described functional group are generally prepared using slight variations of the below-listed general methods. Within the scope of each method, functional groups which are suitable to the reaction conditions are used. Functional groups which might interfere with certain reactions are presented in protected forms where necessary, and the removal of such protective groups is completed at appropriate stages by methods well known to those skilled in the art.

In certain cases compounds of the invention can be prepared from other compounds of the invention by elaboration, transformation, exchange and the like of the functional groups present. Such elaboration includes, but is not limited to, hydrolysis, reduction, oxidation, alkylation, acylation, esterification, amidation and dehydration. Such transformations can in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

In another aspect, the present invention provides for synthetic intermediates useful for preparing the compounds of Formula I, and pharmaceutically acceptable salts and prodrugs thereof, according to the general preparative methods discussed below and other processes known to those of skill in the art.

When the following abbreviations and acronyms are used throughout the disclosure, they have the following meanings: 18-Crown-6,1,4,7,10,13,16-hexaoxacyclooctadecane; ADDP, 1,1'-(azodicarbonyl)dipiperidine; 9-BBN, 9-borabicyclo[3.3.1]nonane; $BF_3.Et_2O$, boron trifluoride diethyl etherate; $Bu_3P$, tri-n-butylphosphine; n-BuLi, n-butyllithium; t-BuLi, t-butyllithium; t-BuOK, potassium tert-butoxide; calc., calculated; $CD_3OD$, methanol-$d_4$; $CDCl_3$, chloroform-d; $CH_2Cl_2$, methylene chloride; $CH_3CN$, acetonitrile; $(COCl)_2$, oxalyl dichloride; conc., concentrated; $CrO_3$, chromium trioxide; DAST, (diethylamino)sulfur trifluoride; DMAP, 4-dimethylaminopyridine; DMF, N,N-dimethylformamide; DMSO, dimethylsulfoxide; Et, ethyl; $Et_3N$, triethylamine; EtOAc, ethyl acetate; EtOH, ethanol; h, hour; $H_2$, hydrogen gas; HCl, hydrochloric acid; $^1$H-NMR, proton nuclear magnetic resonance; HPLC, high performance liquid chromatography; $H_2SO_4$, sulfuric acid; HWE, Horner-Wadsworth-Emmons; $K_2CrO_4$, potassium chromate; $IKMnO_4$, potassium permanganate; KOH, potassium hydroxide; LC-MS, liquid chromatography mass spectroscopy; LDA, lithium diisopropylamide; Me, methyl; MeOH, methanol; $MeSO_3H$, methanesulfonic acid; min, minute; MS ESI, mass spectroscopy with electrospray ionization; NaH, sodium hydride; $NaHCO_3$, sodium bicarbonate; NaOH, sodium hydroxide; $Na_2SO_4$, sodium sulfate; NBS, N-bromosuccinimide; $NH_3$, ammonia; NIS, N-iodosuccinimide; PCC, pyridinium chlorochromate; Pd/C, palladium on carbon; PDC, pyridinium dichromate; PE, petroleum ether; $R_f$, retention factor; satd, saturated; $SOCl_2$, thionyl chloride; TBAI, tetrabutylammonium iodide; TFA, trifluoroacetic acid; THF, tetrahydrofuran; TLC, thin layer chromatography; TMS-Cl, trimethylsilyl chloride (chlorotrimethylsilane).

General Synthesis Method of Scheme I

Inventive compounds of formula 16 can be conveniently prepared according to the reaction sequences as shown in Scheme I (FIG. 1).

As shown in Scheme I, the meso-amino benzoic acid 1 is halogenated by NBS, or NIS, or other reagent to afford intermediate 2, which is then converted to its corresponding ester 3 using standard esterification procedures, such as refluxing with $H_2SO_4$/MeOH or $SOCl_2$/MeOH. Using Sandmeyer reaction conditions, ester 3 is converted to compound 4. Oxidation of ester 4 with $CrO_3$, $K_2CrO_4$ or $KMnO_4$ produces benzoic acid 5. After treatment with an acylation reagent, such as $(COCl)_2$ or $SOCl_2$, acid 5 reacts with substituted aromatic ring 6 in the presence of a Lewis acid, such as $FeCl_3$ or $AlCl_3$, to give diphenylketone 7. The ketone on compound 7 is reduced with reductant, such as $Et_3SiH$, catalyzed by acid, such as TFA or $BF_3.Et_2O$, to give ester 8. Further reduction of ester 8 affords alcohol 9. The free alcohol 9 is then protected with alkylsilyl or ether and treated with activating reagent, such as n-BuLi or t-BuOK, followed by condensation with protected lactone 11 to give adduct 12, which is reduced with alkylsilane or other reductant in the presence of acid, such as TFA, $MeSO_3H$ or $BF_3.Et_2O$. Deprotection of the resulting intermediate 13 gives benzyl alcohol 14. Alkylation of benzyl alcohol 14 and deprotection of the resulting product 15 give the inventive compounds of formula 16.

In Scheme I and in other schemes below, the symbols P and $P^1$ denote protecting groups (typically ester- or ether-forming groups and the like). Additionally, the last step in Scheme I and in other schemes below shows a deprotection step. This step can be applied to any protecting group present on functional groups in the molecule (e.g., in $R^1$, $R^2$, $R^3$ and the like).

General Synthesis Method of Scheme II

Figure 2:
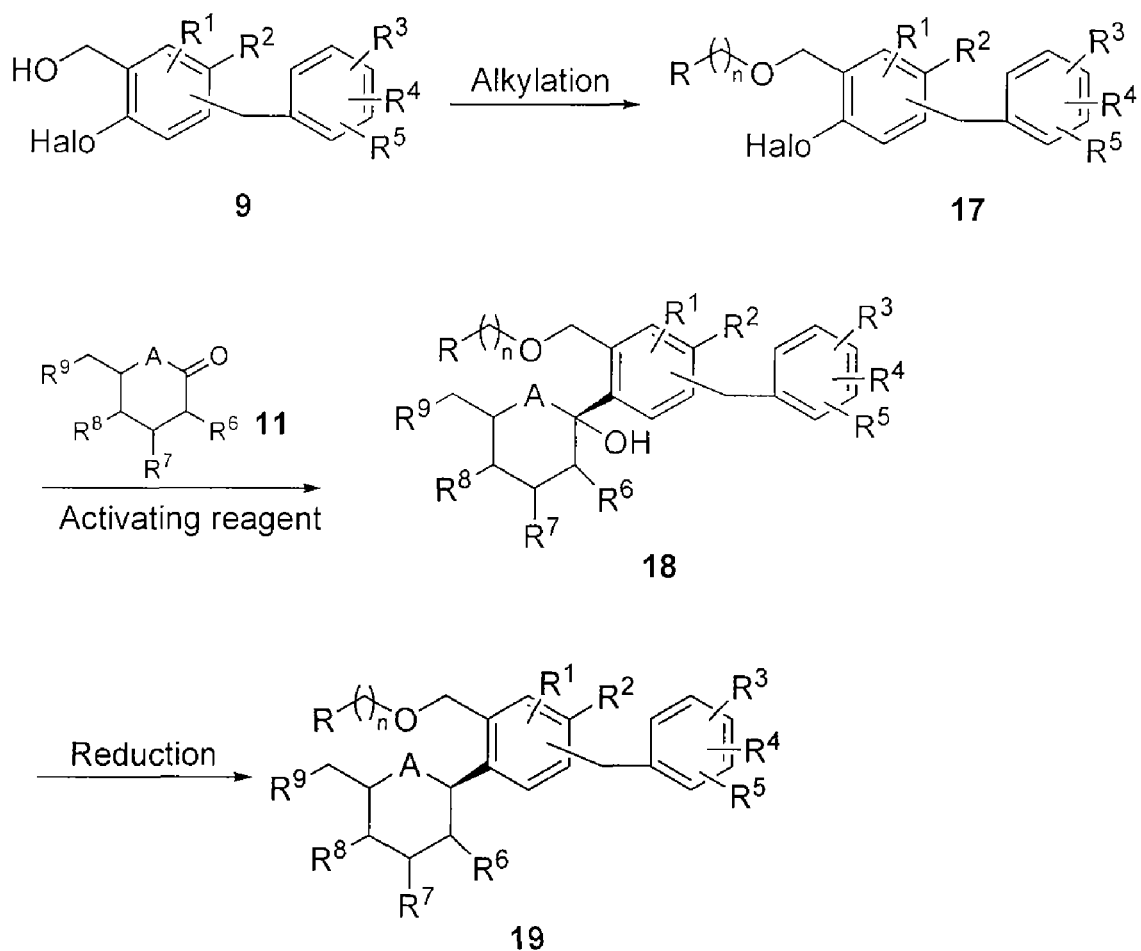
Figure 3:
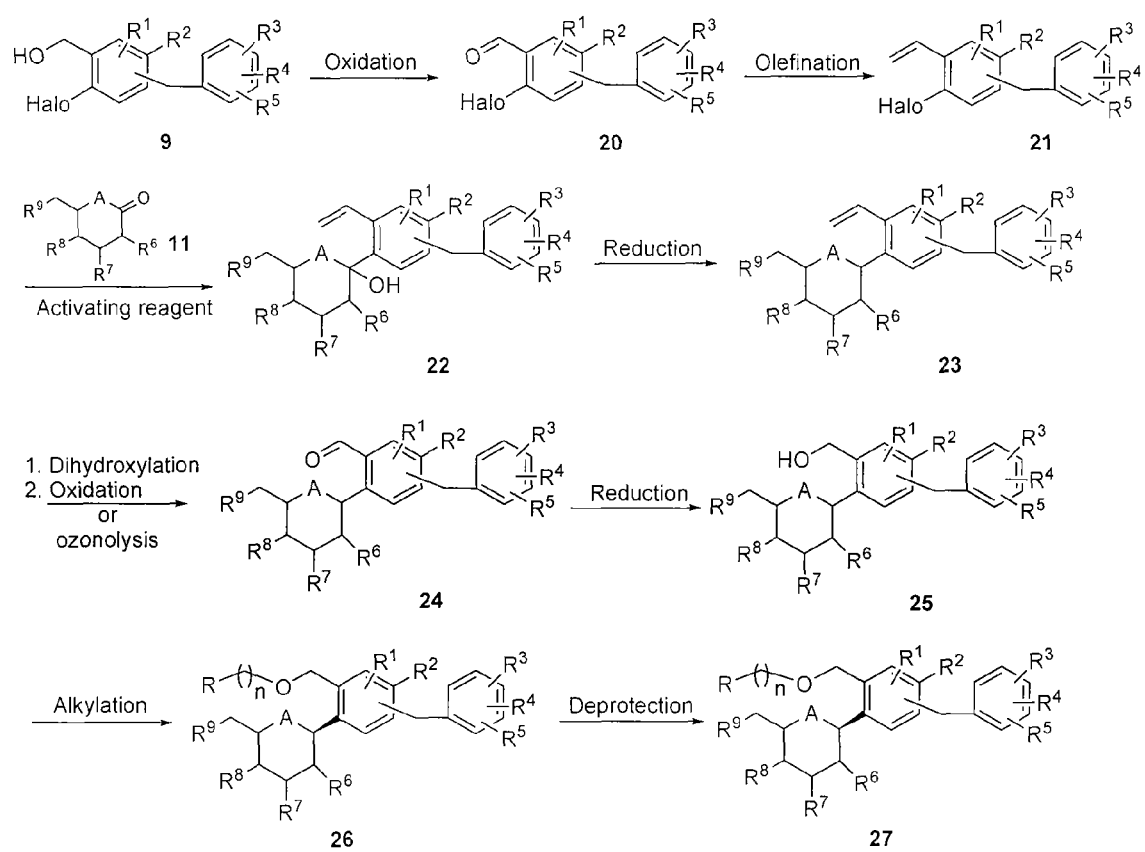
Figure 4:
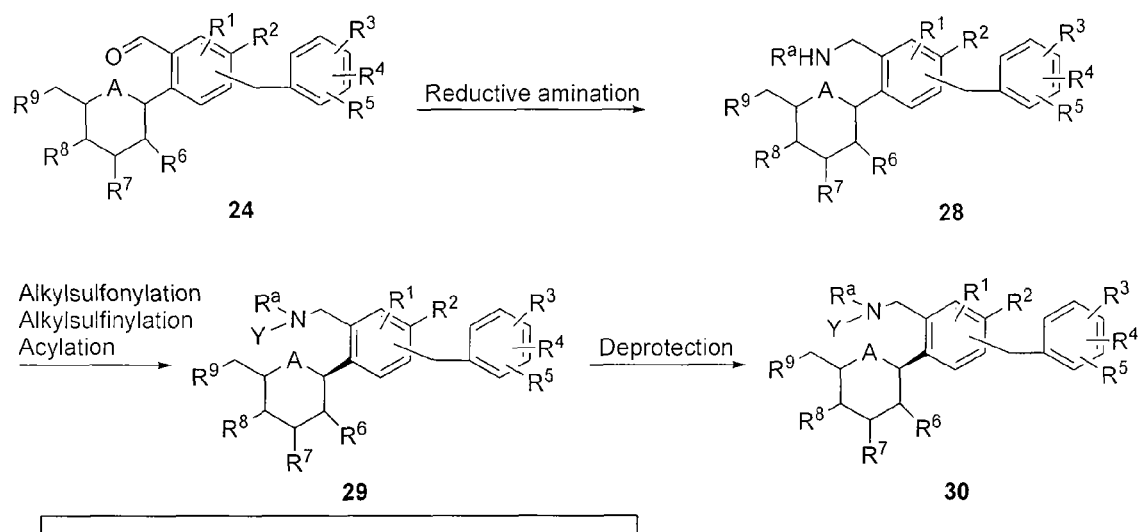
Figure 5:
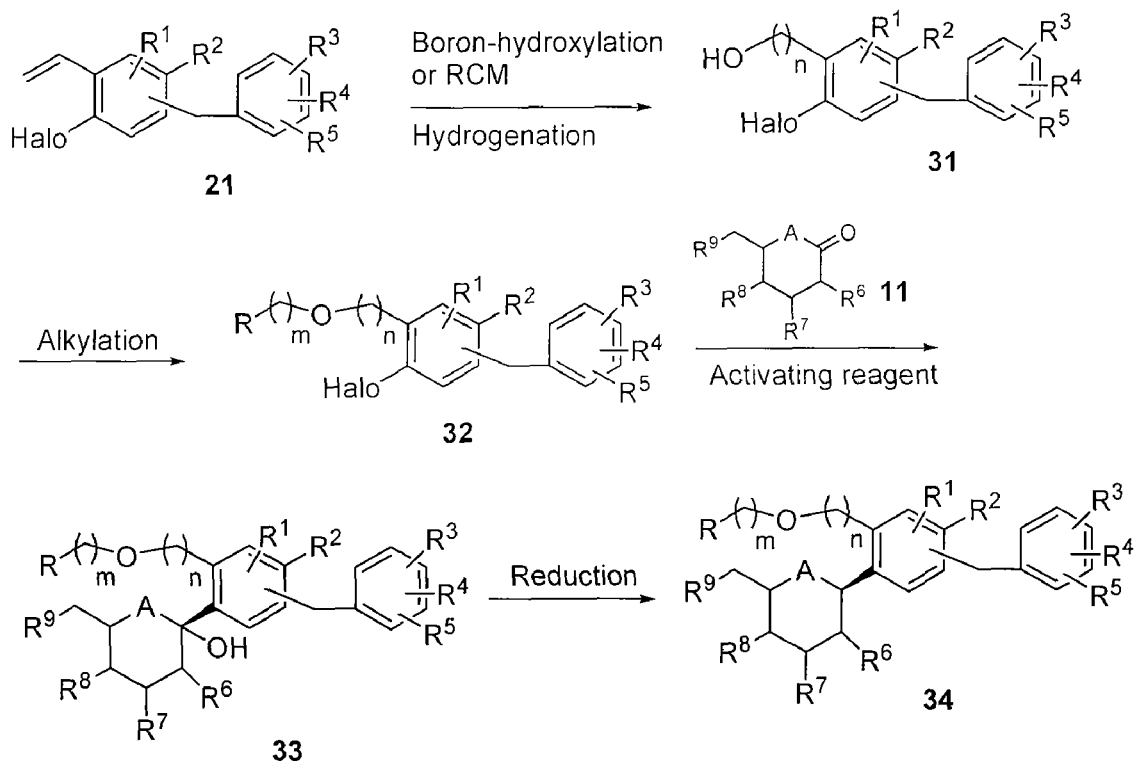
Figure 6:
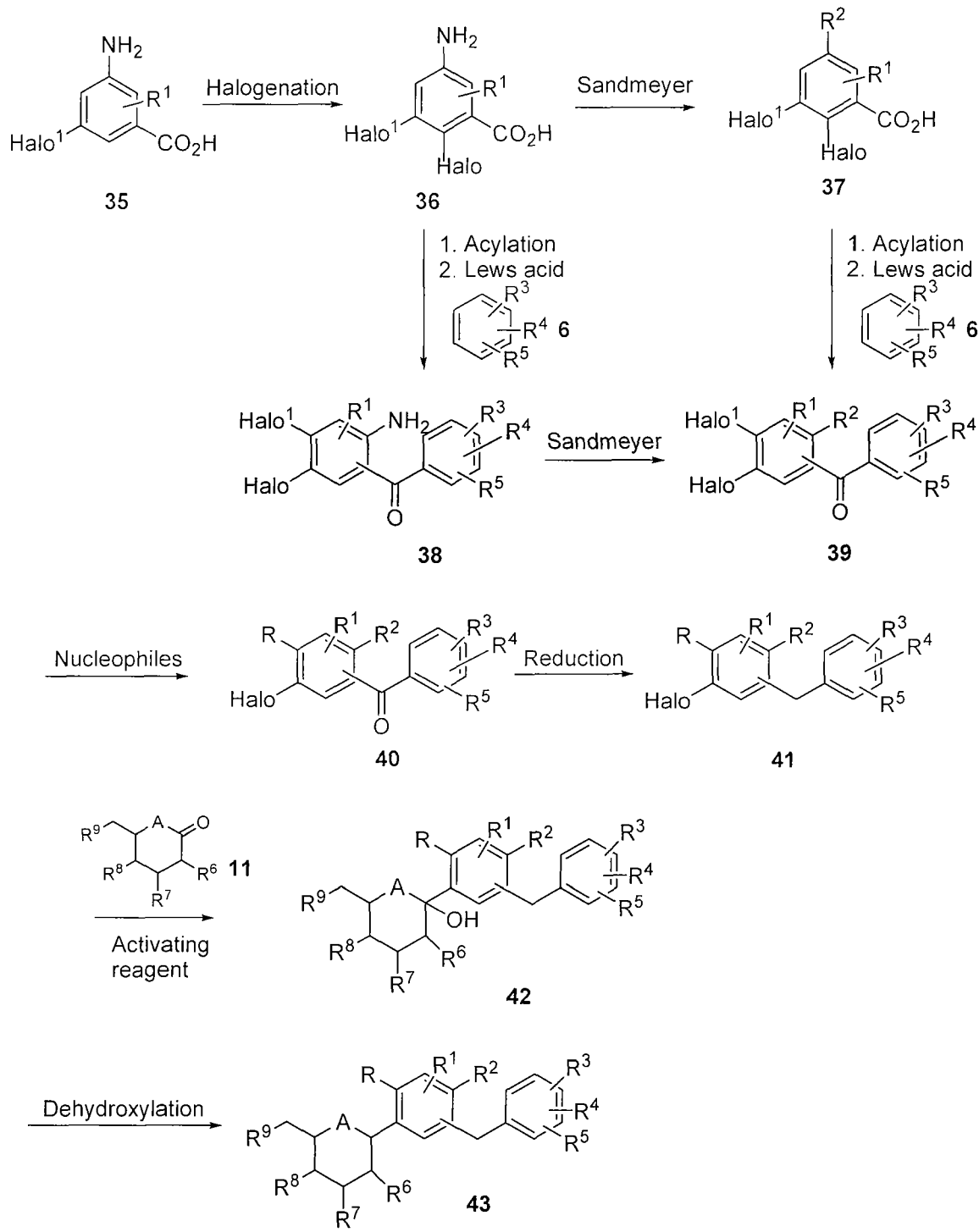
Figure 7:
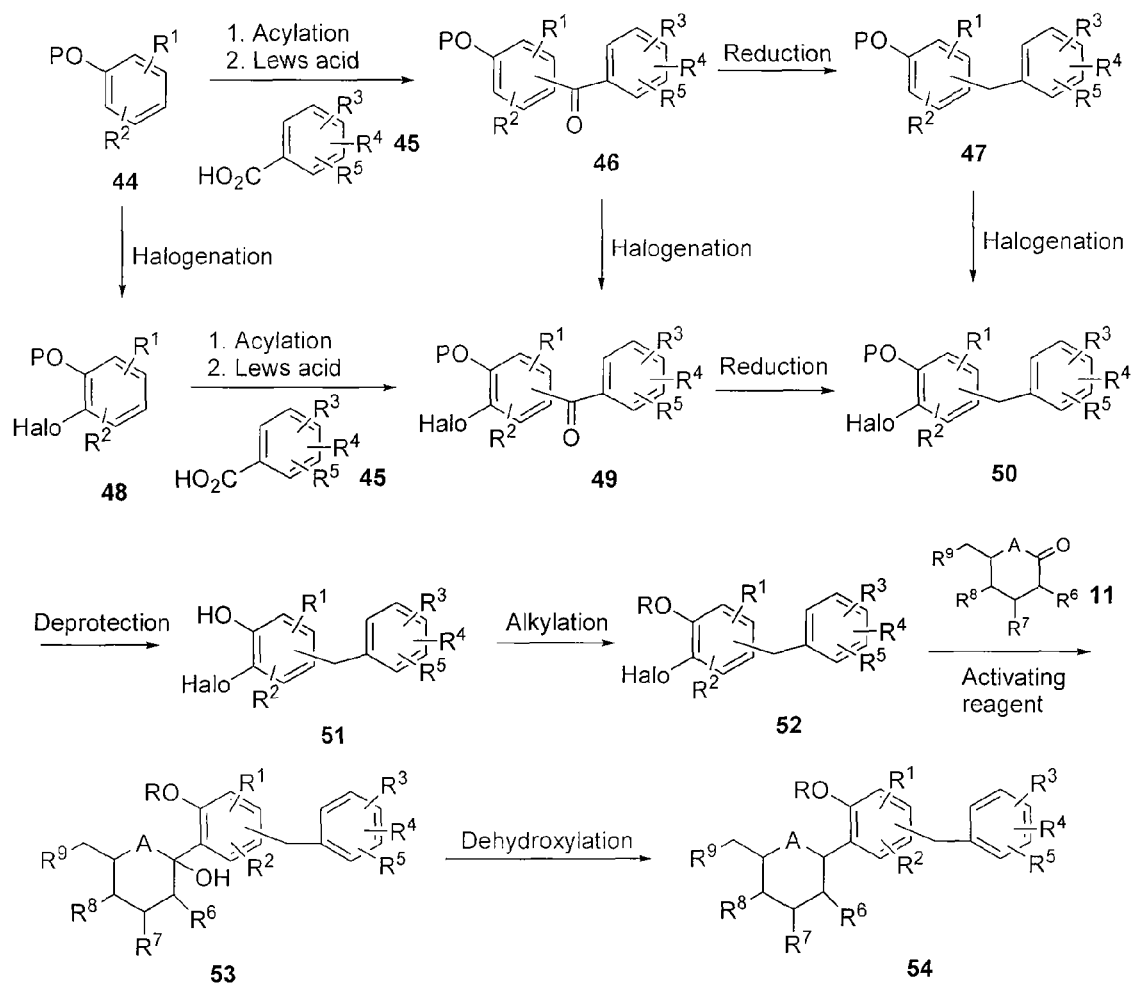
Figure 8:
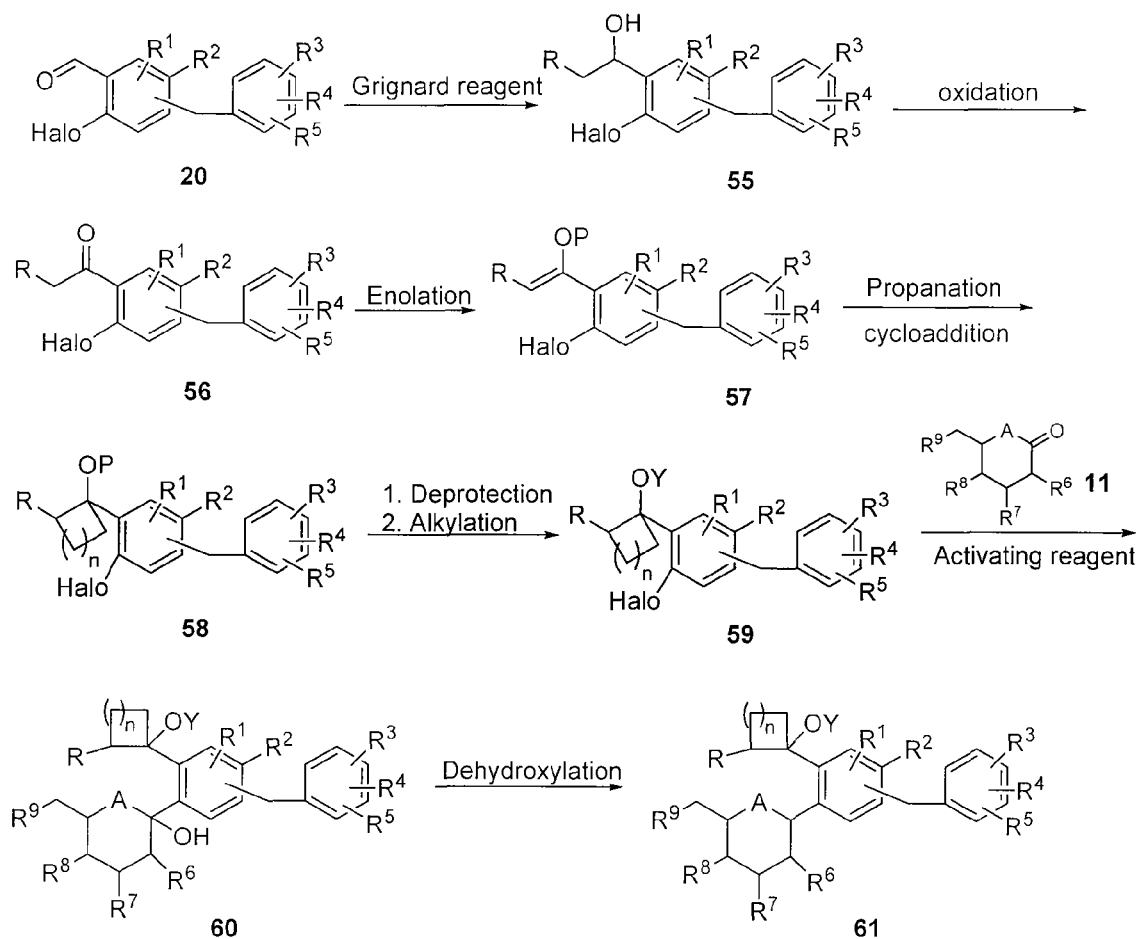

Inventive compounds of formula 19 can be conveniently prepared according to the reaction sequences as shown in Scheme II (FIG. 2).

The benzyl alcohol 9 is alkylated with reagent such as allyl bromide or aceylenemethyl bromide to form intermediate 17, which is condensed with ketone 11 after treatment with activating reagent, such as ii-BuLi or t-BuOK. The resulting adduct 18 is then reduced with alkylsilane or other reductant in the presence of acid, such as TFA, $MeSO_3H$ or $BF_3.Et_2O$ to generate the inventive compounds of formula 19.

General Synthesis Method of Scheme III

As shown in Scheme III (FIG. 3), the inventive compounds of formula 27 can also be prepared using an alternative route.

The benzyl alcohol 9 is oxidized to the corresponding aldehyde 20 using PCC, Dess-Martin reagent, or Swern reaction. Upon olefination under Wittig or HWE reaction conditions, aldehyde 20 is converted to the corresponding styrene 21, which is allowed to react with ketone 11 after treatment with activating reagent, such as ii-BuLi or t-BuOK, to give adduct 22. Compound 22 is reduced with alkylsilane or other reductant in the presence of acid, such as TFA, $MeSO_3H$ or $BF_3.Et_2O$ to form intermediate 23. Styrene 23 is then converted to the corresponding aldehyde 24 by dihydroxylation followed by oxidation with $NaIO_4$, or treatment with ozonolysis. Reduction of aldehyde 24 with $NaBH_4$ or other reducing agent gives benzyl alcohol 25, which is alkylated with a reagent such as allyl bromide or acetylenemethyl bromide to form intermediate 26. Deprotection and derivatization of intermediate 26 generates inventive compounds of formula 27.

General Synthesis Method of Scheme IV

As shown in Scheme IV (FIG. 4), inventive compounds of formula 30 can also be prepared by the following the reaction sequence.

The aldehyde 24 is converted to the corresponding amino derivative 28 by reductive amination. Alkylation or acylation of the intermediate 28 leads to compound 29, which is deprotected to form the inventive compounds of formula of 30.

General Synthesis Method of Scheme V

As shown in Scheme V (FIG. 5), the inventive compounds of formula 34 can be synthesized according to the outlined reaction sequence.

The olefin 21 is converted to the corresponding alcohol 31 by using Brown's boron-hydroxylation method or ring-closure-metathesis (RCM) in the presence of Grubb's catalyst, followed by hydrogenation. The alcohol 31 is alkylated or acylated to generate intermediate 32, which is debrominated with n-BuLi or t-BuOK and condensed with ketone 11. The adduct 33 is dehydrolyzed with alkylsilane or other reductant in the presence of acid, such as TFA, MeSO$_3$H or BF$_3$.Et$_2$O to form the inventive compounds of formula 34.

General Synthesis Method of Scheme VI

As shown in Scheme VI (FIG. 6), the inventive compounds of formula 43 can be synthesized using an alternative synthetic route.

The meso-amino benzoic acid 35 is halogenated by NBS, or NIS, or other reagent to afford intermediate 36. Using Sandmeyer reaction, the amino group of compound 36 is converted to halogen to form intermediate 37, which is treated with acylation reagent, such as (COCl)$_2$ or SOCl$_2$, followed by reaction with substituted aromatic ring 6 in the presence of a Lewis acid, such as FeCl$_3$ or AlCl$_3$, to give ketone 39. Alternatively, ketone 39 is also obtained through Sandmeyer reaction starting from intermediate 38, which is synthesized by treatment of amino benzoic acid 36 with acylation reagent followed by condensation of the resulting benzoyl chloride with substituted aromatic ring 6. Ketone 39 is then allowed to react with nucleophiles, such as alcohols or CuCN to give intermediate 40, which is reduced with alkylsilane in the presence of either Bronst acid or Lewis acid, such as TFA, MeSO$_3$H or BF$_3$.Et$_2$O. Debromination of the resulting intermediate 41 with n-BuLi or t-BuOK and condensation of the product in situ with ketone 11 gives adduct 42. Dehydroxylation of compound 42 with alkylsilane or other reductant in the presence of acid, such as TFA, MeSO$_3$H or BF$_3$.Et$_2$O, forms the inventive compounds of formula 43.

General Synthesis Method of Scheme VII

As shown in Scheme VII (FIG. 7), the inventive compounds of formula 54 can be synthesized using the outlined reaction sequence.

The substituted benzoic acid 45 is treated with acylation reagent, such as (COCl)$_2$ or SOCl$_2$, followed by reaction with protected phenol ring 44 in the presence of a Lewis acid, such as FeCl$_3$ or AlCl$_3$, to give ketone 46, which is reduced by alkylsilane or other reductant with the catalysis of Lewis acid, such as TFA, MeSO$_3$H or BF$_3$.Et$_2$O. The resulting diphenyl methane 47 is then halogenated with NBS, NIS or other reagent to afford intermediate 50. Deprotection of compound 50 and alkylation of the resulting phenol 51 leads to intermediate 52, which is then treated with activating reagent, such as n-BuLi or t-BuOK, followed by condensation with protected lactone 11 to give adduct 53. Dehydroxylation of intermediate 53 with alkylsilane or other reductant in the presence of acid, such as TFA, MeSO$_3$H or BF$_3$.Et$_2$O, and removal of the protection groups form the inventive compounds of formula 54. By reduction with alkylsilane in the presence of acid, such as TFA, MeSO$_3$H or BF$_3$.Et$_2$O, intermediate 50 can also be synthesized starting from ketone 49, which is the condensed product of protected phenol 48 and substituted benzoic acid 45 through a Friedel-Crafts reaction with the catalysis of Lewis acid, such as FeCl$_3$ or AlCl$_3$. The intermediates, 48 and 49, can both be prepared starting from compounds 44 and 46, respectively, using halogenation reagent, such as NBS or NIS.

General Synthesis Method of Scheme VIII

As shown in Scheme VIII (FIG. 8), the inventive compounds of formula 61 can be synthesized using the outlined reaction sequence.

The aldehyde 20 is treated with an organometallic reagent, such as MeMgI, to generate benzylic alcohol 55, which is oxidized to the corresponding ketone 56 using Swern or Dess-Martin reaction procedures. Ketone 56 is then converted to its enolate 57. Propanation or cycloaddition of the olefin on intermediate 57 leads to tri-cyclic compound 58. Removal of the protection group on the alcohol of intermediate 58 and alkylation of the resulting free alcohol give intermediate 59. Treatment of the halophenyl compound 59 with activating reagent, such as n-BuLi or t-BuOK, followed by condensation with protected lactone 11 give the adduct 60. Dehydroxylation of compound 53 with alkylsilane or other reductant in the presence of acid, such as TFA, MeSO$_3$H or BF$_3$.Et$_2$O, generates the inventive compounds as of formula 61.

Pharmaceutical Compositions and Methods of Use

The present invention further provides a pharmaceutical composition comprising an effective amount of a compound or mixture of compounds of Formula I, or a pharmaceutically acceptable salt or prodrug thereof, in a pharmaceutically acceptable carrier.

A compound of this invention can be incorporated into a variety of formulations for therapeutic administration. More particularly, a compound of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, the compound can be administered in a local rather than systemic manner, for example, in a depot or sustained release formulation.

Suitable formulations for use in the present invention are found in *Remington. The Science and Practice of Pharmacy*, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the alt, i.e., by means of conventional mixing, dissolving, granulating, dragee-making, levigating, emulsifying, encapsulating, entrapping or lyophilizing processes. The following methods and excipients are merely exemplary and are in no way limiting.

In one preferred embodiment, a compound of the present invention is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drag Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a compound of the present invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a compound of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in conventional manner.

In addition to the formulations described previously, a compound of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the compounds of Formula I in admixture with an effective amount of other therapeutic agents as combination partners, particularly those used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. An effective amount of the compound and/or combination partner will, of course, be dependent on the subject being treated, the severity of the affliction and the manner of administration. Determination of an effective amount is well within the capability of those skilled in the art, especially in light of the detailed disclosure provided herein. Generally, an efficacious or effective amount of a compound is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

The present invention further provides methods of using the compounds of Formula I for the prevention and treatment of disease. In one embodiment the invention provides a method of treating type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases, which comprises administering an effective amount of a compound or mixture of compounds of Formula I, or a pharmaceutically acceptable salt or prodrug thereof, to a subject in need thereof. In another embodiment the invention provides a method of using a compound or mixture of compounds of Formula I, or a pharmaceutically acceptable salt or prodrug thereof, for the preparation of a medicament for treating type 1 and type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis and related diseases.

The present invention also contemplates the use of the compounds of Formula I, or pharmaceutically acceptable salts or prodrugs thereof, in combination with other therapeutic agents, particularly those used for treating the above-mentioned diseases and conditions, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. Those skilled in the art will appreciate that other therapeutic agents discussed below can have multiple therapeutic uses and the listing of an agent in one particular category should not be construed to limit in any way its usefulness in combination therapy with compounds of the present invention.

Examples of antidiabetic agents suitable for use in combination with compounds of the present invention include insulin and insulin mimetics, sulfonylureas (such as acetohexamide, carbutamide, chlorpropamide, glibenclamide, glibornuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid X receptor agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), protein tyrosine phosphatase-1B inhibitors (such as KR61639, IDD-3, PTP-3848, PTP-112, OC-86839, PNU-177496, compounds described in Vats, R. K., et al., *Current Science*, Vol. 88, No. 2, 25 Jan. 2005, pp. 241-249, and the like), glycogen phosphorylase inhibitors (such as N,N-4201, CP-368296 and the like), glucose-6-phosphatase inhibitors, fructose 1,6-bisphosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., *Current Science*, Vol. 88, No. 2, 25 Jan. 2005, pp. 241-249, and the like), incretin mimetics (such as exenatide and the like), glucagon receptor antagonists (such as BAY-27-9955, N,N-2501, NNC-92-1687 and the like), glucagon-like peptide-1 (GLP-1), GLP-1 analogs (such as liraglutide, CJC-1131, AVE-0100 and the like), GLP-1 receptor agonists (such as AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with compounds of the present invention include aldose reductase inhibitors (such as epalrestat, imirestat, tolrestat, minalrestat, ponalrestat, zopolrestat, fidarestat, ascorbyl gamolenate, ADN-138, BAL-ARI8, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation end-products (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocarnitine, ST-261 and the like).

Examples of antihyperuricemic agents suitable for use in combination with compounds of the present invention include uric acid synthesis inhibitors (such as allopurinol, oxypurinol and the like), uricosuric agents (such as probenecid, sulfinpyrazone, benzbromarone and the like) and urinary alkalinizers (such as sodium hydrogen carbonate, potassium citrate, sodium citrate and the like).

Examples of lipid-lowering/lipid-modulating agents suitable for use in combination with compounds of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506,219; 4,686,237; 4,647,576; 4,613,610; 4,499,289 and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157 and the like), PPAR-alpha agonists (such as GlaxoSmithKline 590735 and the like), PPAR-delta agonists (such as GlaxoSinithKline 501516 and the like), acyl-coenzyme A:cholesterol acyltransferase inhibitors (such as avasimibe, eflucimibe, eldacimibe, lecimibide, NTE-122, MCC-147, PD-132301-2, C1-1101, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-C8-434, CI-976, RP-64477, F-1394, CS-505, CL-283546, YM-17E, 447C88, YM-750, E-5324, KW-3033, HL-004 and the like), probucol, thyroid hormone receptor agonists (such as liothyronine, levothyroxine, KB-2611, GC-1 and the like), cholesterol absorption inhibitors (such as ezetimibe, SCH48461 and the like), lipoprotein-associated phospholipase A2 inhibitors (such as rilapladib, darapladib and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707 and the like), low density lipoprotein receptor activators (such as LY295427, MD-700 and the like), lipoxygenase inhibitors (such as compounds described in WO 97/12615, WO 97/12613, WO 96/38144 and the like), carnitine palmitoyl-transferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721 and the like), nicotinic acid derivatives (such as acipimox, nicotinic acid, ricotinamide, nicomol, niceritrol, nicorandil and the like), bile acid sequestrants (such as colestipol, cholestyramine, colestilan, colesevelam, GT-102-279 and the like), sodium/bile acid cotransporter inhibitors (such as 264W94, S-8921, SD-5613 and the like), and cholesterol ester transfer protein inhibitors (such as torcetrapib, JTT-705, PNU-107368E, SC-795, CP-529414 and the like).

Examples of anti-obesity agents suitable for use in combination with compounds of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, amineptine and the like), selective serotonin reuptake inhibitors (such as citalopram, escitalopram, fluoxetine, fluvoxamine, paroxetine, sertraline and the like), selective norepinephrine reuptake inhibitors (such as reboxetine, atomoxetine and the like), norepinephrine releasing stimulants (such as rolipram, YM-992 and the like), anorexiants (such as amphetamine, methamphetamine, dextroamphetamine, phentennine, benzphetamine, phendimetrazine, phenmetrazine, diethylpropion, mazindol, fenfluramine, dexfenfluramine, phenylpropanolamine and the like), dopamine agonists (such as ER-230, doprexin, bromocriptine mesylate and the like), $H_3$-histamine antagonists (such as impentamine, thioperamide, ciproxifan, clobenpropit, GT-2331, GT-2394, A-331440, and the like), 5-HT2c receptor agonists (such as 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, BVT.933, YM-348, IL-639, IK-264, ATH-88651, ATHX-105 and the like (see, e.g., Nilsson BM, *J. Med. Chem.* 2006, 49:4023-4034)), beta-3 adrenergic receptor agonists (such as L-796568, CGP 12177, BRL-28410, SR-58611A, ICI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like), cholecystokinin agonists (such as SR-146131, SSR-125180, BP-3.200, A-71623, FPL-15849, GI-248573, GW-7178, GI-181771, GW-7854, A-71378 and the like), antidepressant/acetylcholinesterase inhibitor combinations (such as venlafaxine/rivastigmine, seitraline/galanthamine and the like), lipase inhibitors (such as orlistat, ATL-962 and the like), anti-epileptic agents (such as topiramate, zonisamide and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814 and the like), ciliary neurotrophic factor (such as Axokine and the like), thyroid hormone receptor-beta agonists (such as KB-141, GC-1, GC-24, GB98/284425 and the like), cannabinoid CBI receptor antagonists (such as rimonabant, SR147778, SLV 319 and the like (see, e.g., Antel J et al., *J. Med. Chem.* 2006, 49:4008-4016)), melanin-concentrating hormone receptor antagonists (including GlaxoSmithKline 803430X, GlaxoSmithKline 856464, SNAP-7941, T-226296 and the like (see, e.g., Handlon A L and Zhou H, *J. Med. Chem.* 2006, 49:4017-4022)), melanocortin-4 receptor agonists (including PT-15, Ro27-3225, THIQ, NBI 55886, NBI 56297, NBI 56453, NBI 58702, NBI 58704, MB243 and the like (see, e.g., Nargund R P et al., *J. Med. Chem.* 2006, 49:4035-4043)), selective muscarinic receptor $M_1$ antagonists (such as telenzepine, pirenzepine and the like), and combinations thereof.

Examples of antihypertensive agents and agents for treating chronic heart failure, atherosclerosis or related diseases suitable for use in combination with compounds of the present invention include bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlonnethiazide, indapamide, metolazone, furosemide, bumetanide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretanide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), and antiplatelets agents (such as aspirin, clopidogrel, ticlopidine, dipyridamole, cilostazol, ethy icosapentate, sarpogrelate, dilazep, trapidil, beraprost and the like).

Furthermore, in another aspect, the invention provides for a pharmaceutical composition comprising effective amounts of a compound or mixture of compounds of Formula I, or a pharmaceutically acceptable salt or prodrug thereof, and at least one member selected from the group of therapeutic agents listed above as combination partners, in a pharmaceutically acceptable carrier.

The treatment of the present invention can be administered prophylactically to prevent or delay the onset or progression of a disease or condition (such as hyperglycemia), or therapeutically to achieve a desired effect (such as a desired level of serum glucose) for a sustained period of time.

The compounds of the present invention can be administered to a subject, e.g., a human patient, a domestic animal such as a cat or a dog, independently or together with a combination partner, in the form of their pharmaceutically acceptable salts or prodrugs, or in the form of a pharmaceutical composition where the compounds and/or combination partners are mixed with suitable carriers or excipient(s) in a therapeutically effective amount. Consequently, a compound or mixture of compounds of Formula I, or a pharmaceutically acceptable salt or prodrug thereof, and an additional active agent to be combined therewith, can be present in a single formulation, for example a capsule or tablet, or in two separate formulations, which can be the same or different, for example, in the form of a kit comprising selected numbers of doses of each agent.

The appropriate dosage of compound will vary according to the chosen route of administration and formulation of the composition, among other factors, such as patient response. The dosage can be increased or decreased over time, as required by an individual patient. A patient initially may be given a low dose, which is then increased to an efficacious dosage tolerable to the patient. Typically, a useful dosage for adults may be from 1 to 2000 mg, preferably 1 to 200 mg, when administered by oral route, and from 0.1 to 100 mg, preferably 1 to 30 mg, when administered by intravenous route, in each case administered from 1 to 4 times per day. When a compound of the invention is administered in combination with another therapeutic agent, a useful dosage of the combination partner may be from 20% to 100% of the normally recommended dose.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The invention will be described in greater detail by way of specific examples.

EXAMPLES

The following examples are offered for illustrative purposes, and are not intended to limit the invention in any manner. Those of skill in the art will readily recognize a variety of noncritical parameters which can be changed or modified to yield essentially the same results.

The names of compounds shown in the following examples were derived from the structures shown using the Cambridge-Soft Struct=Name algorithm as implemented in ChemDraw Ultra version 10.0. Unless otherwise specified, the structures of compounds synthesized in the examples below were confirmed using the following procedures:

(1) Gas chromatography mass spectra with electrospray ionization (MS ESI) were obtained with an Agilent 5973N mass spectrometer equipped with an Agilent 6890 gas chromatograph with an HP-5 MS column (0.25 μm coating; 30 m×0.25 mm). The ion source was maintained at 230° C. and spectra were scanned from 25-500 amu at 3.09 sec per scan.

(2) High pressure liquid chromatography mass spectra (LC-MS) were obtained using Finnigan Surveyor HPLC equipped with a quaternary pump, a variable wavelength detector set at 254 nm, an XB-C18 column (4.6×50 mm, 5 μm), and a Finnigan LCQ ion trap mass spectrometer with electrospray ionization. Spectra were scanned from 80-2000 amu using a variable ion time according to the number of ions in the source. The eluents were B: acetonitrile and D: water. Gradient elution from 10% B to 90% in 8 min at a flow rate of 1.0 mL/min is used with a final hold at 90% B of 7 min. Total run time was 15 min.

(3) Routine one-dimensional NMR spectroscopy is performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$, 3.30 ppm for $CD_3OD$, 5.32 ppm for $CD_2Cl_2$ and 7.26 ppm for $CDCl_3$ for $^1H$ spectra.

Example 1

Figure 9:
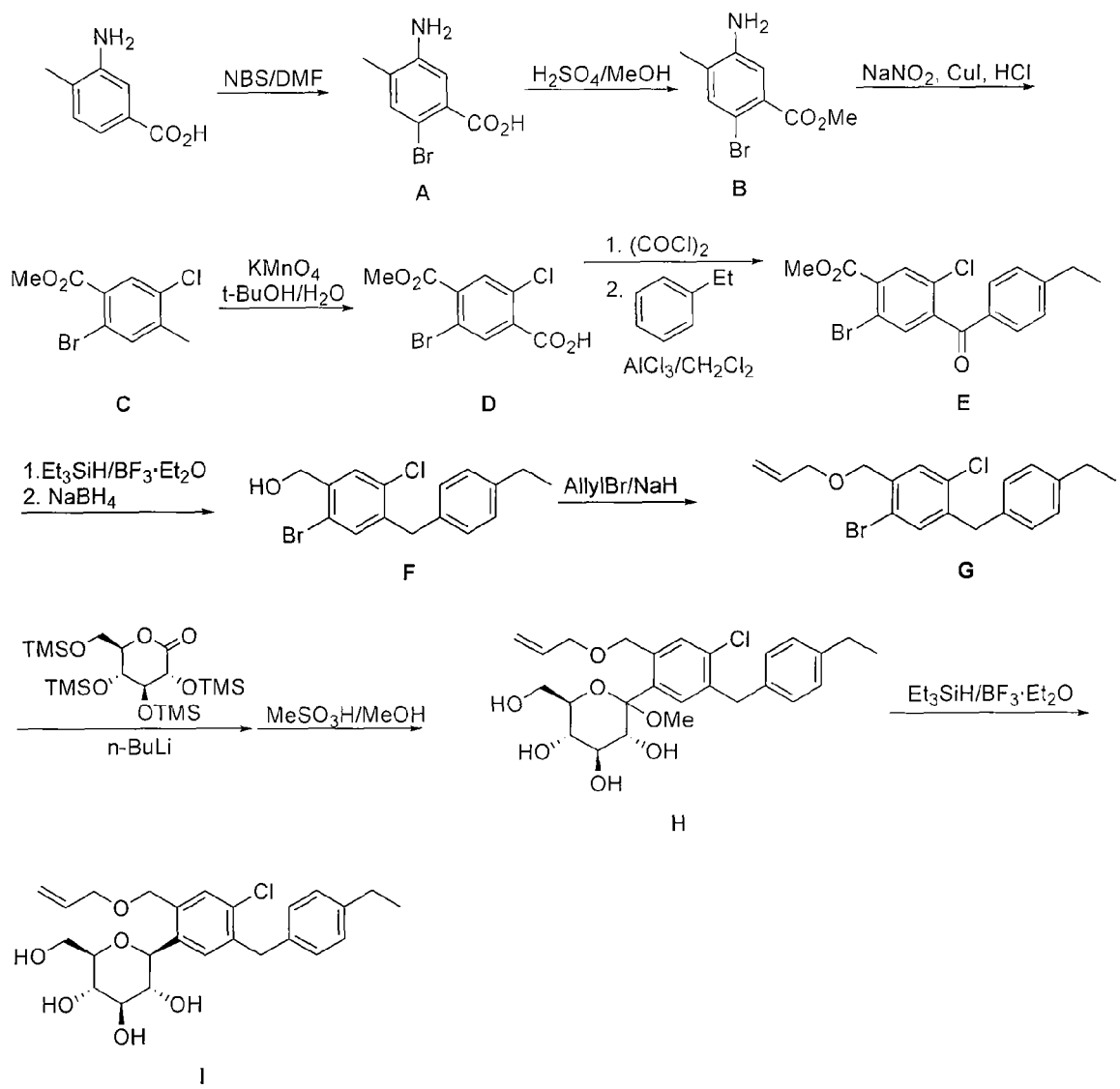
FIGS. 9-15 provide more specific synthesis schemes for compounds in the Examples below.

This example illustrates the preparation of compound I according to the approach provided in FIG. 9. The general method is applicable to other compounds of the present invention.

Preparation of 5-amino-2-bromo-4-methylbenzoic acid (Intermediate A)

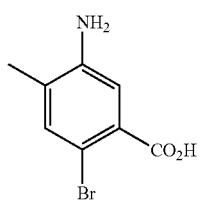

To a cooled solution (5° C.) of 3-amino-4-methylbenzoic acid (412.2 g, 2.72 mole) in DMF (2.2 L) was added N-bromosuccinimide (495.1 g, 2.78 mole) in small portions at such a rate that the reaction mixture temperature was kept below 15° C. After being stirred for one hour, the reaction mixture was poured onto ice water (1.2 L) with stirring. The solid that formed was filtered, and the filter cake was washed with ice water (3×2 L) and then dried at 60° C. to give a pink solid. Yield: 546 g (87%). $^1$H-NMR (DMSO-d6, 300 MHz): δ 7.20 (s, 1H), 7.04 (s, 1H), 2.05 (s, 3H).

Preparation of methyl 5-amino-2-bromo-4-methylbenzoate (Intermediate B)

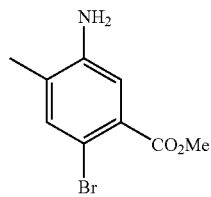

To a cooled solution (5° C.) of 5-amino-2-bromo-4-methylbenzoic acid (100.0 g, 0.434 mmol) in anhydrous methanol (1.6 L) was added dropwise thionyl chloride (112.4 g). The reaction mixture was refluxed and monitored by TLC. After refluxing for 6 h, the reaction was complete. The reaction solution was concentrated under reduced pressure. The residue was diluted with ice water (1.2 L) and neutralized with 5% $NaHCO_3$ to pH 7.5. The aqueous layer was extracted with EtOAc (3×600 mL), and the combined organic layers were washed with brine (2×500 mL), and dried over anhydrous $Na_2SO_4$. Concentration under reduced pressure provided the title compound as a pale solid. Yield: 99%. $^1$H-NMR (DMSO-d$_6$, 300 MHz): δ 7.25 (s, 1H), 7.14 (s, 1H), 3.30 (s, 3H), 2.15 (s, 3H); MS ESI (m/z) 244 [M+1]$^+$, calc. 243.

Preparation of methyl 2-bromo-5-chloro-4-methylbenzoate (Intermediate C)

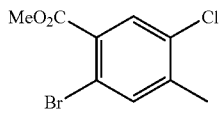

To a cooled solution (15° C.) of methyl 5-amino-2-bromo-4-methylbenzoate (122 g, 0.5 mol) in 1,4-dioxane (633 mL), was added conc. hydrochloric acid (550 mL). After the mixture was cooled to 5° C., a solution of sodium nitrite (35.53 g, 0.515 mol) in 83 mL of $H_2O$ was added dropwise at such a rate that the reaction temperature was kept below 0° C. After being stirred at 0° C. for 2 h, the reaction mixture was added slowly to a flask containing copper (I) chloride (59.4 g, 0.6 mol) and conc. hydrochloric acid (275 mL). It was stirred for 40 min, at which time TLC demonstrated that the reaction was complete. The reaction mixture was poured over ice water (2 L) and then filtered. The filter cake was dissolved in EtOAc (1.5 L). The organic layer was washed with brine (3×500 mL) and then dried over anhydrous $Na_2SO_4$ Concentration under reduced pressure provided the title compound as light yellow crystals. Yield: 120 g (92.6%). $^1$H-NMR (CDCl$_3$, 300 MHz): δ 7.82 (s, 1H), 7.54 (s, 1H), 3.92 (s, 3H), 2.38 (s, 3H); MS ESI (m/z) 262 (M)$^+$, calc. 262.

Preparation of 5-bromo-2-chloro-4-(methoxycarbonyl)benzoic acid (Intermediate D)

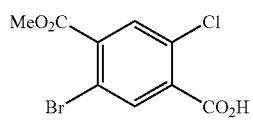

A mixture of methyl 2-bromo-5-chloro-4-methylbenzoate (39.53 g, 0.15 mol), 18-Crown-6 (3.95 g), tert-butyl alcohol (350 mL), and water (750 mL) was combined together with mechanical stirring. The reaction mixture was heated to reflux and monitored by TLC. After refluxing overnight, the reaction was cooled to 55° C. and filtered. The filter cake was washed with hot water (2×100 mL, 50° C.). The filtrate was neutralized with 18% hydrochloric acid to pH 1 and stored in a refrigerator (0~5° C.) for 3 h. It was filtered, and then washed with ice water (2×50 mL) and petroleum ether (2×50 mL). The filter cake was dried under vacuum to give the title compound as a white crystalline solid. Yield: 32.1 g (73%). $^1$H-NMR (DMSO-d$_6$, 300 MHz): δ 8.10 (s, 1H), 7.89 (s, 1H), 3.86 (s, 3H).

Preparation of methyl 2-bromo-5-chloro-4-(4-ethylbenzoyl)benzoate (Intermediate E)

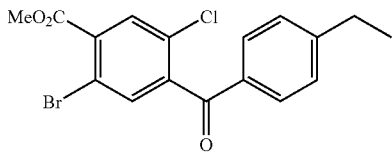

To a solution of 5-bromo-2-chloro-4-(methoxycarbonyl) benzoic acid (1.21 g, 4.15 mmol) in dry dichloromethane (22.5 mL) was added dropwise oxalyl chloride (0.43 mL, 4.96 mmol) followed by N,N-dimethylformamide (1 mL). After being stirred for 2 h at room temperature, the reaction mixture was evaporated and the residue was dissolved in dry dichloromethane (20 mL) at room temperature under agron. After cooling to −5° C., ethylbenzene (0.46 g, 4.35 mmol) was added. Then AlCl$_3$ (1.72 g, 12.8 mmol) was added portionwise and the reaction temperature was kept between −5° C. and 0° C. After being stirred at the same temperature for two hours, the reaction mixture was poured onto ice water and extracted with dichloromethane (100 mL). The combined organic layers were washed with 1 M HCl (60 mL), water (30 mL) and brine (60 mL), and dried over anhydrous Na$_2$SO$_4$ Concentration under reduced pressure provided the title compound as a yellow solid. Yield: 1.37 g (87%). $^1$H-NMR (CDCl$_3$, 300 MHz): δ 7.89 (s, 1H), 7.72 (d, J=2.0 Hz, 1H), 7.70 (d, J=2.0 Hz, 1H), 7.64 (s, 1H), 7.33 (s, 1H), 7.30 (s, 1H), 3.98 (s, 3H), 2.70 (q, J=7.8 Hz, 2H), 1.27 (t, J=7.8 Hz, 3H).

Preparation of (2-bromo-5-chloro-4-(4-ethylbenzyl) phenyl)methanol (Intermediate F)

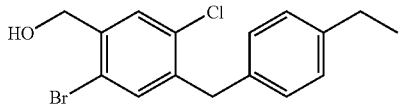

To a solution of methyl 2-bromo-5-chloro-4-(4-ethylbenzoyl)benzoate (7.64 g, 20 mmol) in 2,2,2-trifluoroacetic acid (38 mL) was added triethylsilane (5.88 mL, 40 mmol) under argon. After it was stirred for 10 min at room temperature, trifluoromethanesulfonic acid (0.1 mL) was added. The reaction temperature was raised from 26° C. to reflux. After stirring for 2 h, TLC (PE:EtOAc=6:1, R$_f$=0.7) showed the reaction was complete. The reaction mixture was evaporated and the residue was dissolved in EtOAc (150 mL). The organic layer was washed 2× with H$_2$O, 2× with NaHCO$_3$, and 2× with brine, and then dried over anhydrous Na$_2$SO$_4$ Concentration under reduced pressure provided the title compound as a white solid. Yield: 7.2 g (100%). $^1$H-NMR (CDCl$_3$, 300 MHz) δ 7.85 (s, 1H), 7.44 (s, 1H), 7.17 (s, 1H), 7.14 (s, 1H), 7.10 (s, 1H), 7.07 (s, 1H), 4.05 (s, 2H), 3.92 (s, 3H), 2.63 (q, J=7.8 Hz, 2H), 1.24 (t, J=7.8 Hz, 3H).

Preparation of 1-(allyloxymethyl)-2-bromo-5-chloro-4-(4-ethylbenzyl)benzene (Intermediate G)

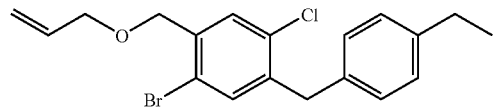

To a solution of (2-bromo-5-chloro-4-(4-ethylbenzyl)phenyl)methanol (3.4 g, 10 mmol) in DMF (50 mL) was added NaH (0.8 g, 20 mmol, 60% in miner oil) in portions at −5° C. After being stirred for 1 h at the same temperature, the reaction mixture was cooled to −10° C., TBAI (0.37 g, 1 mmol) and a solution of allyl bromide (1.45 g, 12 mmol) in DMF (10 mL) was added. The reaction mixture was stirred for another 1 h prior to quenching by ice water and extracted 3× with EtOAc. The combined organic layers were washed with brine and then dried over Na$_2$SO$_4$. Concentration gave the crude product, which was purified by silica column chromatography (elution with PE:EtOAc=10:1) to afford the title compound (3.22 g, yield 84.8%).

Preparation of (2S,3R,4S,5S,6R)-2-(2-(allyloxymethyl)-4-chloro-5-(4-ethylbenzyl)phenyl)-6-(hydroxymethyl)-2-methoxytetrahydro-2H-pyran-3,4,5-triol (Intermediate H)

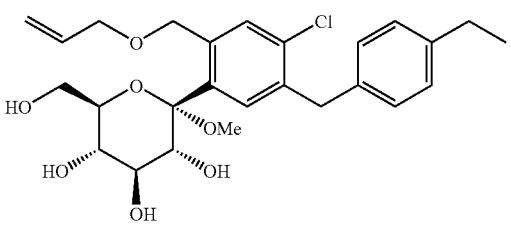

To a solution of 1-(allyloxymethyl)-2-bromo-5-chloro-4-(4-ethylbenzyl)benzene in dry THF:toluene (1:2, 2.4 mL) was added n-BuLi (0.3 mL, 2.5 M in hexane) dropwise under argon. After it was stirred for 1 h, a cooled solution (−70° C.) of (3R,4S,5R,6R)-3,4,5-tris(trimethylsilyloxy)-6-((trimethylsilyloxy)methyl)-tetrahydropyran-2-one in dry toluene (1.8 mL) was added dropwise to the reaction mixture. After being stirred for 3 h, the reaction was quenched by addition of ice water and extracted with EtOAc. The combined organic layers were washed 2× with water, 2× with brine, and then dried over Na$_2$SO$_4$. Concentration gave a yellow oil, which was dissolved in 20 mL of methanol, and methanesulfonic acid in 5 mL of methanol was added. The reaction mixture was stirred over 50 h under argon prior to being quenched by addition of satd NaHCO$_3$ to pH 7.5. Concentration gave a residue, which was purified by preparative TLC to yield 14 mg of title compound as a white solid. $^1$H-NMR (CD$_3$OD, 400 MHz) δ 7.48 (s, 1H), 7.36 (s, 1H), 7.03 (s, 4H), 5.93-5.87 (m, 1H), 5.24 (dd, J=17.2 Hz, 1.6 Hz, 1H), 5.11 (dd, J=1.6 Hz, 10.4 Hz, 1H), 4.70 (m, 3H), 4.06-3.89 (m, 4H), 3.82 (dd, J=2.4 Hz, 12.4 Hz, 1H), 3.71-3.62 (m, 2H), 3.50-3.46 (m, 1H), 3.26-3.22 (m, 1H), 3.00 (s, 3H), 2.78-2.74 (m, 1H), 1.12 (d, J=7.2 Hz, 6H); LC-MS (m/z) 493 [(M+1)$^+$].

Preparation of (2S,3R,4R,5S,6R)-2-(2-(allyloxymethyl)-4-chloro-5-(4-ethylbenzyl)phenyl)-6-(hydroxymethyl)tetrahydro-2H-pyran-3,4,5-triol (Compound I)

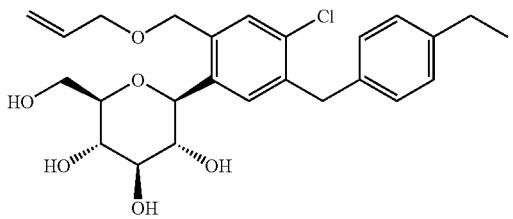

To a cooled solution (−15° C.) of (3R,4S,5S,6R)-2-(2-(allyloxymethyl)-4-chloro-5-(4-ethylbenzyl)phenyl)-6-(hydroxymethyl)-2-methoxytetrahydro-2H-pyran-3,4,5-triol in 1:1 CH$_2$Cl$_2$:CH$_3$CN was added triethylsilane followed by addition of BF$_3$.Et$_2$O at a rate such that the temperature was maintained between −15° C. and −10° C. under argon. The reaction mixture was stirred for 4 h prior to being quenched by satd NaHCO$_3$. It was evaporated and the residue was partitioned between EtOAc and water. The organic layer was separated, washed 2× with brine and dried over Na$_2$SO$_4$. Concentration gave a residue, which was purified by preparative TLC (EtOAc:MeOH=20:1, R$_f$=0.6) to yield 58 mg of title compound as a white solid. 1H-NMR (CD$_3$OD, 400 MHz) δ 7.46 (s, 1H), 7.35 (s, 1H), 7.04 (s, 4H), 5.92-5.86 (m, 1H), 5.25 (dd, J=17.2 Hz, 1.6 Hz, 1H), 5.09 (dd, J=10.4 Hz, 1.6 Hz, 1H), 4.68 (m, 3H), 4.48 (d, J=9.2 Hz, 1H), 4.05-3.86 (m, 4H), 3.83 (dd, J=12.4 Hz, 2.4 Hz, 1H), 3.71-3.62 (m, 2H), 3.50- 3.46 (m, 1H), 3.26-3.22 (m, 1H), 2.78-2.74 (m, 1H), 1.13 (d, J=7.2 Hz, 6H); LC-MS (m/z) 463 [(M+1)+].

Compound I was repurified by the following steps.

Preparation of (2R,3R,4R,5S,6S)-2-(acetoxymethyl)-6-(2-(allyloxymethyl)-4-chloro-5-(4-ethylbenzyl)phenyl)tetrahydro-2H-pyran-3,4,5-triyl triacetate (Intermediate J)

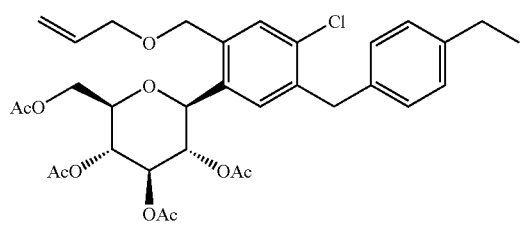

To a solution of (2S,3R,4R,5S,6R)-2-(2-(allyloxymethyl)-4-chloro-5-(4-ethylbenzyl)phenyl)-6-(hydroxymethyl)tetrahydro-2H-pyran-3,4,5-triol (1.2 g, 2.6 mmol) in dry dichloromethane (18 mL), was added pyridine (2.1 mL, 26 mmol) followed by acetic anhydride (2.7 mL, 28.6 mmol). After it was stirred for 20 min, DMAP (31.7 mg) was added and the reaction mixture was stirred overnight under argon. The reaction was quenched by addition of 10 mL of water and extracted 2× with CH$_2$Cl$_2$. The combined organic layers were washed 2× with 1 M HCl, 2× with brine, and then dried over Na$_2$SO$_4$. Concentration gave a residue, which was purified by preparative TLC (PE:EtOAc=3:1, R$_f$=0.6) to yield 1.1 g of title compound as a white solid. LC-MS (m/z) 631 [(M+1)$^+$], 675 [(M+45)$^-$].

Preparation of (2S,3R,4R,5S,6R)-2-(2-(allyloxymethyl)-4-chloro-5-(4-ethylbenzyl)phenyl)-6-(hydroxymethyl)tetrahydro-2H-pyran-3,4,5-triol (Compound I)

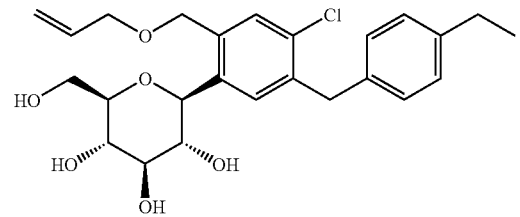

To (2R,3R,4R,5S,6S)-2-(acetoxymethyl)-6-(2-(allyloxymethyl)-4-chloro-5-(4-ethylbenzyl)phenyl)tetrahydro-2H-pyran-3,4,5-triyl triacetate (246 mg, 0.39 mmol) in THF:MeOH:H$_2$O (2:3:1, 6 mL) was added LiOH.H$_2$O (16.4 mg, 0.47 mmol). After being stirred for 12 h at room temperature, the reaction mixture was concentrated and the residue was dissolved in 20 mL of EtOAc. The organic layer was washed with brine and dried over Na$_2$SO$_4$ Concentration gave a residue, which was purified by preparative TLC (PE:EtOAc:MeOH=8:80:1, R$_f$=0.5) to yield 132 mg of title compound as a white solid. $^1$H-NMR (CD$_3$OD, 400 MHz) δ 7.48 (s, 1H), 7.42 (s, 1H), 7.11 (s, 4H), 5.93-5.87 (m, 1H), 5.24 (dd, J=17.2 Hz, 1.6 Hz, 1H), 5.11 (dd, J=1.6 Hz, 10.4 Hz, 1H), 4.85 (d, J=12.0 Hz, 1H), 4.62 (d, J=12.0 Hz, 1H), 4.51 (d, J=9.2 Hz, 1H), 4.23 (s, 2H), 4.10 (d, J=14.8 Hz, 1H), 4.05 (d, J=14.8 Hz, 1H), 3.88 (d, J=12.4 Hz, 1H), 3.71-3.67 (m, 1H), 3.52-3.41 (m, 4H), 2.60 (q, J=7.6 Hz, 2H), 1.21 (t, J=7.6 Hz, 3H); LC-MS (m/z) 463 [(M+1)$^+$], 507 [(M+45)$^-$].

Example 2

Preparation of 1-(5-chloro-4-(4-ethylbenzyl)-2-((2S, 3R,4R,5S,6R)-3,4,5-trihydroxy-6-(hydroxymethyl) tetrahydro-2H-pyran-2-yl)benzyloxy)propan-2-one (Compound K)

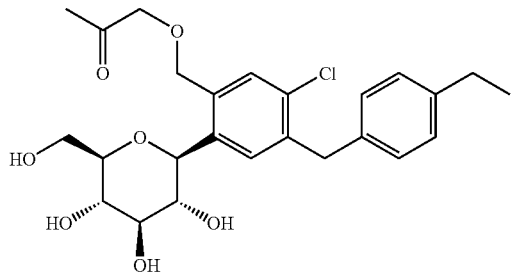

To a stirred solution of (2R,3R,4R,5S,6S)-2-(acetoxymethyl)-6-(4-chloro-5-(4-ethylbenzyl)-2-((2-oxopropoxy)methyl)phenyl)tetrahydro-2H-pyran-3,4,5-triyl triacetate (36.8 g, 0.057 mmol) (prepared from intermediate J using a Wacker oxidation as described for the preparation of intermediate T-1 below) in THF:MeOH:H$_2$O (2:3:1, 1.2 mL) was added lithium hydroxide (3.71 mg). The reaction was stirred overnight at 20° C. The volatiles were removed and the residue was dissolved in EtOAc (20 mL), washed 1× with brine, 1× with brine containing 2 mL of 5% aqueous KHSO$_4$ and dried over Na$_2$SO$_4$. Concentration gave 16 mg of pure product as a white solid. $^1$H-NMR (CD$_3$OD, 300 MHz) δ 7.47 (s, 1H), 7.44 (s, 1H), 7.08 (s, 4H), 4.80 (d, J=12.3 Hz, 1H), 4.55 (d, J=9.6 Hz, 1H), 4.22 (s, 2H), 4.10 (d, J=14.8 Hz, 1H), 4.05 (d, J=14.8 Hz, 1H), 3.85 (dd, J=11.7 Hz, 2.1 Hz, 1H), 387-3.83 (m, 1H), 3.68-3.63 (m, 1H), 3.50-3.36 (m, 4H), 2.58 (q, J=7.8 Hz, 2H), 2.12 (s, 3H), 1.19 (t, J=7.8 Hz, 3H); LC-MS (m/z) 479 [(M+1)$^+$], 523 [(M+45)$^-$].

Example 3

Preparation of (2S,3R,4R,5S,6R)-2-(4-chloro-2-((2, 3-dihydroxypropoxy)methyl)-5-(4-ethylbenzyl)phenyl)-6-(hydroxymethyl)tetrahydro-2H-pyran-3,4,5-triol (Compound L)

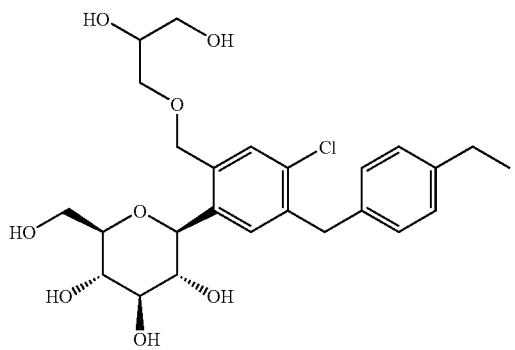

To a stirred solution of (2R,3R,4R,5S,6S)-2-(acetoxymethyl)-6-(4-chloro-2-((2,3-dihydroxypropoxy)methyl)-5-(4-ethylbenzyl)phenyl)tetrahydro-2H-pyran-3,4,5-triyl triacetate (50 mg, 0.076 mmol) (prepared from intermediate J using a Sharpless dihydroxylation) in THF:MeOH:H$_2$O (2:3:1, 1.2 mL) was added lithium hydroxide (3.71 mg). The reaction was stirred overnight at 20° C. The volatiles were removed and the residue was dissolved in EtOAc (20 mL), washed 1× with brine, 1× with brine containing 2 mL of 5% aqueous KHSO$_4$ and dried over Na$_2$SO$_4$. Concentration gave 3.5 mg of pure product as a white solid. $^1$H-NMR (CD$_3$OD, 300 MHz) δ 7.45 (s, 1H), 7.43 (s, 1H), 7.08 (s, 4H), 4.75-4.70 (m, 2H), 4.60-4.45 (m, 2H), 4.10 (d, J=14.8 Hz, 1H), 4.05 (d, J=14.8 Hz, 1H), 3.93-3.83 (m, 2H), 3.87-3.77 (m, 2H), 3.66-3.36 (m, 7H), 2.60 (q, J=7.8 Hz, 2H), 1.21 (t, J=7.8 Hz, 3H), 1.15 (d, J=7.8 Hz, 3H); LC-MS (m/z) 497 [(M+1)$^+$], 541 [(M+45)$^-$].

Example 4

Preparation of (2S,3R,4R,5S,6R)-2-(4-chloro-5-(4-ethylbenzyl)-2-((2-hydroxypropoxy)methyl)phenyl)-6-(hydroxymethyl)tetrahydro-2H-pyran-3,4,5-triol (Compound M)

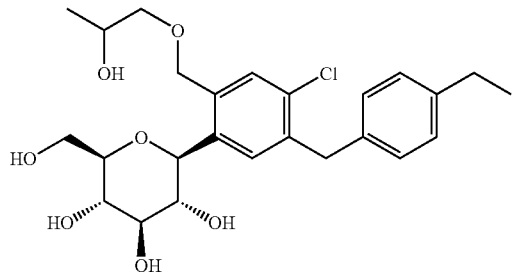

To a solution of 1-(5-chloro-4-(4-ethylbenzyl)-2-((2S,3R, 4R,5S,6R)-3,4,5-trihydroxy-6-(hydroxymethyl)tetrahydro-2H-pyran-2-yl)benzyloxy)propan-2-one (compound K) (3.7 mg, 0.0077 mmol) in dry THF (0.5 mL) was added NaBH$_4$ (1.76 mg, 0.0045 mmol) with stirring under argon at room temperature. After the mixture was stirred for 20 min, anhydrous methanol was added dropwise, and the resulting mixture was stirred at 20° C. for 2 h, then quenched by addition of sat. NH$_4$Cl. The mixture was extracted with EtOAc and the combined organic layers were washed with water, brine, dried over Na$_2$SO$_4$, filtered and concentrated to provide the crude product, which was purified by preparative TLC to yield 2.5 mg of the product. $^1$H-NMR (CD$_3$OD, 300 MHz) δ 7.45 (s, 1H), 7.43 (s, 1H), 7.08 (s, 4H), 4.75-4.56 (m, 1H), 4.47 (dd, J=9.3 Hz, 3.3 Hz, 1H), 4.10 (d, J=14.8 Hz, 1H), 4.05 (d, J=14.8 Hz, 1H), 3.93-3.83 (m, 2H), 3.68-3.66 (m, 1H), 3.47-3.37 (m, 6H), 2.60 (q, J=7.8 Hz, 2H), 1.21 (t, J=7.8 Hz, 3H), 1.15 (d, J=7.8 Hz, 3H); LC-MS (m/z) 481 [(M+1)$^+$], 525 [(M+45)$^-$].

Example 5

Preparation of (2S,3R,4R,5S,6R)-2-(4-chloro-5-(4-ethylbenzyl)-2-((prop-2-ynyloxy)methyl)phenyl)-6-(hydroxymethyl)tetrahydro-2H-pyran-3,4,5-triol (Compound N)

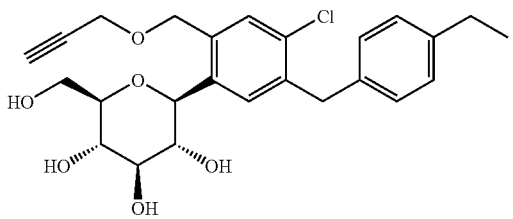

To a solution of (2S,3R,4R,5S,6R)-2-(4-chloro-2-((2,3-dibromopropoxy)methyl)-5-(4-ethylbenzyl)phenyl)-6-(hydroxymethyl)tetrahydro-2H-pyran-3,4,5-triol (53.3 mg, 0.086 mmol) (prepared by bromination of compound I) in anhydrous ethanol (1.0 mL) was added potassium hydroxide (10.6 mg). The reaction mixture was refluxed and monitored by LC-MS. After 6 h, LC-MS showed the reaction was complete. The reaction mixture was concentrated and the residue was partitioned between EtOAc and water, the organic layer was separated, washed 2× with 1N HCl, 3× with brine, and dried over $Na_2SO_4$. Concentration gave the crude product, which was purified by preparative HPLC to yield 21 mg of title compound as a white solid. $^1$H-NMR ($CD_3OD$, 400 MHz) δ 7.48 (s, 1H), 7.42 (s, 1H), 7.11 (s, 4H), 4.85 (d, J=12.0 Hz, 1H), 4.62 (d, J=12.0 Hz, 1H), 4.51 (d, J=9.2 Hz, 1H), 4.23 (s, 2H), 4.10 (d, J=14.8 Hz, 1H), 4.05 (d, J=14.8 Hz, 1H), 3.88 (d, J=12.4 Hz, 1H), 3.71-3.67 (m, 1H), 3.52-3.41 (m, 4H), 2.94 (s, 1H), 2.60 (q, J=7.6 Hz, 2H), 1.21 (t, J=7.6 Hz, 3H); LC-MS (m/z) 461 [(M+1)$^+$], 515 [(M+45)$^-$].

Example 6

Figure 10:
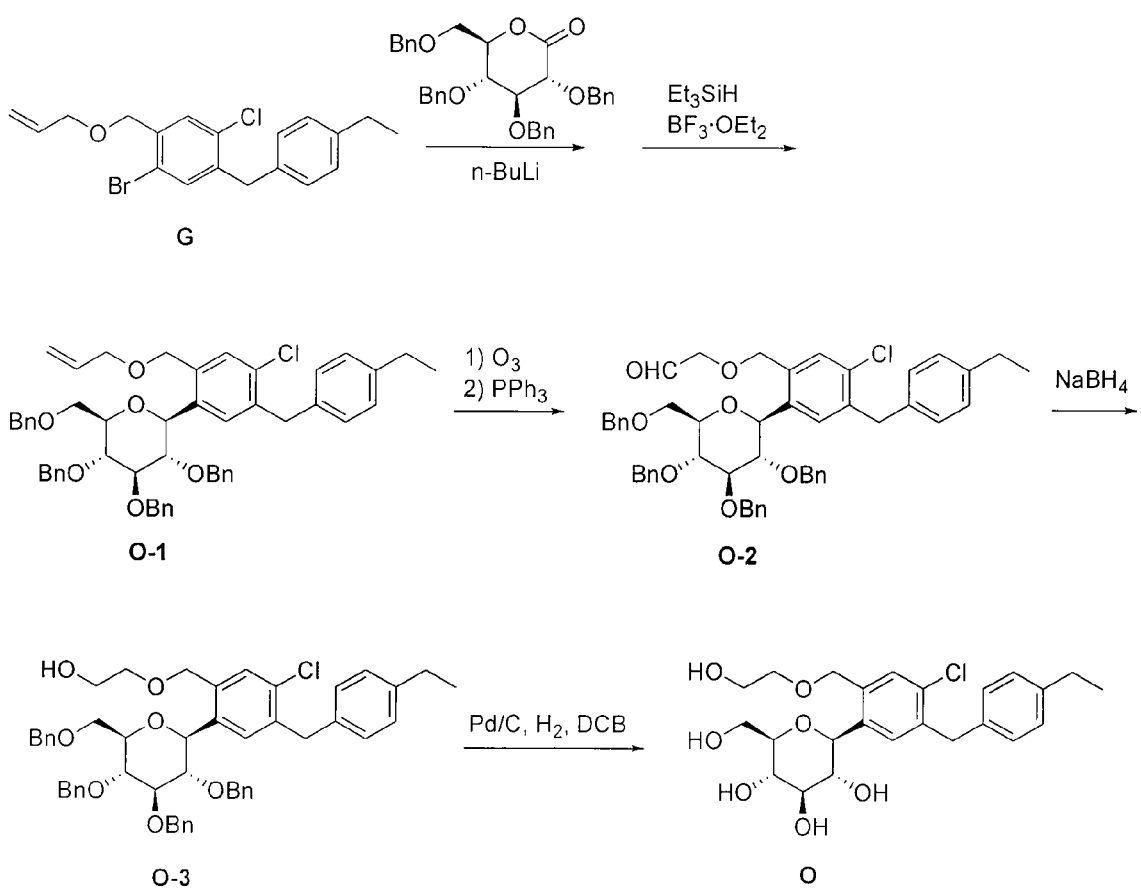

This example illustrates the preparation of compound O according to the approach provided in FIG. 10. The general method is applicable to other compounds of the present invention.

Preparation of (2S,3S,4R,5R,6R)-2-(2-(allyloxymethyl)-4-chloro-5-(4-ethylbenzyl)phenyl)-3,4,5-tris(benzyloxy)-6-(benzyloxymethyl)tetrahydro-2H-pyran (Intermediate O-1)

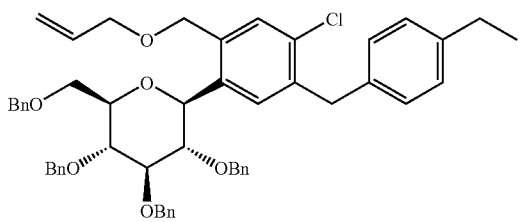

n-BuLi (3.7 mL, 9.4 mmol, 2.5M in hexane) was added into a solution of 1-(allyloxymethyl)-2-bromo-5-chloro-4-(4-ethylbenzyl)benzene (intermediate G) (3.22 g, 8.5 mmol) in anhydrous THF (30 mL) at −78° C. under argon, and stirred for 2 h at the same temperature. A solution of (3R,4S,5R,6R)-3,4,5-tris(benzyloxy)-6-(benzyloxymethyl)tetrahydro-2H-pyran-2-one (6.87 g, 2.8 mmol) in anhydrous THF (20 mL) at −78° C. was slowly added dropwise into the reaction mixture at −78° C. under argon and stirring was continued for another 2 h. The reaction mixture was quenched by addition of saturated $NH_4Cl$ (10 mL), extracted with ethyl acetate (100 mL×3), and the combined extracts were then dried over $Na_2SO_4$. The dried extracts were filtered and evaporated to dryness. Without further purification, $BF_3 \cdot Et_2O$ (1.81 g, 12.8 mmol) and $Et_3SiH$ (1.48 g, 12.8 mmol) were added to the solution of the residue in $CH_3CN$ (30 mL) at −40° C., and the mixture was stirred for 2 h. The reaction mixture was evaporated to dryness. Water was poured into the residue and the aqueous mixture was extracted with ethyl acetate (100 mL×3), dried over $Na_2SO_4$, and evaporated to dryness. The residue was purified by silica column chromatography (elution PE:EtOAc=40:1), and afforded (2S,3S,4R,5R,6R)-2-(2-(allyloxymethyl)-4-chloro-5-(4-ethylbenzyl)phenyl)-3,4,5-tris(benzyloxy)-6-(benzyloxymethyl)tetrahydro-2H-pyran (intermediate O-1) (1.96 g, 2.4 mmol, yield 28.2%).

Preparation of 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)acetaldehyde (Intermediate O-2)

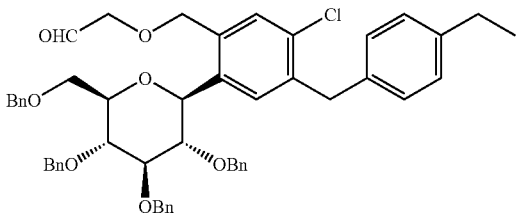

$O_3$ was bubbled into the solution of (2S,3S,4R,5R,6R)-2-(2-(allyloxymethyl)-4-chloro-5-(4-ethylbenzyl)phenyl)-3,4,5-tris(benzyloxy)-6-(benzyloxymethyl)tetrahydro-2H-pyran (intermediate O-1) (200 mg, 0.24 mmol) in anhydrous $CH_2Cl_2$ at −78° C. for 5 min, and then argon was bubbled into the reaction solution for another 30 min, the solution of $PPh_3$ (191 mg, 0.72 mmol) in $CH_2Cl_2$ was added, and the mixture was warmed to room temperature, stirred for another 30 min, and evaporated to dryness. The residue was purified by preparative TLC, which afforded 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)acetaldehyde (intermediate O-2) (152 mg, 0.18 mmol, yield 75%). $^1$H-NMR ($CDCl_3$, 300 Hz) δ 1.759 (t, J=7.5 Hz, 3H), 2.561 (dd, J=7.5 Hz, 2H), 3.709 (m, 2H), 3.774 (m, 5H), 3.955 (m, 5H), 4.046 (dd, J=18, 15 Hz, 2H), 4.433 (m, 5H), 4.518 (m, 1H), 4.873 (m, 4H), 6.841 (m, 2H), 7.044 (m, 4H), 7.215 (m, 6H), 7.287 (m, 13H), 9.568 (s, 1H).

Preparation of 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)ethanol (Intermediate O-3)

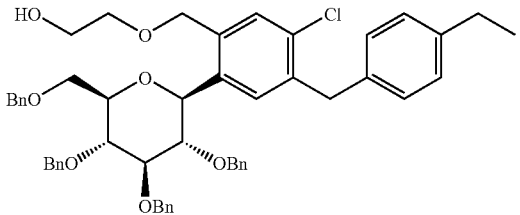

NaBH₄ (13 mg, 0.34 mmol) was added into a solution of 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)acetaldehyde (intermediate O-2) (140 mg, 0.17 mmol) in THF (10 mL) and stirred for 1.5 h. The reaction mixture was quenched by MeOH (2 mL), then evaporated to dryness. The residue was purified by preparative TLC, which afforded 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)ethanol (intermediate O-3) (135 mg, 0.169 mmol, yield 96.2%).

Preparation of (2S,3R,4R,5S,6R)-2-(4-chloro-5-(4-ethylbenzyl)-2-((2-hydroxyethoxy)methyl)phenyl)-6-(hydroxymethyl)tetrahydro-2H-pyran-3,4,5-triol (Compound O)

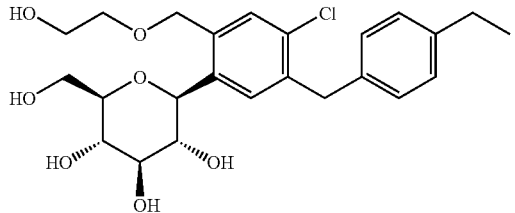

To a solution of 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)ethanol (intermediate O-3) (50 mg, 0.06 mmol) in THF:CH₃OH=2:1 (3 mL) was added 1,2-dichlorobenzene (17.4 mg, 0.12 mmol) and Pd/C (50 mg, 10% Pd/C), and the mixture was stirred 3 h under H₂ atmosphere at room temperature (about 25° C.). The reaction was monitored by LC-MS to confirm completion, the mixture was filtered, and the filtrate was evaporated to dryness. The residue was purified by preparative HPLC to give compound O (20 mg, 0.043 mmol, yield 71.5%). ¹H-NMR (CD₃OD, 300 MHz) δ 1.180 (t, J=7.5 Hz, 3H), 2.572 (dd, J=7.5 Hz, 2H), 3.419 (m, 4H), 3.631 (111, 5H), 3.853 (d, J=11.4 Hz, 1H), 4.046 (dd, J=18, 15 Hz, 2H), 4.469 (d, J=9 Hz, 1H), 4.597 (d, J=12.3 Hz, 1H), 4.737 (cl, J=12 Hz, 1H), 7.074 (s, 4H), 7.447 (s, 1H), 7.458 (s, 1H). MS ESI m/z (%) 467 (M+H)⁺, 933 (2M+H)⁺, 511 (M+HCOOH−H)⁻, 977 (2M+HCOOH−H)⁻.

Example 7

Preparation of (2S,3R,4R,5S,6S)-2-(4-chloro-5-(4-ethylbenzyl)-2-((2-fluoroethoxy)methyl)phenyl)-6-(fluoromethyl)tetrahydro-2H-pyran-3,4,5-triol (Compound P)

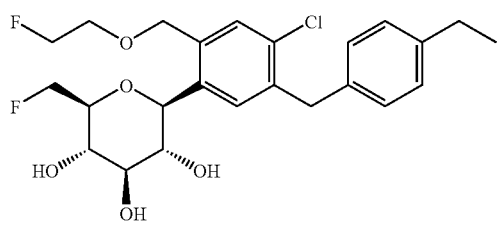

Compound P was prepared using methods analogous to those described above as will be evident to those skilled in the art. MS ESI m/z (%) 471 (M+H)⁺, 488 (M+NH₄)⁺, 515 (M+HCOOH−H)⁻, 940 (2M−H)⁻, 987 (2M+HCOOH−H)⁻. ¹H-NMR (CD₃OD, 300 MHz) δ 1.188 (t, J=7.5 Hz, 3H), 2.595 (dd, J=7.5 Hz, 2H), 3.451 (m, 3H), 3.609 (m, 1H), 3.691 (m, 1H), 3.790 (m, 1H), 4.053 (dd, J=18, 15 Hz, 2H), 4.479 (m, 3H), 4.613 (m, 3H), 4.805 (d, J=12.6 Hz, 1H), 7.084 (s, 4H), 7.382 (s, 1H), 7.429 (s, 1H).

Example 8

Preparation of (2S,3R,4R,5S,6R)-2-(4-chloro-5-(4-ethylbenzyl)-2-((oxiran-2-ylmethoxy)methyl)phenyl)-6-(hydroxymethyl)tetrahydro-2H-pyran-3,4,5-triol (Compounds Q-1 and Q-2)

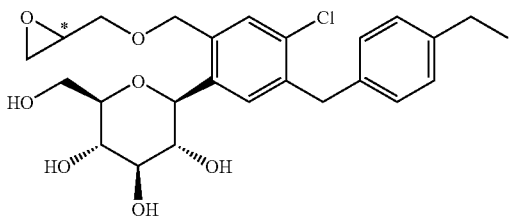

To a solution of (2S,3R,4R,5S,6R)-2-(2-(allyloxymethyl)-4-chloro-5-(4-ethylbenzyl)phenyl)-6-(hydroxymethyl)tetrahydro-2H-pyran-3,4,5-triol (463 mg, 1 mmol) in CH₂Cl₂ (2 mL) at 0° C., was added mCPBA (350 mg, 2 mmol). The mixture was heated to 40° C. and kept at that temperature overnight. Upon being cooled to room temperature, 10 mL of CH₂Cl₂ was added to dilute the solution. The solution was then washed with aqueous NaHCO₃ and brine prior to drying over Na₂SO₄. The solvent was removed under reduced pressure and purification of the resulting mixture with preparative TLC gave two isomers with undetermined absolute configurations.

Isomer Q-1: ¹H-NMR (CD₃OD, 300 MHz): δ 0.185 (3H, t, J=7.5 Hz), 2.577 (2H, dd, J=7.5 Hz), 3.418 (4H, m), 3.619 (4H, m), 3.854 (2H, m), 4.053 (2H, dd, J=18, 15 Hz), 4.596 (4H, m), 7.081 (4H, m), 7.419 (1H, s), 7.458 (1H, s).

Isomer Q-2: ¹H NMR (300 MHz, CD₃OD): δ 1.18 (3H, t, J=7.5 Hz), 2.58 (2H, q, J=7.8 Hz) 2.62-2.64 (1H, m), 2.78 (1H, t, J=6.6 Hz), 3.16-3.21 (1H, m), 3.33-3.43 (1H, m), 3.57-3.68 (1H, m), 3.60 (2H, dd, J=6.3 Hz), 3.76-3.86 (2H, m), 3.91-3.96 (1H, m), 4.00 (1H, s), 4.04 (2H, d, J=3.9 Hz), 4.12 (1H, dd, J=3.3 Hz), 4.27 (1H, dd, J=3 Hz), 4.49-4.63 (2H, m), 7.06-7.07 (4H, m), 7.35 (1H, d, J=2.4 Hz), 7.46 (1H, s).

Example 9

Figure 11:
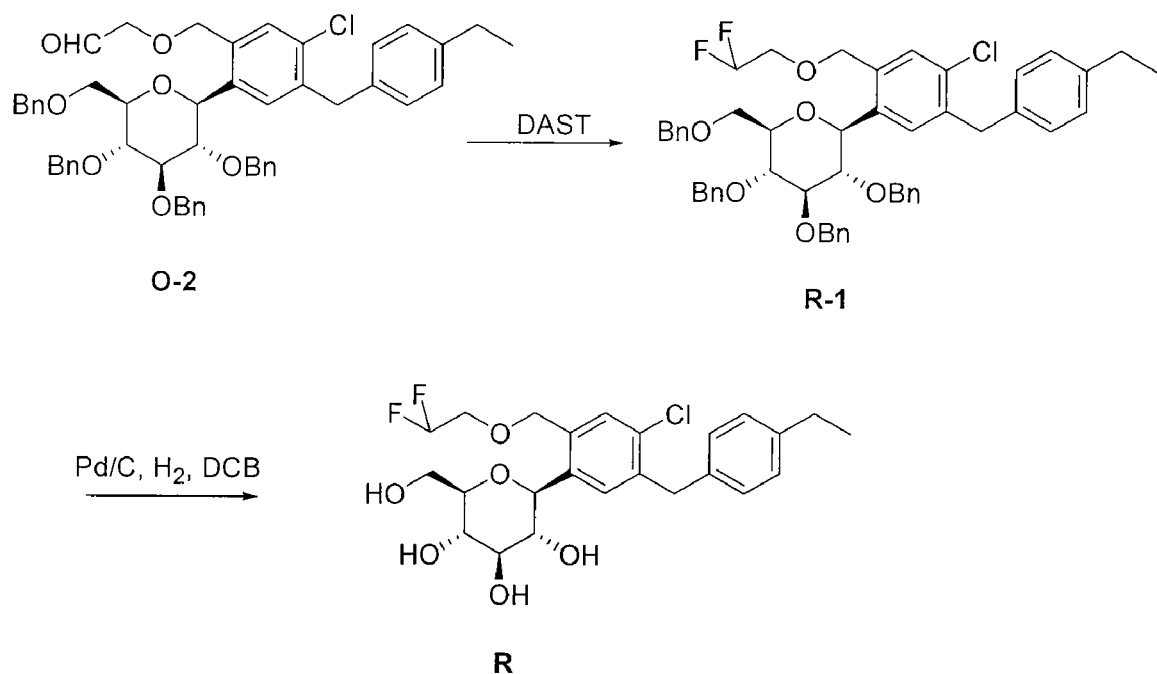

This example illustrates the preparation of compound R according to the approach provided in FIG. 11.

Preparation of (2R,3R,4R,5S,6S)-3,4,5-tris(benzyloxy)-2-(benzyloxymethyl)-6-(4-chloro-2-((2,2-difluoroethoxy)methyl)-5-(4-ethylbenzyl)phenyl)tetrahydro-2H-pyran (Intermediate R-1)

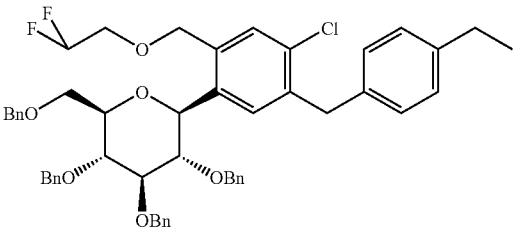

DAST (29 mg, 18 mmol) was added dropwise to a solution of 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)acetaldehyde (intermediate O-2) (50 mg, 0.06 mmol) in anhydrous CH$_2$Cl$_2$ (5 mL) at −78° C. under argon, and the mixture was stirred overnight while the temperature was warmed to room temperature. The reaction mixture was quenched by MeOH (1 mL) and evaporated to dryness. The residue was purified by preparative TLC, which afforded (2R,3R,4R,5S,6S)-3,4,5-tris(benzyloxy)-2-(benzyloxymethyl)-6-(4-chloro-2-((2,2-difluoroethoxy)methyl)-5-(4-ethylbenzyl)phenyl)tetrahydro-2H-pyran (intermediate R-1) (51 mg, 0.06 mmol, yield 100%).

Preparation of (2S,3R,4R,5S,6R)-2-(4-chloro-2-((2,2-difluoroethoxy)methyl)-5-(4-ethylbenzyl)phenyl)-6-(hydroxymethyl)tetrahydro-2H-pyran-3,4,5-triol (Compound R)

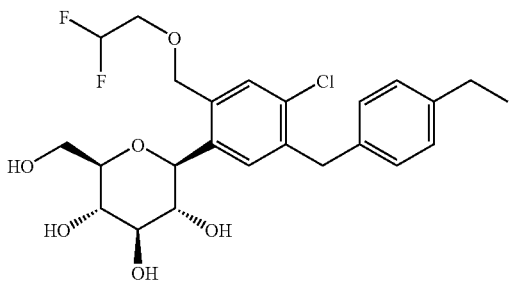

Compound R was prepared from (2R,3R,4R,5S,6S)-3,4,5-tris(benzyloxy)-2-(benzyloxymethyl)-6-(4-chloro-2-((2,2-difluoroethoxy)methyl)-5-(4-ethylbenzyl)phenyl)tetrahydro-2H-pyran (intermediate R-1) using debenzylation methods analogous to those described in Example 6 above. MS ESI m/z (%) 504 (M+NH$_4$)$^+$, 973 (2M+H)$^+$, 531 (M+HCOOH−H)$^-$, 971 (2M−H)$^-$. $^1$H-NMR (CD$_3$OD, 300 MHz) δ 1.186 (t, J=7.5 Hz, 3H), 2.580 (dd, J=7.5 Hz, 2H), 3.415 (m, 4H), 3.694 (m, 3H), 3.855 (d, J=11.7 Hz, 1H), 4.056 (dd, J=18, 15 Hz, 2H), 4.438 (d, J=8.7 Hz, 1H), 4.649 (d, J=12.6 Hz, 1H), 4.864 (d, J=12.3 Hz, 1H), 4.787 (tt, J=55.2, 3.9 Hz, 1H), 7.068 (s, 4H), 7.416 (s, 1H), 7.460 (s, 1H).

Example 10

Preparation of (2R,3R,4R,5S,6S)-3,4,5-tris(benzyloxy)-2-(benzyloxymethyl)-6-(4-chloro-5-(4-ethylbenzyl)-2-((2-methoxyethoxy)methyl)phenyl)tetrahydro-2H-pyran (Intermediate S-1)

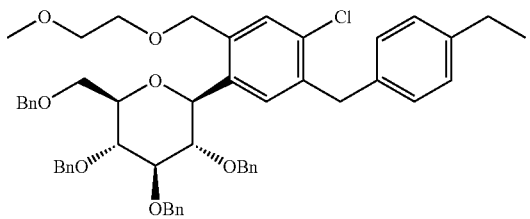

NaH (2 mg, 0.087 mmol) was added to a solution of 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)ethanol (intermediate O-3) (60 mg, 0.073 mmol) in anhydrous THF (10 mL) at 0° C., and stirred for 1 h, then TBAI (2.6 mg, 0.007 mmol) and CH$_3$I (1.5 mg, 0.11 mmol) were added to the reaction mixture at the same temperature and stirred overnight. Then the mixture was washed with water (10 mL×3), then brine, and the organic layer was dried over Na$_2$SO$_4$, filtered, and evaporated to dryness. The residue (intermediate S-1) was used in the next step without further purification.

Preparation of (2S,3R,4R,5S,6R)-2-(4-chloro-5-(4-ethylbenzyl)-2-((2-methoxyethoxy)methyl)phenyl)-6-(hydroxymethyl)tetrahydro-2H-pyran-3,4,5-triol (Compound S)

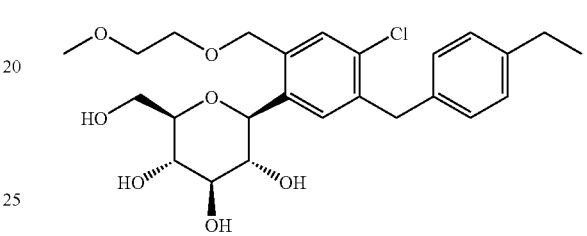

Compound S was prepared from intermediate S-1 using debenzylation methods analogous to those described in Example 6 above. MS ESI m/z (%) 481 (M+H)$^+$, 498 (M+NH$_4$)$^+$, 961 (2M+1)$^+$, 525 (M+HCOOH−H)$^-$. $^1$H-NMR (CD$_3$OD, 300 MHz) δ 1.186 (t, J=7.5 Hz, 3H), 2.577 (dd, J=7.5 Hz, 2H), 3.404 (m, 7H), 3.601 (m, 5H), 3.844 (d, J=11.1 Hz, 1H), 4.049 (dd, J=18, 15 Hz, 2H), 4.459 (d, J=9.3 Hz, 1H), 4.537 (d, J=12 Hz, 1H), 4.743 (d, J=12 Hz, 1H), 7.073 (s, 4H), 7.415 (s, 1H), 7.459 (s, 1H).

Example 11

Figure 12:
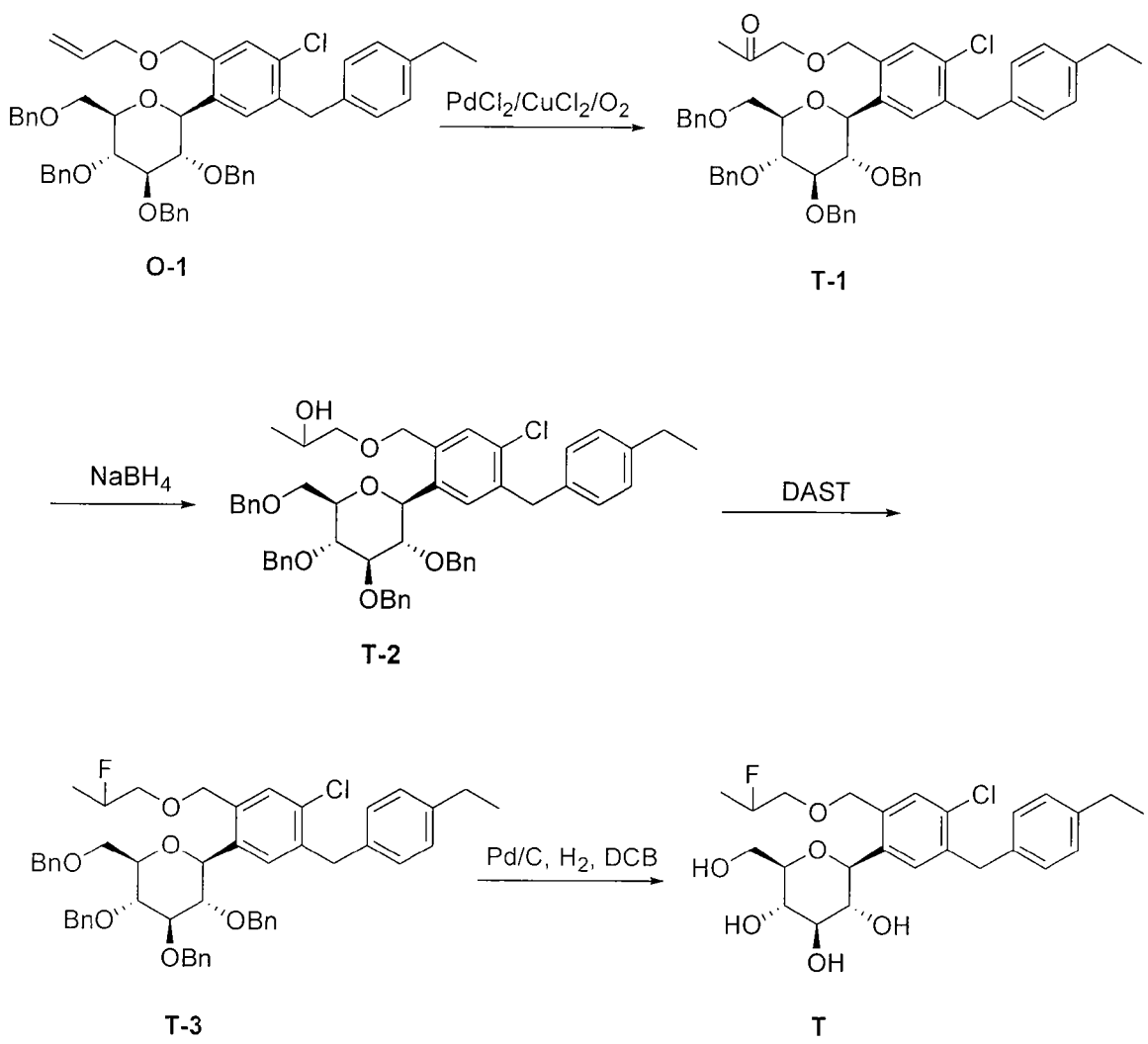

This example illustrates the preparation of compound T according to the approach provided in FIG. 12.

Preparation of 1-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)propan-2-one (Intermediate T-1)

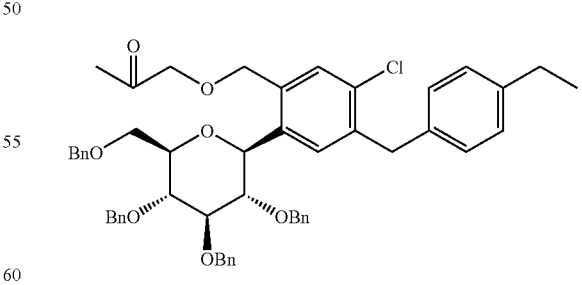

A mixture of palladium chloride (159 mg, 0.053 mmol) and copper chloride (267 mg, 0.27 mmol) in DMF (3 mL) was stirred for 2.5 h at room temperature. (2S,3S,4R,5R,6R)-2-(2-(allyloxymethyl)-4-chloro-5-(4-ethylbenzyl)phenyl)-3,4,5-tris(benzyloxy)-6-(benzyloxymethyl)tetrahydro-2H-pyran (intermediate O-1) (300 mg, 0.36 mmol) was added to the mixture and stirred overnight under oxygen. The reaction mixture was filtered, the filtrate was poured into water and extracted with ethyl acetate (20 mL×3). The combined extracts were dried over Na$_2$SO$_4$, filtered, and evaporated to dryness. The residue was purified by preparative TLC, which afforded 1-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)propan-2-one (intermediate T-1) (178 mg, 0.33 mmol, yield 58.2%). $^1$H-NMR (DMSO-d$_6$, 300 MHz) δ 1.062 (t, J=8.1 Hz, 3H), 1.988 (s, 3H), 2.452 (dd, J=8.1 Hz, 2H), 3.603 (m, 6H), 3.793 (m, 2H), 3.997 (s, 2H), 4.125 (s, 2H), 4.491 (11, 7H), 4.744 (m, 4H), 6.789 (m, 2H), 7.015 (m, 4H), 7.169 (m, 5H), 7.288 (m, 13H), 7.457 (s, 2H).

Preparation of 1-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)propan-2-ol (Intermediate T-2)

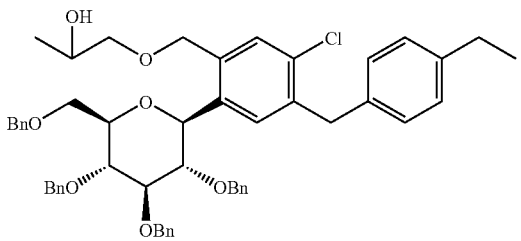

NaBH$_4$ (4.5 mg, 0.12 mmol) was added to a solution of 1-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)propan-2-ol (intermediate T-1) (50 mg, 0.06 mmol) in THF (5 mL) and stirred for 1 h at room temperature. The reaction was quenched by the addition of saturated NH$_4$Cl (2 mL), and the mixture was then extracted with ethyl acetate (10 mL×3). The combined extracts were dried over Na$_2$SO$_4$, filtered, and evaporated to dryness. The residue was purified by preparative TLC, which afforded 1-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)propan-2-ol (intermediate T-2) (49 mg, 0.058 mmol, yield 97.8%).

Preparation of (2S,3R,4R,5S,6R)-2-(4-chloro-5-(4-ethylbenzyl)-2-((2-fluoropropoxy)methyl)phenyl)-6-(hydroxymethyl)tetrahydro-2H-pyran-3,4,5-triol (Compound T)

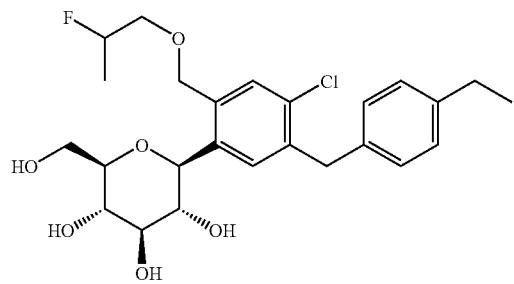

Intermediate T3 was prepared from intermediate T2 using DAST reagent, and compound T was prepared from intermediate T3 by debenzylation using methods analogous to those described in Example 9. MS ESI m/z (%) 482 (M+H)$^+$, 500 (M+NH$_4$)$^+$, 527 (M+HCOOH−H)$^−$. $^1$H-NMR (CD$_3$OD, 300 MHz) δ 1.186 (t, J=7.5 Hz, 3H), 1.306 (ddd, J=23.4, 6.5, 0.6 Hz, 3H), 2.578 (dd, J=7.5 Hz, 2H), 3.409 (m, 4H), 3.553 (d, J=4.8 Hz, 1H), 3.646 (m, 2H), 3.850 (d, J=12 Hz, 1H), 1H, 4.050 (dd, J=18, 15 Hz, 2H), 4.462 (dd, J=9.3, 2.4 Hz, 1H), 4.595 (d, J=12.3 Hz, 1H), 4.799 (d, J=12.6 Hz, 1H), 7.076 (s, 4H), 7.411 (s, 1H), 7.457 (s, 1H).

Example 12

Preparation of (2S,3R,4R,5S,6R)-2-(4-chloro-5-(4-ethylbenzyl)-2-((2-methoxypropoxy)methyl)phenyl)-6-(hydroxymethyl)tetrahydro-2H-pyran-3,4,5-triol (Compound U)

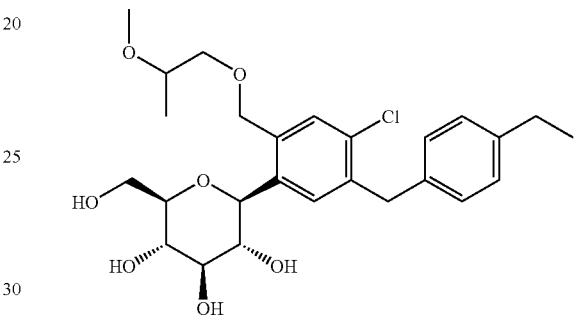

Compound U was prepared from intermediate T-2 using methods analogous to those described in Example 10 above. MS ESI m/z (%) 495 (M+H)$^+$, 512 (M+NH$_4$)$^+$, 989 (2M+H)$^+$, 539 (M+HCOOH−H)$^−$. $^1$H-NMR (CD$_3$OD, 300 MHz) δ 1.145 (dd, J=6.3, 1.2 Hz, 3H), 1.185 (t, J=7.5 Hz, 3H), 2.578 (dd, J=7.5 Hz, 2H), 3.440 (m, 11H), 3.856 (d, J=11.4 Hz, 1H), 4.049 (dd, J=18, 15 Hz, 2H), 4.462 (d, J=9.3 Hz, 1H), 4.561 (dd, J=12.3, 1.8 Hz, 1H), 4.748 (dd, J=12.3, 1.8 Hz, 1H), 7.075 (s, 4H), 7.049 (s, 1H), 7.456 (s, 1H).

Example 13

Preparation of (5-chloro-4-(4-ethylbenzyl)-2-((2S,3S,4R,5R,6R)-3,4,5-tris(benzyloxy)-6-(benzyloxymethyl)tetrahydro-2H-pyran-2-yl)phenyl)methanol (Intermediate V-1)

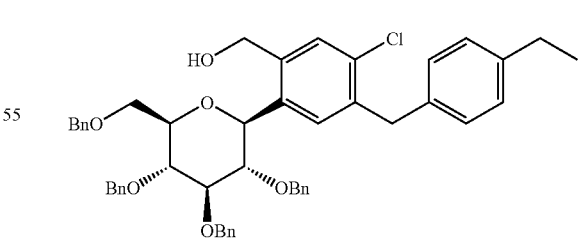

PdCl$_2$ (23.7 mg, 0.133 mmol, 2.2 eq) and NaOAc (76 mg, 0.285 mmol, 4 eq) were added to a solution of (2S,3S,4R,5R,6R)-2-(2-(allyloxymethyl)-4-chloro-5-(4-ethylbenzyl)phenyl)-3,4,5-tris(benzyloxy)-6-(benzyloxymethyl)tetrahydro-2H-pyran (intermediate O-1) (50 mg, 0.061 mmol) in HOAc:H$_2$O (9:1) (1 mL), and the mixture was stirred at 70° C. for 1 h. Then the mixture was cooled to room temperature, extracted with ethyl acetate, and the combined organic layers were washed with water, dried over anhydrous Na₂SO₄, concentrated and purified by preparative TLC to obtain 30 mg of intermediate V-1.

Preparation of (2R,3R,4R,5S,6S)-3,4,5-tris(benzyloxy)-2-(benzyloxymethyl)-6-(4-chloro-5-(4-ethylbenzyl)-2-((2,2,2-trifluoroethoxy)methyl)phenyl)tetrahydro-2H-pyran (Intermediate V-2)

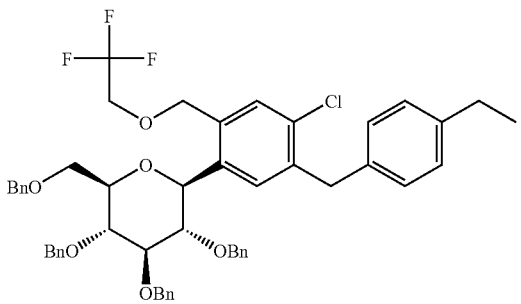

To a solution of (5-chloro-4-(4-ethylbenzyl)-2-((2S,3S,4R,5R,6R)-3,4,5-tris(benzyloxy)-6-(benzyloxymethyl)tetrahydro-2H-pyran-2-yl)phenyl)methanol (0.783 g, 1 mmol) (V-1) in toluene (2 mL) was added ADDP (2 mmol) at room temperature. The mixture was stirred for 10 min and then Bu₃P (2 mmol) was added. After stirring for 1 h, CF₃CH₂OH (1.0 g, 10 mmol) was added. The mixture was stirred overnight. After removal of volatiles under reduced pressure, the residue was purified by preparative LC-MS to obtain (2R,3R,4R,5S,6S)-3,4,5-tris(benzyloxy)-2-(benzyloxymethyl)-6-(4-chloro-5-(4-ethylbenzyl)-2-((2,2,2-trifluoroethoxy)methyl)phenyl)tetrahydro-2H-pyran (intermediate V-2).

Preparation of (2S,3R,4R,5S,6R)-2-(4-chloro-5-(4-ethylbenzyl)-2-((2,2,2-trifluoroethoxy)methyl)phenyl)-6-(hydroxymethyl)tetrahydro-2H-pyran-3,4,5-triol (Compound V)

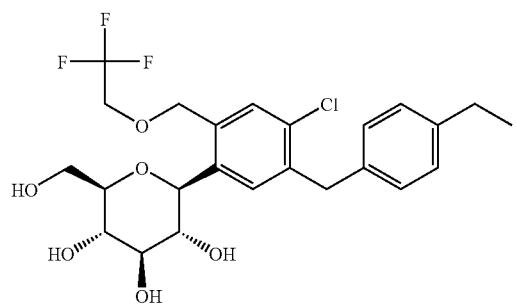

Compound V was prepared from intermediate V-2 using debenzylation methods analogous to those described in Example 6 above. ¹H-NMR (300 MHz, CD₃OD): δ 1.18 (3H, t, J=7.8 Hz), 2.58 (2H, q, J=7.5 Hz), 3.36-3.46 (4H, m), 3.63-3.69 (1H, m), 3.85 (1H, d, J=1.2 Hz), 3.98 (2H, t, J=8.7 Hz), 4.064 (2H, d, J=6.6 Hz), 4.42 (1H, d, J=9.3 Hz), 4.71 (1H, d, J=12.0 Hz), 4.94, (1H, d, J=12.0 Hz), 7.084 (4H, s), 7.47 (1H, s), 7.41 (1H, s).

Example 14

Preparation of (2S,3R,4R,5S,6R)-2-(4-chloro-5-(4-ethylbenzyl)-2-((2-hydroxy-3-methoxypropoxy)methyl)phenyl)-6-(hydroxymethyl)tetrahydro-2H-pyran-3,4,5-triol (Compound W)

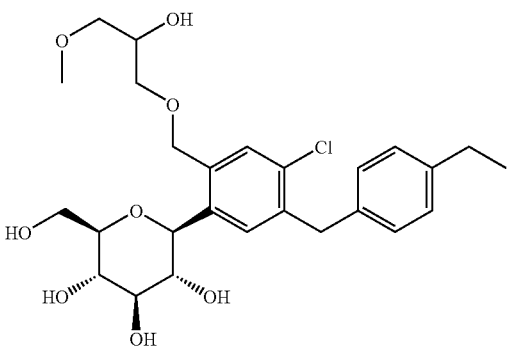

Compound W was prepared from a mixture of compounds Q-1 and Q-2 using methods evident to those skilled in the art. ¹H-NMR (300 MHz, CDCl₃): δ 1.17 (3H, t, J=7.5 Hz), 2.57 (2H, t, J=7.5 Hz), 3.23 (3H, s), 3.25-3.91 (11H, m), 4.02 (2H, s), 3.40-3.57 (3H, m), 7.60 (4H, m), 7.27 (1H, s), 7.37 (1H, d, J=4.2 Hz).

Example 15

Preparation of (2S,3R,4R,5S,6R)-2-(4-chloro-5-(4-ethylbenzyl)-2-((2-(methylamino)propoxy)methyl)phenyl)-6-(hydroxymethyl)tetrahydro-2H-pyran-3,4,5-triol (Compound X)

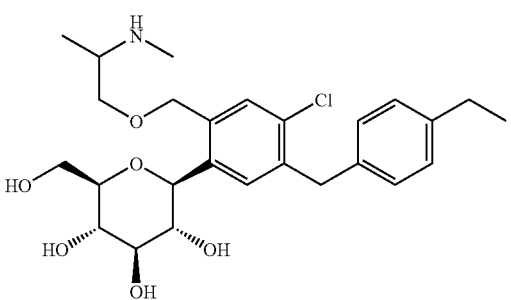

To a solution of 1-(5-chloro-4-(4-ethylbenzyl)-2-((2S,3R,4R,5S,6R)-3,4,5-trihydroxy-6-(hydroxymethyl)tetrahydro-2H-pyran-2-yl)benzyloxy)propan-2-one (compound K) (0.478 g, 1 mmol) in ethanol (5 mL), was added CH₃NH₂/ethanol (10 mmol) at 0° C. AcOH (catalytic) was added, and the mixture was stirred for 1 h at 0° C. NaBH₃CN (3 mmol) was added, and the reaction was monitored by LC-MS. After the reaction was complete, ethyl acetate and water were added. The organic layer was separated and dried over anhydrous NaSO₄, washed with brine and concentrated. The residue was purified by preparative LC-MS to obtain compound X. ¹H-NMR (300 MHz, CD₃OD): δ 1.16 (3H, 1.16, J=7.5 Hz), 1.27 (3H, d, J=6.9 Hz), 2.52-2.63 (6H, m) 3.33-3.71 (9H, m), 3.86 (1H, d, J=11.7 Hz), 4.04 (2H, s), 4.46 (1H, d, J=8.7 Hz), 4.58 (1H, dd, J=5.7 Hz), 7.03-7.09 (4H, m), 7.41 (1H, s), 7.45 (1H, s).

Example 16

Preparation of (2S,3R,4R,5S,6R)-2-(4-chloro-5-(4-ethylbenzyl)-2-((2-hydroxy-3-(methylamino)propoxy)methyl)phenyl)-6-(hydroxymethyl)tetrahydro-2H-pyran-3,4,5-triol (Compound Y)

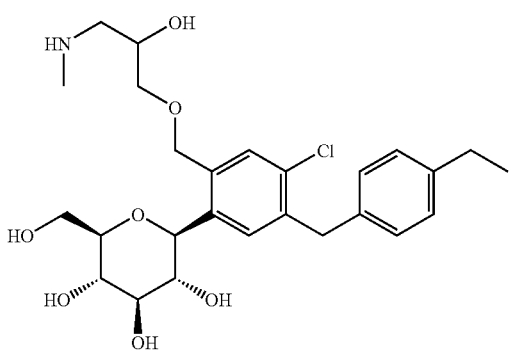

Compound Y was prepared from a mixture of compounds Q-1 and Q-2 using methods evident to those skilled in the art. $^1$H-NMR (300 MHz, CD$_3$OD): δ 1.18 (3H, t, J=7.5 Hz), 2.58 (2H, q, J=7.2 Hz), 2.67 (3H, s) 2.96-3.15 (2H, m), 3.35-3.66 (6H, m), 3.88 (1H, d, J=12 Hz), 3.96-4.01 (1H, m), 4.05 (2H, s), 4.48 (1H, d, J=9 Hz), 4.57 (1H, dd, J=7.2 Hz), 4.77 (2H, t, J=12.3 Hz), 7.05-7.11 (4H, m), 7.41 (1H, s) 7.47 (1H, s).

Example 17

Preparation of (2S,3R,4R,5S,6R)-2-(4-chloro-2-((3-(diethylamino)-2-hydroxypropoxy)methyl)-5-(4-ethylbenzyl)phenyl)-6-(hydroxymethyl)tetrahydro-2H-pyran-3,4,5-triol (Compound Z)

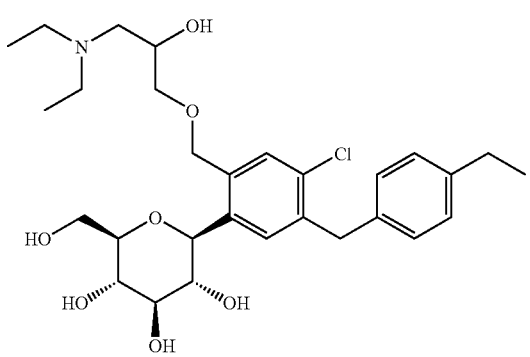

Compound Z was prepared from a mixture of compounds Q-1 and Q-2 using methods evident to those skilled in the art. $^1$H-NMR (300 MHz, CD$_3$OD): δ 1.19 (3H, t, J=7.5 Hz), 1.28 (6H, t, J=7.2 Hz), 2.58 (2H, q, J=7.2 Hz), 3.12-3.25 (6H, m), 3.53-3.66 (5H, m), 4.02 (2H, m), 4.09-4.17 (TH, m), 4.26 (1H, dd, J=3 Hz), 2.45-2.65 (2H, m), 4.8 (1H, t, J=12.3 Hz), 7.05-7.12 (4H, m), 7.41 (1H, s), 7.47 (1H, d, J=2.4 Hz).

Example 18

Preparation of (2S,3R,4R,5S,6R)-2-(4-chloro-5-(4-ethylbenzyl)-2-((2-hydroxy-3-(2,2,2-trifluoroethoxy)propoxy)methyl)phenyl)-6-(hydroxymethyl)tetrahydro-2H-pyran-3,4,5-triol (Compound AA)

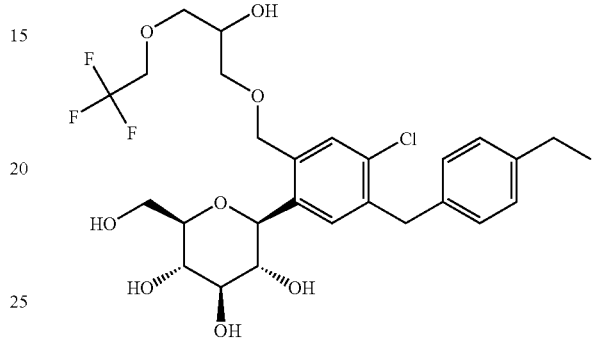

Compound AA was prepared from a mixture of compounds Q-1 and Q-2 using methods evident to those skilled in the art. $^1$H-NMR (300 MHz, CD$_3$OD): δ 1.190 (3H, m, 7.5 Hz), 2.58 (2H, q, J=7.8 Hz), 3.37-4.13 (14H, m), 4.27 (1H, d, J=3 Hz), 4.49 (1H, dd, J=8.4 Hz), 4.58 (1H, dd, J=4.8 Hz), 4.75 (1H, dd, J=6.9 Hz), 7.08-7.11 (4H, m), 7.42 (1H, s), 7.46 (1H, s).

Example 19

Preparation of (2S,3R,4R,5S,6R)-2-(4-chloro-5-(4-ethylbenzyl)-2-((2-morpholinopropoxy)methyl)phenyl)-6-(hydroxymethyl)tetrahydro-2H-pyran-3,4,5-triol (Compound AB)

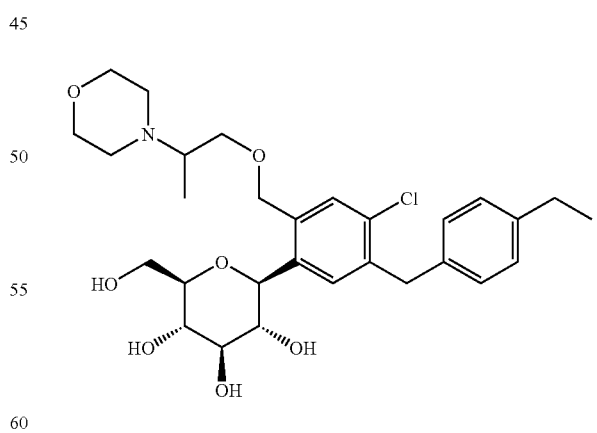

Compound AB was prepared using methods analogous to those described in Example 15 above (using morpholine in place of methylamine). $^1$H-NMR (300 MHz, CD$_3$OD): δ 1.18 (3H, t, J=7.8 Hz), 1.32 (3H, dd, J=3.6 Hz), 2.58 (2H, q, J=7.8 Hz), 3.03-3.11 (4H, m), 3.34-3.39 (2H, m), 3.43-3.45 (2H, m), 3.58-3.67 (2H, m), 3.72-3.89 (6H, m), 4.06 (2H, s), 4.46-

4.50 (1H, m), 4.56 (1H, dd, J=3.9 Hz), 4.81 (2H, dd, J=6.3 Hz), 7.05-7.12 (4H, m), 7.43 (1H, s), 7.49 (1H, s).

Example 20

Preparation of 2-(2-bromo-5-chloro-4-(4-ethylbenzyl)phenyl)ethanol (Intermediate AC)

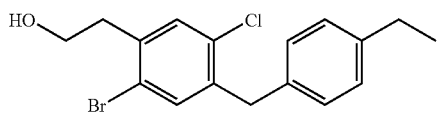

To a cooled (0° C.) solution of olefin (453 mg, 1.35 mmol) in THF (5 mL), was added dropwise 9-BBN (3.24 mL, 1.62 mmol, 0.5 M in THF) over 30 min. After the addition was complete, the ice bath was removed and the reaction mixture was stirred at room temperature overnight. The mixture was recooled to 0° C. and quenched by dropwise addition of MeOH (2.2 mL). Aqueous NaOH (2 M, 5.6 mL) and 30% $H_2O_2$ (1.2 mL) were added to the stirred mixture. After being stirred for 3 h, the mixture was extracted 3× with EtOAc. The combined organic extracts were washed with brine and dried over $Na_2SO_4$. Concentration gave the crude product, which was purified by flash chromatography (using 100% petroleum ether to 5:1 PE:EtOAc as eluent) to yield 336 mg of title product. $^1$H-NMR (CDCl$_3$, 300 MHz) δ 7.34 (s, 1H), 7.30 (s, 1H), 7.13 (q, 4H), 4.00 (s, 2H), 3.87 (t, J=6.6 Hz, 2H), 2.96 (t, J=6.6 Hz, 2H), 2.63 (q, J=7.6 Hz, 2H), 1.23 (t, J=7.6 Hz, 3H).

Preparation of (2S,3R,4R,5S,6R)-2-(2-(2-(allyloxy)ethyl)-4-chloro-5-(4-ethylbenzyl)phenyl)-6-(hydroxymethyl)tetrahydro-2H-pyran-3,4,5-triol (Compound AD)

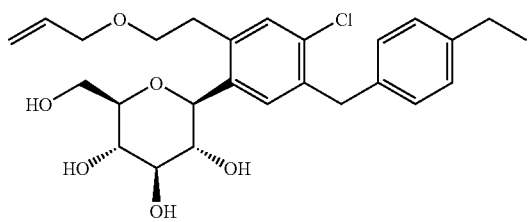

Compound AD was prepared using intermediate AC and methods analogous to those described in Example 1 above. $^1$H-NMR (CD$_3$OD, 300 MHz) δ 7.39 (s, 1H), 7.26 (s, 1H), 7.08 (s, 4H), 5.97-5.84 (m, 1H), 5.29-5.12 (m, 2H), 4.44 (d, J=9.0 Hz, 1H), 4.03-3.97 (m, 4H), 3.85 (d, J=11.1 Hz, 1H), 3.70-3.62 (m, 3H), 3.48-3.37 (m, 4H), 3.12-3.03 (m, 1H), 2.95-2.86 (m, 1H), 2.58 (q, J=7.6 Hz, 2H), 1.19 (t, J=7.6 Hz, 31H); MS ESI (m/z) 477 (M+1)$^+$, calc. 476.

Example 21

Preparation of (2R,3R,4R,5S,6S)-2-(acetoxymethyl)-6-(4-chloro-5-(4-ethylbenzyl)-2-(2-(2-oxoethoxy)ethyl)phenyl)tetrahydro-2H-pyran-3,4,5-triyl triacetate (Intermediate AE)

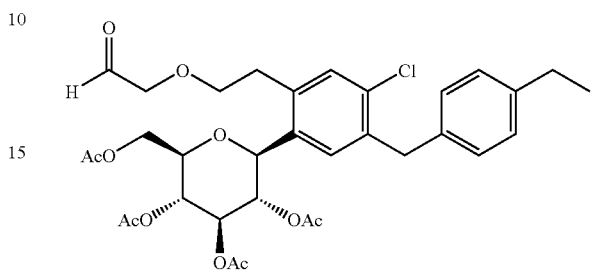

O$_3$ was bubbled through a cooled (−78° C.) solution of (2R,3R,4R,5S,6S)-2-(acetoxymethyl)-6-(2-(2-(allyloxy)ethyl)-4-chloro-5-(4-ethylbenzyl)phenyl)tetrahydro-2H-pyran-3,4,5-triyl triacetate (104 mg, 0.16 mmol) in CH$_2$Cl$_2$ (8 mL) until the color changed to blue. Then argon was bubbled through the reaction solution until the solution became colorless. Me$_2$S (0.12 mL, 1.6 mmol) was added to the reaction solution, which was allowed to warm to room temperature and stirred for 30 min. The solution was concentrated and the residue was purified by preparative TLC to yield 63 mg of title compound. $^1$H-NMR (CD$_3$OD, 300 MHz) δ 9.69 (s, 1H), 7.23 (s, 1H), 7.22 (s, 1H), 7.13-7.06 (m, 4H), 5.36-5.12 (m, 3H), 4.72 (d, J=9.3 Hz, 1H), 4.26-4.07 (m, 4H), 4.01 (s, 2H), 3.88-3.64 (m, 3H), 3.16-3.06 (m, 1H), 2.98-2.89 (m, 1H), 2.60 (q, J=7.5 Hz, 2H), 2.04 (s, 6H), 2.00 (s, 3H), 1.71 (s, 3H), 1.20 (t, J=7.5 Hz, 3H).

Preparation of (2R,3R,4R,5S,6S)-2-(acetoxymethyl)-6-(4-chloro-5-(4-ethylbenzyl)-2-(2-(2-hydroxyethoxy)ethyl)phenyl)tetrahydro-2H-pyran-3,4,5-triyl triacetate (Intermediate AF)

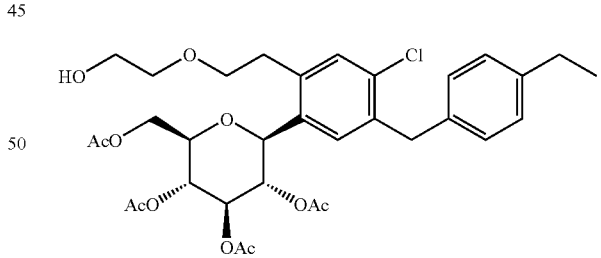

To a cooled (0° C.) solution of (2R,3R,4R,5S,6S)-2-(acetoxymethyl)-6-(4-chloro-5-(4-ethylbenzyl)-2-(2-(2-oxoethoxy)ethyl)phenyl)tetrahydro-2H-pyran-3,4,5-triyl triacetate (25 mg, 0.039 mmol) and NaBH$_4$ (5.5 mg, 0.145 mmol) in THF (0.8 mL), was added MeOH (0.03 mL) dropwise. After being stirred for 1 h at the same temperature, the reaction was quenched by addition of saturated NH$_4$Cl. The mixture was extracted 3× with EtOAc. The combined organic layers were washed with brine and dried over Na$_2$SO$_4$. Concentration gave the pure product in quantitative yield. MS ESI (m/z) 649 (M+1)$^+$, calc. 648.

Preparation of (2S,3R,4R,5S,6R)-2-(4-chloro-5-(4-ethylbenzyl)-2-(2-(2-hydroxyethoxy)ethyl)phenyl)-6-(hydroxymethyl)tetrahydro-2H-pyran-3,4,5-triol (Compound AG)

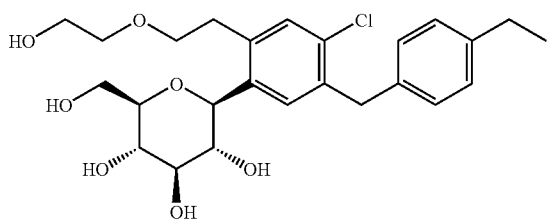

To a solution of (2R,3R,4R,5S,6S)-2-(acetoxymethyl)-6-(4-chloro-5-(4-ethylbenzyl)-2-(2-(2-hydroxyethoxy)ethyl)phenyl)tetrahydro-2H-pyran-3,4,5-triyl triacetate (31 mg, 0.048 mmol) in THF:MeOH:H$_2$O (2:3:1, 0.6 mL) was added LiOH—H$_2$O (2.8 mg, 0.067 mmol). After being stirred overnight at room temperature, the reaction mixture was concentrated. The residue was dissolved in EtOAc, washed 1× with brine, 1× with brine containing 1% NaHSO$_4$ and 1× with brine prior to drying over Na$_2$SO$_4$. Concentration gave 22 mg of title compound. $^1$H-NMR (CD$_3$OD, 300 MHz) δ 7.38 (s, 1H), 7.27 (s, 1H), 7.07 (s, 4H), 4.47 (dd, J=9.6, 3.0 Hz, 1H), 4.02 (s, 2H), 3.85 (d, J=12.3 Hz, 1H), 3.71-3.62 (m, 5H), 3.53-3.46 (m, 4H), 3.39-3.37 (m, 2H), 3.13-3.03 (m, 1H), 2.97-2.87 (m, 1H), 2.58 (q, J=7.5 Hz, 2H), 1.19 (t, J=7.5 Hz, 3H); MS ESI (m/z) 481 (M+1)$^+$, calc. 480.

Example 22

Preparation of (2S,3R,4R,5S,6R)-2-(4-chloro-5-(4-ethylbenzyl)-2-(2-(2-fluoroethoxy)ethyl)phenyl)-6-(hydroxymethyl)tetrahydro-2H-pyran-3,4,5-triol (Compound AH)

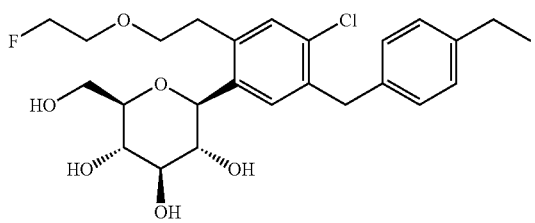

To a cooled (−78° C.) solution of (2R,3R,4R,5S,6S)-2-(acetoxymethyl)-6-(4-chloro-5-(4-ethylbenzyl)-2-(2-(2-hydroxyethoxy)ethyl)phenyl)tetrahydro-2H-pyran-3,4,5-triyl triacetate (28.7 mg, 0.044 mmol) in CH$_2$Cl$_2$ (1 mL) was added DAST (0.04 mL, 0.3 mmol) dropwise. After being stirred for 2.5 h at the same temperature, the reaction was quenched by addition of saturated Na$_2$CO$_3$. The mixture was extracted 3× with CH$_2$Cl$_2$, and the combined organic layers were washed 1× with brine and dried over Na$_2$SO$_4$. Concentration gave the crude product, which was used for the next step without further purification. To a solution of the crude product in THF:MeOH:H$_2$O (2:3:1, 0.8 mL), was added LiOH—H$_2$O (3.7 mg, 0.088 mmol). After being stirred overnight at room temperature, the reaction mixture was concentrated. The residue was dissolved in EtOAc, washed 1× with brine, 1× with brine containing 1% NaHSO$_4$ and 1× with brine prior to drying over Na$_2$SO$_4$. Concentration gave the crude product, which was purified by preparative HPLC to yield 5.7 mg of title compound. $^1$H-NMR (CD$_3$OD, 300 MHz) δ 7.38 (s, 1H), 7.26 (s, 1H), 7.08 (s, 4H), 4.59-4.56 (m, 1H), 4.46-4.40 (m, 2H), 4.05 (d, J=15.1 Hz, 1H), 3.99 (d, J=15.1 Hz, 1H), 3.84 (d, J=12.0 Hz, 1H), 3.75-3.61 (m, 5H), 3.48-3.36 (m, 4H), 3.13-3.03 (m, 1H), 2.96-2.87 (m, 1H), 2.57 (q, J=7.6 Hz, 2H), 1.18 (t, J=7.6 Hz, 3H); MS ESI (m/z) 483 (M+1)$^+$, calc. 482.

Example 23

Preparation of (2S,3R,4R,5S,6R)-2-(4-chloro-2-(2-(2,2-difluoroethoxy)ethyl)-5-(4-ethylbenzyl)phenyl)-6-(hydroxymethyl)tetrahydro-2H-pyran-3,4,5-triol (Compound AI)

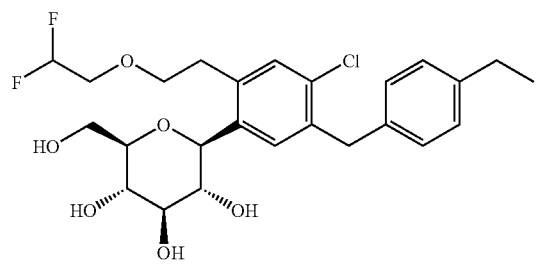

Compound AI was prepared from intermediate AE using methods analogous to those described in Example 22 above. $^1$H-NMR (CD$_3$OD, 300 MHz) δ 7.38 (s, 1H), 7.26 (s, 1H), 7.08 (s, 4H), 6.10-5.70 (m, 1H), 4.45-4.42 (m, 1H), 4.05 (d, J=15.1 Hz, 1H), 3.99 (d, J=15.1 Hz, 1H), 3.85 (d, J=12.0 Hz, 1H), 3.80-3.59 (m, 5H), 3.48-3.36 (m, 4H), 3.13-3.03 (m, 1H), 2.96-2.86 (m, 1H), 2.58 (q, J=7.6 Hz, 2H), 1.18 (t, J=7.6 Hz, 3H); MS ESI (m/z) 501 (M+1)$^+$, calc. 500.

Example 24

Preparation of (2R,3R,4R,5S,6S)-3,4,5-tris(benzyloxy)-2-(benzyloxymethyl)-6-(4-chloro-5-(4-ethylbenzyl)-2-(2-(2,2,2-trifluoroethoxy)ethyl)phenyl)tetrahydro-2H-pyran (Intermediate AJ)

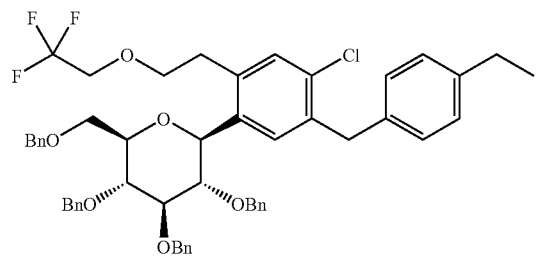

The solution of 5-chloro-4-(4-ethylbenzyl)-2-((2S,3S,4R,5R,6R)-3,4,5-tris(benzyloxy)-6-(benzyloxymethyl)tetrahydro-2H-pyran-2-yl)phenethyl methanesulfonate (58 mg, 0.066 mmol) in 0.8 mL of 1.5 M CF$_3$CH$_2$ONa in CF$_3$CH$_2$OH was stirred at 60° C. under argon. After it was stirred for about 9 h, an additional 0.6 mL of 1.5 M of CF$_3$CH$_2$ONa in CF$_3$CH$_2$OH was added and the mixture was stirred for another 15 h at 60° C. After removal of the volatiles with a rotary evaporator under vacuum, the residue was partitioned between water and EtOAC. The organic layer was separated, washed with brine and dried over Na₂SO₄. Concentration gave the crude product, which was purified by preparative TLC to yield 30 mg of title compound. MS ESI (m/z) 896 (M+NH₄)⁺, calc. 878.

Preparation of (2S,3R,4R,5S,6R)-2-(4-chloro-5-(4-ethylbenzyl)-2-(2-(2,2,2-trifluoroethoxy)ethyl)phenyl)-6-(hydroxymethyl)tetrahydro-2H-pyran-3,4,5-triol (Compound AK)

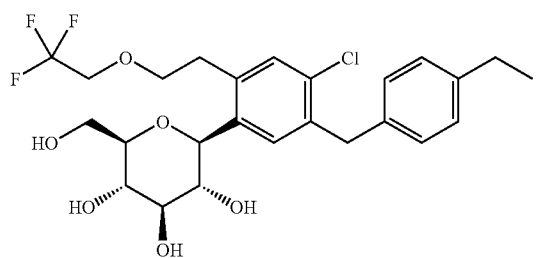

A mixture of (2R,3R,4R,5S,6S)-3,4,5-tris(benzyloxy)-2-(benzyloxymethyl)-6-(4-chloro-5-(4-ethylbenzyl)-2-(2-(2,2,2-trifluoroethoxy)ethyl)phenyl)tetrahydro-2H-pyran (30 mg, 0.034 mmol) and 10% Pd/C (30 mg) in 6 mL of MeOH:THF (1:1) was stirred under H₂ atmosphere (1 atm) for 2 h. The mixture was filtered, and the filtrate was concentrated to provide the crude product, which was purified by HPLC to yield 9 mg of title compound. ¹H-NMR (CD₃OD, 300 MHz) δ 7.40 (s, 1H), 7.27 (s, 1H), 7.10 (s, 4H), 4.44-4.41 (m, 1H), 4.06 (d, J=15.3 Hz, 1H), 4.00 (d, J=15.3 Hz, 1H), 3.95-3.79 (m, 5H), 3.67-3.61 (m, 1H), 3.48-3.46 (m, 2H), 3.39-3.36 (m, 2H), 3.15-3.05 (m, 1H), 2.98-2.91 (m, 1H), 2.58 (q, J=7.6 Hz, 2H), 1.19 (t, J=7.6 Hz, 3H); MS ESI (m/z) 519 (M+1)⁺, calc. 518.

Example 25

Preparation of (2S,3R,4R,5S,6R)-2-(4-chloro-5-(4-ethylbenzyl)-2-((3-hydroxypropoxy)methyl)phenyl)-6-(hydroxymethyl)tetrahydro-2H-pyran-3,4,5-triol (Compound AL)

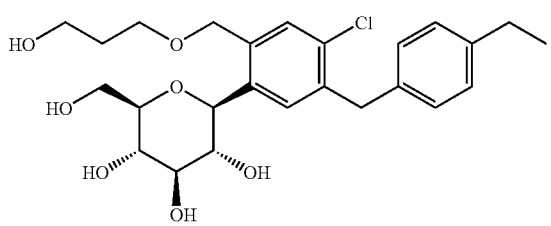

Compound AL was prepared from compound I using methods analogous to those described above as will be evident to those skilled in the art. ¹H-NMR (CD₃OD, 300 MHz) δ 7.46 (s, 1H), 7.40 (s, 1H), 7.08 (s, 4H), 4.73 (d, J=12.2 Hz, 1H), 4.53 (d, J=12.2 Hz, 1H), 4.45 (d, J=9.0 Hz, 1H), 4.08 (d, J=15.0 Hz, 1H), 4.02 (d, J=15.0 Hz, 1H), 3.86 (d, J=12.0 Hz, 1H), 3.68-3.60 (m, 4H), 3.44-3.29 (m, 5H), 2.58 (q, J=7.6 Hz, 2H), 1.86-1.79 (m, 2H), 1.19 (t, J=7.6 Hz, 3H); MS ESI (m/z) 481 (M+1)⁺, calc. 480.

Example 26

Preparation of (2S,3R,4R,5S,6R)-2-(4-chloro-5-(4-ethylbenzyl)-2-(2-(prop-2-ynyloxy)ethyl)phenyl)-6-(hydroxymethyl)tetrahydro-2H-pyran-3,4,5-triol (Compound AM)

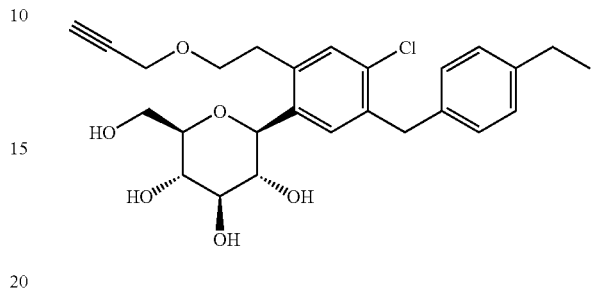

Compound AM was prepared from compound AD using methods analogous to those described in Example 5 above. ¹H-NMR (CD₃OD, 300 MHz) δ 7.38 (s, 1H), 7.26 (s, 1H), 7.10 (s, 4H), 4.45-4.42 (m, 1H), 4.15 (d, J=2.4 Hz, 2H), 4.05 (d, J=15.6 Hz, 1H), 3.99 (d, J=15.6 Hz, 1H), 3.85 (dd, J=12.3, 1.5 Hz, 1H), 3.74 (t, J=7.1 Hz, 2H), 3.67-3.62 (m, 1H), 3.48-3.45 (m, 2H), 3.40-3.37 (m, 2H), 3.13-3.04 (m, 1H), 2.96-2.89 (m, 1H), 2.83 (t, J=2.4 Hz, 1H), 2.57 (q, J=7.6 Hz, 2H), 1.18 (t, J=7.6 Hz, 3H); MS ESI (m/z) 475 (M+1)⁺, calc. 474.

Example 27

Preparation of (2S,3R,4R,5S,6R)-2-(2-(2-(but-2-ynyloxy)ethyl)-4-chloro-5-(4-ethylbenzyl)phenyl)-6-(hydroxymethyl)tetrahydro-2H-pyran-3,4,5-triol (Compound AN)

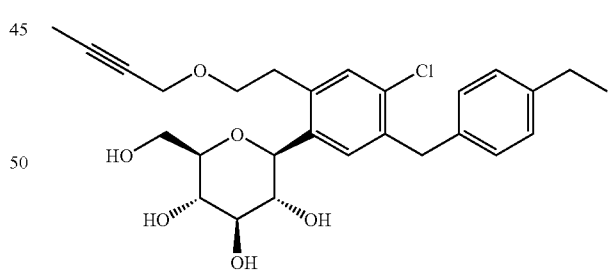

Compound AN was prepared using methods analogous to those described in Example 20 above. ¹H-NMR (CD₃OD, 300 MHz) δ 7.39 (s, 1H), 7.27 (s, 1H), 7.08 (s, 4H), 4.45-4.42 (m, 1H), 4.10 (q, J=2.4 Hz, 2H), 4.06 (d, J=15.6 Hz, 1H), 4.00 (d, J=15.6 Hz, 1H), 3.86 (d, J=11.1 Hz, 1H), 3.74-3.62 (m, 3H), 3.49-3.47 (In, 2H), 3.40-3.38 (m, 2H), 3.12-3.02 (m, 1H), 2.95-2.86 (m, 1H), 2.58 (q, J=7.5 Hz, 2H), 1.82 (t, J=2.4 Hz, 3H), 1.19 (t, J=7.5 Hz, 3H); MS ESI (m/z) 489 (M+1)⁺, calc. 488.

Example 28

Preparation of (2S,3R,4R,5S,6R)-2-(4-chloro-5-(4-ethoxybenzyl)-2-(2-(prop-2-ynyloxy)ethyl)phenyl)-6-(hydroxymethyl)tetrahydro-2H-pyran-3,4,5-triol (Compound AO)

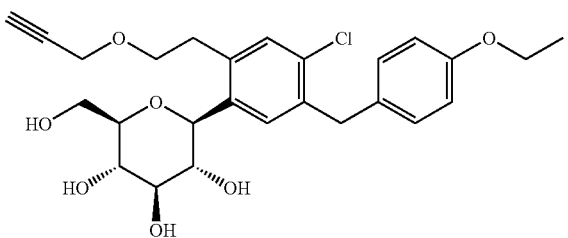

Compound AO was prepared using methods analogous to those described in Example 5 above. $^1$H-NMR (CD$_3$OD, 300 MHz) δ 7.37 (s, 1H), 7.26 (s, 1H), 7.08 (d, J=8.7 Hz, 2H), 6.78 (d, J=8.7 Hz, 2H), 4.45-4.42 (m, 1H), 4.15 (d, J=2.1 Hz, 2H), 4.01-3.94 (m, 4H), 3.85 (d, J=12.3 Hz, 1H), 3.74 (t, J=7.1 Hz, 2H), 3.68-3.62 (m, 1H), 3.48-3.45 (m, 2H), 3.40-3.38 (m, 2H), 3.13-3.04 (m, 1H), 2.96-2.87 (m, 1H), 2.83 (t, J=2.1 Hz, 1H), 1.35 (t, J=7.1 Hz, 3H); MS ESI (m/z) 491 (M+1)$^+$, calc. 490.

Example 29

Preparation of (2S,3R,4R,5S,6R)-2-(4-chloro-5-(4-ethoxybenzyl)-2-(2-(2-hydroxyethoxy)ethyl)phenyl)-6-(hydroxymethyl)tetrahydro-2H-pyran-3,4,5-triol (Compound AP)

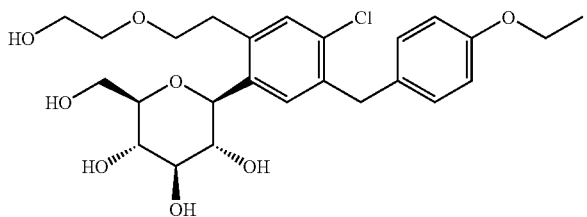

Compound AP was prepared using methods analogous to those described in Examples 20 and 21 above. $^1$H-NMR (CD$_3$OD, 300 MHz) δ 7.37 (s, 1H), 7.27 (s, 1H), 7.08 (d, J=8.7 Hz, 2H), 6.78 (d, J=8.7 Hz, 2H), 4.49-4.46 (m, 1H), 4.01-3.94 (m, 4H), 3.85 (dd, J=12.3, 1.5 Hz, 1H), 3.72-3.62 (m, 5H), 3.54-3.46 (m, 4H), 3.41-3.37 (m, 2H), 3.12-3.03 (m, 1H), 2.97-2.87 (m, 1H), 1.35 (t, J=7.1 Hz, 3H); MS ESI (m/z) 497 (M+1)$^+$, calc. 496.

Example 30

Figure 13:
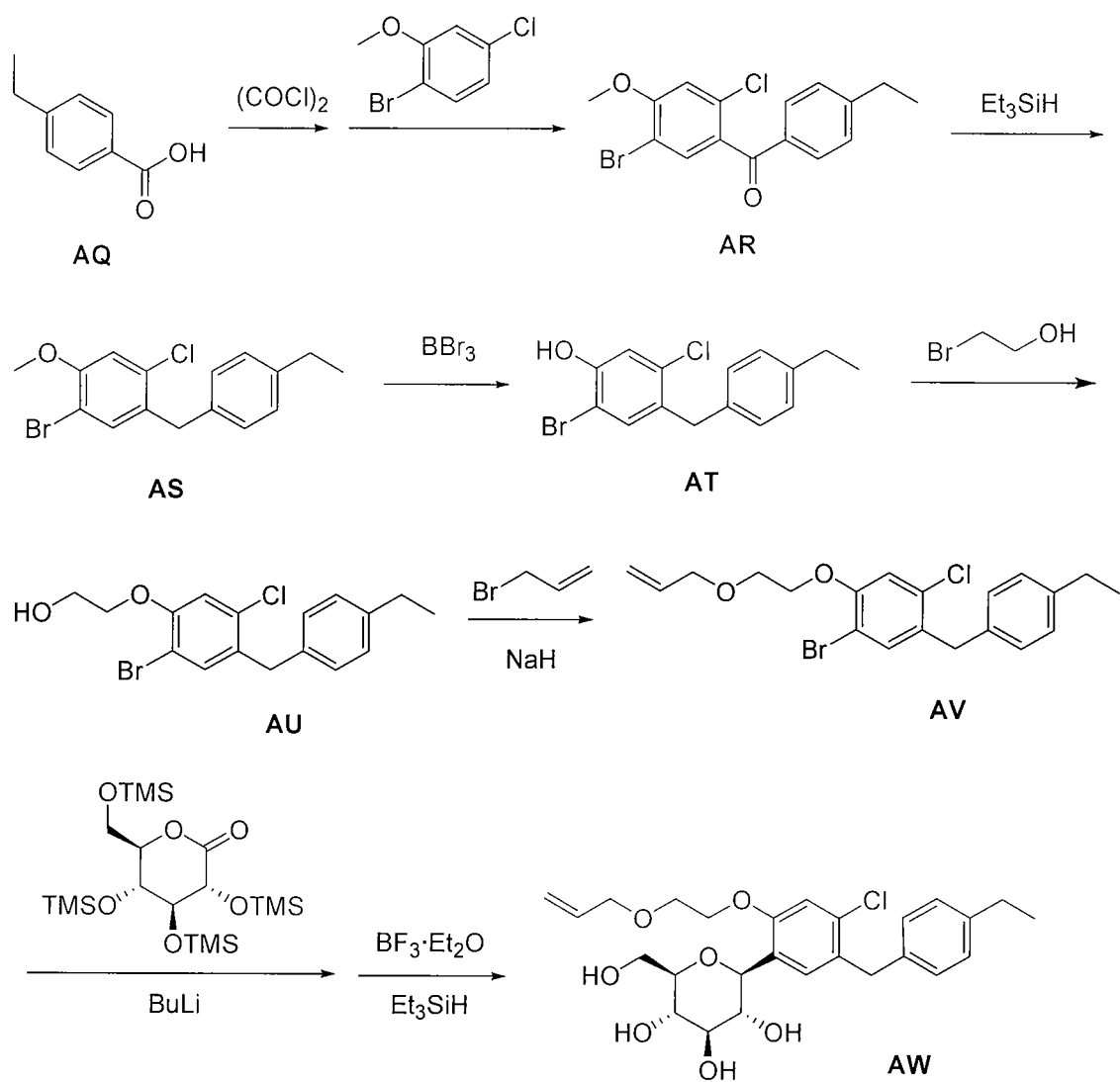

This example illustrates the preparation of compound AW according to the approach provided in FIG. 13. The general method is applicable to other compounds of the present invention.

Preparation of (5-bromo-2-chloro-4-methoxyphenyl)(4-ethylphenyl)methanone (Intermediate AR)

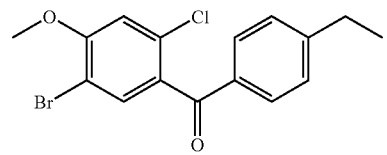

To a solution of 4-ethyl benzoic acid (AQ) (0.50 g, 3.33 mmol) in dry dichloromethane (20 mL) was added dropwise oxalyl chloride (0.32 mL, 3.68 mmol) followed by N,N-dimethylformamide (0.1 mL). After being stirred for 2 h at room temperature, the reaction mixture was evaporated and the residue was dissolved in dry dichloromethane (20 mL) at room temperature under agron. After cooling to −5° C., 1-bromo-4-chloro-2-methoxybenzene (0.6 g, 2.78 mmol) was added. Then AlCl$_3$ (0.43 g, 3.33 mmol) was added portionwise and the reaction temperature was kept between −5° C. and 0° C. After being stirred at room temperature for four hours, the reaction mixture was poured onto ice water and extracted with dichloromethane (80 mL). The combined organic layers were washed with 1 M HCl (10 mL), water (10 mL) and brine (10 mL), and then dried over anhydrous Na$_2$SO$_4$ Concentration under reduced pressure gave AR as a white solid. Yield: 0.5 g (52.3%). $^1$H-NMR (CDCl$_3$, 400 MHz): δ 7.75 (d, J=8.4 Hz, 2H), 7.60 (s, 1H), 7.32 (d, J=8.0 Hz, 2H), 6.98 (s, 1H), 3.99 (s, 3H), 2.76 (q, J=7.5 Hz, 2H), 1.29 (t, J=7.5 Hz, 3H).

Preparation of 1-bromo-4-chloro-5-(4-ethylbenzyl)-2-methoxybenzene (Intermediate AS)

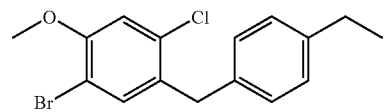

To a solution of (5-bromo-2-chloro-4-methoxyphenyl)(4-ethylphenyl)methanone (AR) (7.08 g, 20 mmol) in 2,2,2-trifluoroacetic acid (50 mL) was added triethylsilane (4.65 g, 40 mmol) under argon. After stirring for 10 min at room temperature, trifluoromethane-sulfonic acid (0.1 mL) was added. The reaction temperature was raised to reflux. After stirring for 2 h, TLC showed the reaction was complete. The reaction mixture was evaporated and the residue was dissolved in EtOAc (150 mL). The organic layer was washed with H$_2$O, NaHCO$_3$ and brine. After drying over anhydrous Na$_2$SO$_4$, it was filtered and concentrated to give AS as a yellow oil (6.18 g, yield 91%). $^1$H-NMR (CDCl$_3$, 300 MHz)

δ 7.33 (s, 1H), 7.13 (m, 4H), 6.92 (s, 1H), 3.99 (s, 2H), 3.87 (s, 3H), 2.52 (q, J=7.5 Hz, 2H), 1.23 (t, J=7.5 Hz, 3H).

Preparation of
2-bromo-5-chloro-4-(4-ethylbenzyl)phenol
(Intermediate AT)

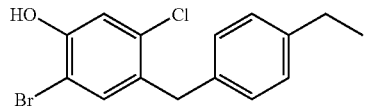

To a solution of 1-bromo-4-chloro-5-(4-ethylbenzyl)-2-methoxybenzene (AS) (5.1 g, 15 mmol) in anhydrous $CH_2Cl_2$ (15 mL), the solution of $BBr_3$ in $CH_2Cl_2$ (1M, 20 mL) was added dropwise at −5° C. After $BBr_3$ was added, the reaction mixture was allowed to warm to room temperature and stirred for 2 h, after which TLC showed the reaction was complete. The reaction was quenched with saturated $NaHCO_3$. The organic phase was separated and washed with water and brine. After drying with anhydrous $Na_2SO_4$, the organic portion was filtered and concentrated to give AT as an oil (4.49 g, yield 92%). $^1$H-NMR (CDCl$_3$, 300 MHz) δ 7.22 (s, 1H), 7.13 (m, 4H), 7.07 (s, 1H), 5.42 (s, 1H), 3.99 (s, 2H), 2.54 (q, J=7.5 Hz, 2H), 1.23 (t, J=7.5 Hz, 3H).

Preparation of 2-(2-bromo-5-chloro-4-(4-ethylbenzyl)phenoxy)ethanol (Intermediate AU)

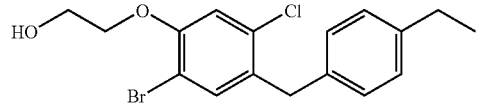

To a solution of 2-bromo-5-chloro-4-(4-ethylbenzyl)phenol (AT) (3.26 g, 10 mmol) in anhydrous DMF (15 mL), NaH (0.72 g, 30 mmol) was added in portions. The reaction mixture was stirred for 2 h at room temperature, and then 2-bromoethanol (3.75 g, 30 mmol) was added dropwise, and the reaction mixture was heated to 45° C. overnight. TLC showed the reaction was complete. The reaction was quenched with the saturated $NH_4Cl$, the mixture was extracted with EtOAc, and then washed with water and brine. After drying with anhydrous $Na_2SO_4$ the organic portion was filtered and concentrated. The residue was purified by flash chromatography to give AU as an oil (3.00 g, yield 81%). $^1$H-NMR (CDCl$_3$, 300 MHz) δ 7.32 (s, 1H), 7.13 (m, 4H), 6.94 (s, 1H), 4.11 (m, 2H), 3.57-3.99 (m, 4H), 2.64 (q, J=7.5 Hz, 2H), 1.22 (t, J=7.5 Hz, 3H).

Preparation of 1-(2-(allyloxy)ethoxy)-2-bromo-5-chloro-4-(4-ethylbenzyl)benzene (Intermediate AV)

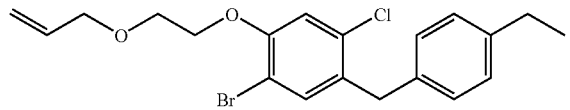

To a solution of 2-(2-bromo-5-chloro-4-(4-ethylbenzyl)phenoxy)ethanol (AU) (1.85 g, 5 mmol) in anhydrous DMF (10 mL), NaH (0.36 g 15 mmol) was added in portions, and the mixture was stirred at room temperature for 2 hours. Then allyl bromide (1.82 g, 15 mmol) was added dropwise, and the mixture was heated to 45° C. overnight. The reaction was quenched with the saturated $NH_4Cl$ and the mixture was extracted with EtOAc, and then washed with water and brine. After drying with anhydrous $Na_2SO_4$, the organic portion was filtered and concentrated. The residue was purified by flash chromatography to give AV as an oil (1.74 g, yield 85%). $^1$H-NMR (CDCl$_3$, 300 MHz) δ 7.31 (s, 1H), 7.13 (m, 4H), 6.94 (s, 1H), 5.94 (m, 1H), 5.26 (m, 2H), 4.14 (m, 4H), 3.96 (s, 2H), 3.84 (m, 2H), 2.64 (q, J=7.5 Hz, 2H), 1.22 (t, J=7.5 Hz, 3H).

Preparation of (2S,3R,4R,5S,6R)-2-(2-(2-(allyloxy)ethoxy)-4-chloro-5-(4-ethylbenzyl)phenyl)-6-(hydroxymethyl)tetrahydro-2H-pyran-3,4,5-triol (Compound AW)

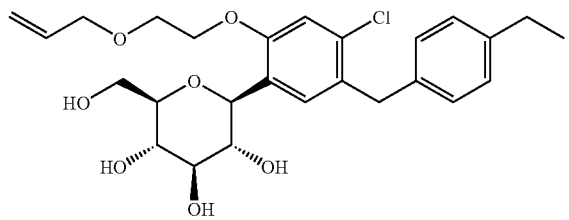

To a solution of 1-(2-(allyloxy)ethoxy)-2-bromo-5-chloro-4-(4-ethylbenzyl)benzene (AV) (1.74 g, 4.25 mmol) in anhydrous THF (10 mL) at −78° C., was added dropwise n-BuLi (2.9 M, 1.76 mL) and stirring was continued at −78° C. for 1 hour. The mixture was transferred to a solution of (3R,4S,5R,6R)-3,4,5-tris(trimethylsilyloxy)-6-((trimethylsilyloxy)methyl)-tetrahydropyran-2-one (2.18 g, 4.68 mmol) in anhydrous THF (10 mL) at −78° C., and stirring was continued at −78° C. for 2 hours until the starting material was consumed. After quenching with methanesulfonic acid (1 g in 10 mL MeOH), the mixture was allowed to warm to room temperature and stirred overnight. $H_2O$ (20 mL) was added, and the organic phase was separated. The aqueous phase was extracted with EtOAc. The combined organic phases were washed with saturated $NaHCO_3$, water and brine, and then dried with anhydrous $Na_2SO_4$, filtered and concentrated. The residue was purified by flash chromatography to provide crude product (0.8 g, $R_f$=0.1-0.2, EtOAc:PE=2:1). The crude product was dissolved in anhydrous $CH_3CN$ (10 mL), $Et_3SiH$ (1 mL) was added, the mixture was cooled to −5° C., and $BF_3 \cdot Et_2O$ (0.6 mL) was added dropwise. The reaction was allowed to warm to 20° C. and stirred overnight. After the reaction was complete, it was quenched with saturated aqueous $NaHCO_3$. The solvent was removed under vacuum and the residue was extracted with EtOAc and washed with water and brine. The residue was then dried with anhydrous $Na_2SO_4$, filtered and concentrated to give a solid, which was purified by preparative HPLC and freeze-dried to give final product AW as a white powder. $^1$H-NMR (CDCl$_3$, 300 MHz) δ 7.34 (s, 1H), 7.07 (s, 4H), 7.04 (s, 1H), 5.96 (m, 1H), 5.28~5.35 (m, 1H), 5.17~5.22 (m, 1H), 4.54 (d, J=9.0 Hz, 1H), 4.03~4.15 (m, 4H), 3.97 (d, J=2.1 Hz, 2H), 3.79~3.87 (m, 2H), 3.62~3.72 (m, 1H), 3.45~3.51 (1,2H), 3.35~3.44 (m, 2H), 3.29~3.31 (m, 4H), 2.56 (q, J=7.5 Hz, 2H), 1.18 (t, J=7.5 Hz, 3H).

Example 31

Preparation of (2S,3R,4R,5S,6R)-2-(2-((but-2-ynyloxy)methyl)-4-chloro-5-(4-ethylbenzyl)phenyl)-6-(hydroxymethyl)tetrahydro-2H-pyran-3,4,5-triol (Compound AX)

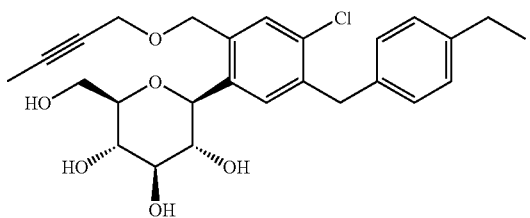

Compound AX was prepared using methods analogous to those described in Example 1 above. $^1$H-NMR (CD$_3$OD, 400 MHz) δ 7.47 (s, 1H), 7.42 (s, 1H), 7.11 (s, 4H), 4.84 (d, J=11.6 Hz, 1H), 4.59 (d, J=11.6 Hz, 1H), 4.51 (d, J=9.2 Hz, 1H), 4.18 (d, J=2.4 Hz, 2H), 4.10 (d, J=15.2 Hz, 1H), 4.05 (d, J=15.2 Hz, 1H), 3.88 (d, J=12.4 Hz, 1H), 3.71-3.67 (m, 1H), 3.52-3.41 (m, 4H), 2.61 (q, J=7.6 Hz, 2H), 1.90 (t, J=2.4 Hz, 3H), 1.21 (t, J=7.6 Hz, 3H); LC-MS (m/z) 475 [(M+1)$^+$], 492 [(M+18)$^+$], 519 [(M+45)$^-$].

Example 32

Preparation of (2S,3R,4R,5S,6R)-2-(2-((but-2-ynyloxy)methyl)-4-chloro-5-(4-ethoxybenzyl)phenyl)-6-(hydroxymethyl)tetrahydro-2H-pyran-3,4,5-triol (Compound AY)

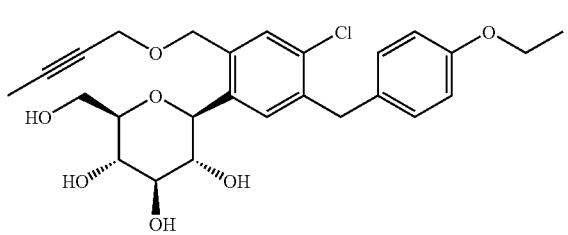

Compound AY was prepared using methods analogous to those described in Example 1 above. $^1$H-NMR (CD$_3$OD, 400 MHz) δ 7.45 (s, 1H), 7.38 (s, 1H), 7.08 (d, J=8.4 Hz, 2H), 6.78 (d, J=8.4 Hz, 2H), 4.80 (d, J=12.0 Hz, 1H), 4.56 (d, J=12.0 Hz, 1H), 4.48 (d, J=9.2 Hz, 1H), 4.15-4.16 (m, 2H), 4.00 (dd, J=14.8, 20.8 Hz, 2H), 3.96 (q, J=6.8 Hz, 2H), 3.86 (d, J=11.6 Hz, 1H), 3.64-4.69 (m, 1H), 3.39-3.48 (m, 4H), 1.87 (t, J=2.0 Hz, 3H), 1.34 (t, J=6.8 Hz, 3H); LC-MS (m/z) 491 [(M+1)$^+$], 535 [(M+45)$^-$].

Example 33

Preparation of (2S,3R,4R,5S,6R)-2-(2-(allyloxymethyl)-4-chloro-5-(4-ethoxybenzyl)phenyl)-6-(hydroxymethyl)tetrahydro-2H-pyran-3,4,5-triol (Compound AZ)

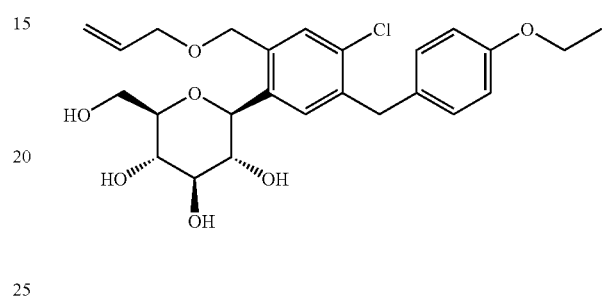

Compound AZ was prepared using methods analogous to those described in Example 1 above. $^1$H-NMR (CD$_3$OD, 400 MHz) δ 7.48 (s, 1H), 7.42 (s, 1H), 7.11 (s, 4H), 5.93-5.87 (m, 1H), 5.24 (dd, J=17.2, 1.6 Hz, 1H), 5.11 (dd, J=1.6, 10.4 Hz, 1H), 4.85 (d, J=12.0 Hz, 1H), 4.62 (d, J=12.0 Hz, 1H), 4.51 (d, J=9.2 Hz, 1H), 4.23 (s, 2H), 4.10 (d, J=14.8 Hz, 1H), 4.05 (d, J=14.8 Hz, 1H), 3.96 (q, J=6.8 Hz, 2H), 3.88 (d, J=12.4 Hz, 1H), 3.71-3.67 (m, 1H), 3.52-3.41 (m, 4H), 1.34 (t, J=6.8 Hz, 3H); LC-MS (m/z) 479 [(M+1)$^+$], 523 [(M+45)$^-$].

Example 34

Preparation of (2S,3R,4R,5S,6R)-2-(2-((but-2-ynyloxy)methyl)-4-chloro-5-(4-methoxybenzyl)phenyl)-6-(hydroxymethyl)tetrahydro-2H-pyran-3,4,5-triol (Compound BA)

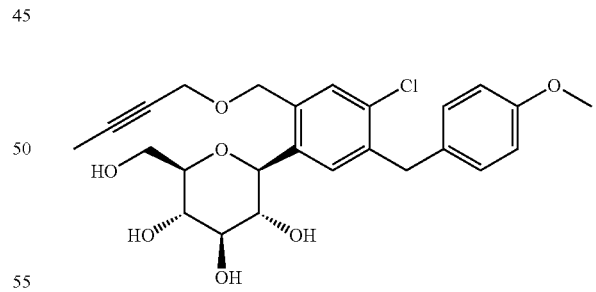

Compound BA was prepared using methods analogous to those described in Example 1 above. $^1$H-NMR (CD$_3$OD, 400 MHz) δ 7.45 (s, 1H), 7.38 (s, 1H), 7.08 (d, J=8.4 Hz, 2H), 6.78 (d, J=8.4 Hz, 2H), 4.80 (d, J=12.0 Hz, 1H), 4.56 (d, J=12.0 Hz, 1H), 4.48 ((1, J=9.2 Hz, 1H), 4.15-4.16 (m, 2H), 4.00 (dd, J=14.8, 20.8 Hz, 2H), 3.86 (d, J=11.6 Hz, 1H), 3.73 (s, 3H), 3.64-4.69 (m, 1H), 3.39-3.48 (m, 4H), 1.87 (t, J=2.0 Hz, 3H); LC-MS (m/z) 477 [(M+1)$^+$], 521 [(M+45)$^-$].

Example 35

Preparation of (2S,3R,4R,5S,6R)-2-(5-(4-(allyloxy)benzyl)-2-(allyloxymethyl)-4-chlorophenyl)-6-(hydroxymethyl)tetrahydro-2H-pyran-3,4,5-triol (Compound BB)

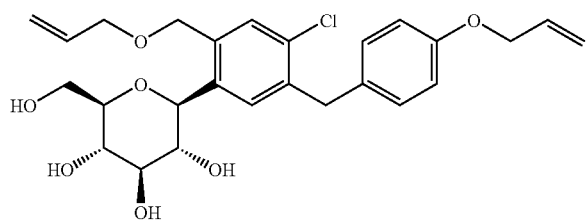

Compound BB was prepared using methods analogous to those described in Example 1 above. $^1$H-NMR (CD$_3$OD, 400 MHz) δ 7.48 (s, 1H), 7.42 (s, 1H), 7.11 (s, 4H), 5.93-5.87 (m, 2H), 5.24 (m, 4H), 4.85 (d, J=12.0 Hz, 1H), 4.62 (d, J=12.0 Hz, 1H), 4.60 (d, J=14.8 Hz, 1H), 4.55 (d, J=14.8 Hz, 1H), 4.51 (d, J=9.2 Hz, 1H), 4.23 (s, 2H), 4.10 (d, J=14.8 Hz, 1H), 4.05 (d, J=14.8 Hz, 1H), 3.88 (d, J=12.4 Hz, 1H), 3.71-3.67 (m, 1H), 3.52-3.41 (m, 4H); LC-MS (m/z) 491 [(M+1)+], 535 [(M+45)−].

Example 36

Preparation of (2S,3R,4R,5S,6R)-2-(2-((but-2-ynyloxy)methyl)-4-chloro-5-(4-hydroxybenzyl)phenyl)-6-(hydroxymethyl)tetrahydro-2H-pyran-3,4,5-triol (Compound BC)

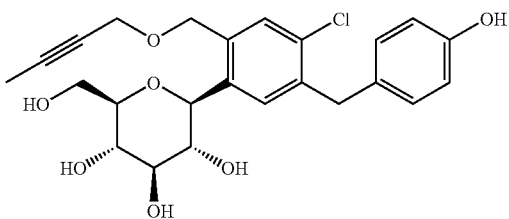

Compound BC was prepared using methods analogous to those described in Example 1 above. $^1$H-NMR (CD$_3$OD, 400 MHz) δ 7.45 (s, 1H), 7.38 (s, 1H), 7.08 (d, J=8.4 Hz, 2H), 6.78 (d, J=8.4 Hz, 2H), 4.80 (d, J=12.0 Hz, 1H), 4.56 (d, J=12.0 Hz, 1H), 4.48 (d, J=9.2 Hz, 1H), 4.15-4.16 (m, 2H), 4.00 (dd, J=14.8 Hz, 20.8 Hz, 2H), 3.86 (d, J=11.6 Hz, 1H), 3.64-4.69 (m, 1H), 3.39-3.48 (m, 4H), 1.87 (t, J=2.0 Hz, 3H); LC-MS (m/z) 463 [(M+1)+], 507 [(M+45)−].

Example 37

Preparation of ((2R,3S,4R,5R,6S)-6-(4-chloro-5-(4-ethylbenzyl)-2-((prop-2-ynyloxy)methyl)phenyl)-3,4,5-trihydroxytetrahydro-2H-pyran-2-yl)methyl acetate (Compound BD)

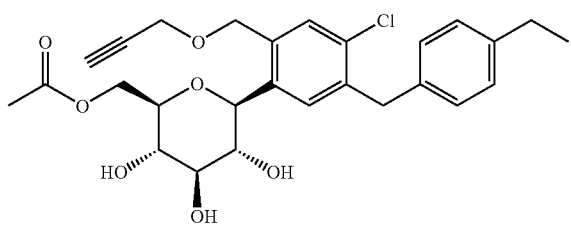

Compound BD was prepared using methods analogous to those described above as will be evident to those skilled in the art. $^1$H-NMR (CD$_3$OD, 400 MHz) δ 7.48 (s, 1H), 7.42 (s, 1H), 7.11 (s, 4H), 4.85 (d, J=12.0 Hz, 1H), 4.62 (d, J=12.0 Hz, 1H), 4.51 (d, J=9.2 Hz, 1H), 4.23 (s, 2H), 4.10 (d, J=14.8 Hz, 1H), 4.05 (d, J=14.8 Hz, 1H), 3.88 (d, J=12.4 Hz, 1H), 3.71-3.67 (m, 1H), 3.52-3.41 (m, 4H), 2.94 (s, 1H), 2.60 (q, J=7.6 Hz, 2H), 2.15 (s, 3H), 1.21 (t, J=7.6 Hz, 3H); LC-MS (m/z) 503 [(M+1)+], 547 [(M+45)−].

Example 38

Preparation of (2S,3R,4R,5S,6R)-2-(4-chloro-5-(4-ethylbenzyl)-2-(2-(prop-2-ynyloxy)ethoxy)phenyl)-6-(hydroxymethyl)tetrahydro-2H-pyran-3,4,5-triol (Compound BE)

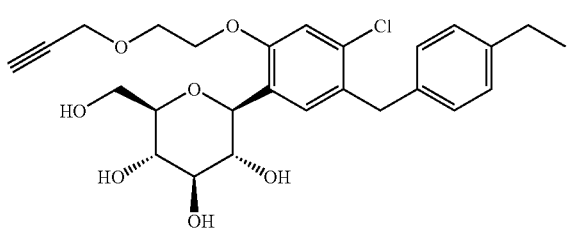

Compound BE was prepared using methods analogous to those described in Example 30 above. $^1$H-NMR (CD$_3$OD, 400 MHz) δ 7.36 (d, J=9.2 Hz, 1H), 7.10 (s, 4H), 7.05 (d, J=6.8 Hz, 1H), 5.51 (d, J=6.0 Hz, 1H), 4.21 (m, 1H), 4.08 (m, 1H), 4.01 (m, 2H), 3.84~3.96 (m, 3H), 3.68 (m, 1H), 3.39~3.54 (m, 4H), 3.33 (m, 3H), 2.61 (dd, J=7.6 Hz, 2H), 1.21 (t, J=7.6 Hz, 3H); LC-MS (m/z) 491 [(M+1)+], 535 [(M+45)−].

Example 39

Preparation of (2S,3R,4R,5S,6R)-2-(2-(2-(but-2-ynyloxy)ethoxy)-4-chloro-5-(4-ethylbenzyl)phenyl)-6-(hydroxymethyl)tetrahydro-2H-pyran-3,4,5-triol (Compound BF)

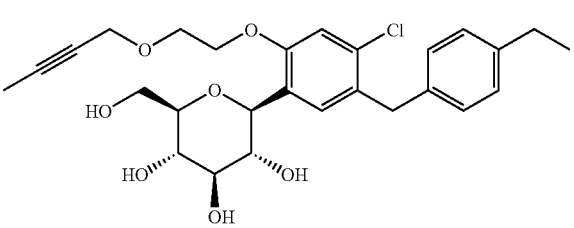

Compound BF was prepared using methods analogous to those described in Example 30 above. $^1$H-NMR (CD$_3$OD, 400 MHz) δ 7.35 (s, 1H), 7.10 (s, 4H), 7.04 (s, 1H), 4.63 (m, 1H), 4.23 (m, 2H), 4.13 (m, 2H), 4.00 (m, 2H), 3.84~3.89 (m, 3H), 3.67 (m, 1H), 3.48~3.50 (m, 2H), 3.40 (m, 2H), 2.59 (dd, J=7.6 Hz, 2H), 1.85 (t, J=2.4 Hz, 3H), 1.20 (t, J=7.6 Hz, 31H); LC-MS (m/z) 505 [(M+1)+], 522 [(M+18)+], 549 [(M+45)−].

Example 40

Preparation of (2S,3R,4R,5S,6R)-2-(4-chloro-2-(2-(cyclopentyloxy)ethoxy)-5-(4-ethylbenzyl)phenyl)-6-(hydroxymethyl)tetrahydro-2H-pyran-3,4,5-triol (Compound BG)

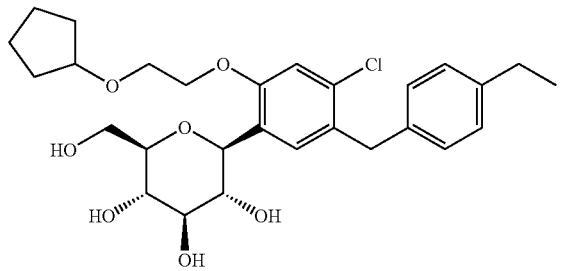

Compound BG was prepared using methods analogous to those described in Example 30 above. $^1$H-NMR (CD$_3$OD, 400 MHz) δ 7.35 (s, 1H), 7.09 (s, 4H), 7.06 (s, 1H), 4.64 (m, 1H), 4.11 (m, 2H), 4.08 (m, 1H), 4.01 (d, J=3.2 Hz, 2H), 3.84~3.87 (m, 1H), 3.78 (m, 2H), 3.65~3.69 (m, 1H), 3.48 (m, 2H), 3.39 (m, 2H), 2.60 (dd, J=7.6 Hz, 2H), 1.72~1.81 (m, 6H), 1.57~1.59 (m, 2H), 1.20 (t, J=7.6 Hz, 3H); LC-MS (m/z) 521 [(M+1)$^+$], 565 [(M+45)$^-$].

Example 41

Preparation of (2S,3R,4R,5S,6R)-2-(4-chloro-5-(4-ethoxybenzyl)-2-(2-(2-fluoroethoxy)ethyl)phenyl)-6-(hydroxymethyl)tetrahydro-2H-pyran-3,4,5-triol (Compound BH)

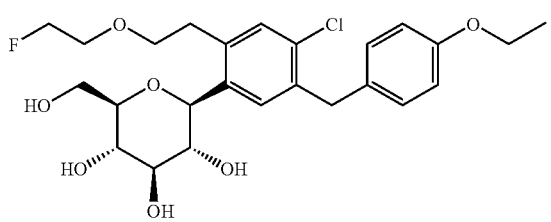

Compound BH was prepared using methods analogous to those described in Examples 9 and 20 above. $^1$H-NMR (CD$_3$OD, 300 MHz) δ 7.38 (s, 1H), 7.26 (s, 1H), 7.08 (d, J=6.9 Hz, 2H), 6.78 (d, J=6.9 Hz, 2H), 4.58 (m, 1H), 4.43 (m, 2H), 3.98 (m, 4H), 3.85 (m, 1H), 3.68 (m, 5H), 3.47 (m, 4H), 3.07 (m, 1H), 2.93 (m, 1H), 1.35 (t, J=7.2 Hz, 3H); MS ESI$^+$ (m/z) 499 (M+1)$^+$, 516 (M+18)$^+$; ESI$^-$ $^{(m/z)}$ 543 (M+45)$^-$.

Example 42

Figure 14:
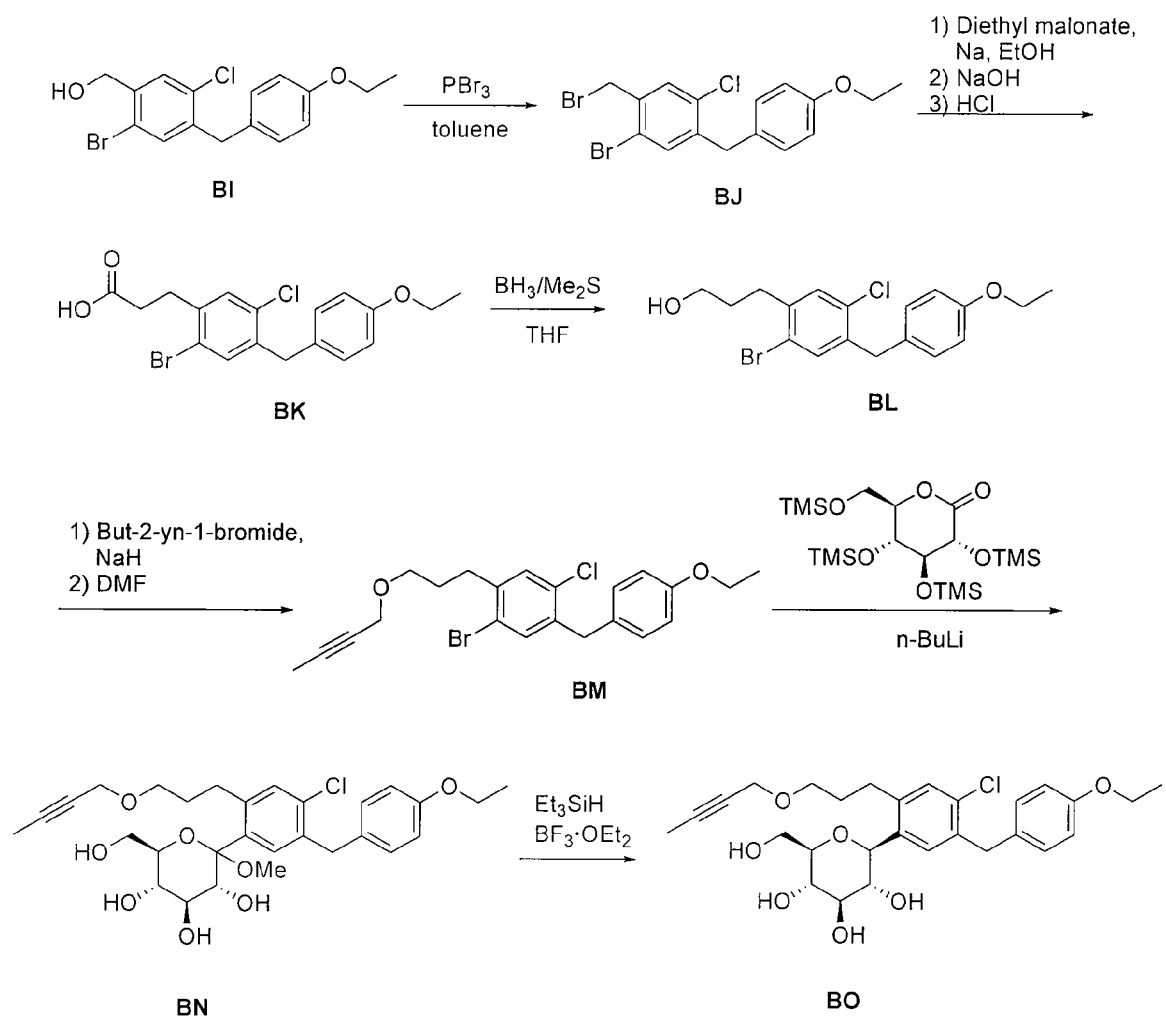

This example illustrates the preparation of compound BO according to the approach provided in FIG. 14. The general method is applicable to other compounds of the present invention.

Preparation of (2-bromo-5-chloro-4-(4-ethoxybenzyl)phenyl)methanol (Intermediate BI)

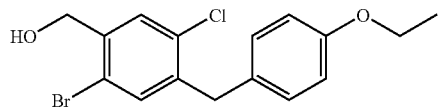

Intermediate BI was prepared using methods analogous to those described in Example 1 above by substituting ethoxybenzene for ethylenzene in the preparation of intermediate F.

Preparation of 1-bromo-2-(bromomethyl)-4-chloro-5-(4-ethoxybenzyl)benzene (Intermediate BJ)

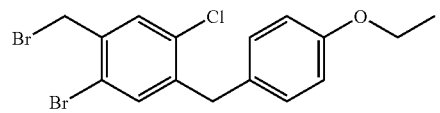

To a stirred 0° C. solution of intermediate BI (3.12 g, 8.776 mmol) in toluene (20 mL) was added PBr$_3$ (0.91 mL, 9.654 mmol). After addition, the mixture was heated to 100° C. and stirred for 4.5 h. An additional 0.2 mL of PBr$_3$ was added and the solution was continuously stirred for 4 h at 100° C. The mixture was cooled to room temperature and quenched by the addition of 20 mL of water. The resultant solution was extracted with ethyl acetate (30 mL×3), and the combined organic layers were washed with water and brine, and then dried over Na$_2$SO$_4$. After removal of volatiles, the residue was purified by column chromatography (eluting with EtOAc:PE=1:30) to obtain 2.8 g of intermediate BJ.

Preparation of 3-(2-bromo-5-chloro-4-(4-ethoxybenzyl)phenyl)propanoic acid (Intermediate BK)

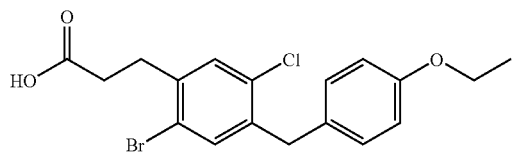

A solution of NaOEt (freshly prepared from 0.84 g Na and 10 mL of ethanol) was added to diethyl malonate (5.53 mL, 0.036 mol) in 10 mL of ethanol. After stirring for 1 h at room temperature, the resulting solution was added to a suspension of 1-bromo-2-(bromomethyl)-4-chloro-5-(4-ethoxybenzyl)benzene (BJ) (2.8 g, 0.0067 mol) in 10 mL of ethanol and heated to 80° C. overnight. The ethanol was removed by distillation. The remaining solution was cooled to 0° C., diluted with water, and acidified to pH 2 with conc. HCl. The aqueous solution was extracted with ethyl acetate, and the organic layer was washed with water and brine, dried over Na$_2$SO$_4$, concentrated, and the residue was taken up in 40 mL of ethanol and 50 mL of aqueous NaOH solution. The mixture was heated to reflux for 4 h, and then the ethanol was removed by distillation. The solution was cooled to 0° C., acidified with 50 mL of conc. HCl and then heated to reflux overnight.

The solution was basified to pH 12 and extracted with ethyl acetate. The aqueous solution was acidified to pH 2 and the precipitate collected. The filter cake was washed with water and dried under vacuum to obtain 1.07 g of intermediate BK.

Preparation of 3-(2-bromo-5-chloro-4-(4-ethoxybenzyl)phenyl)propan-1-ol (Intermediate BL)

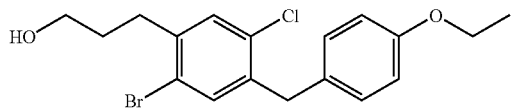

To a stirred 0° C. solution of 3-(2-bromo-5-chloro-4-(4-ethoxybenzyl)phenyl) propanoic acid (BK) (0.5 g, 1.26 mmol) in 8 mL of THF was added $BH_3$ in $Me_2S$ (2M, 3.15 mL, 6.29 mmol). After stirring for 30 min at 0° C., the mixture was warmed to room temperature and stirred overnight. The reaction solution was slowly quenched with dropwise addition of water until no more gas evolved. The reaction mixture was taken up in 20 mL of ethyl acetate, washed with saturated $Na_2CO_3$, water and brine, and then dried over $Na_2SO_4$, filtered and concentrated to obtain 0.268 g of crude intermediate BL, which was used in the next step without further purification.

Preparation of 1-bromo-2-(3-(but-2-ynyloxy)propyl)-4-chloro-5-(4-ethoxybenzyl)benzene (Intermediate BM)

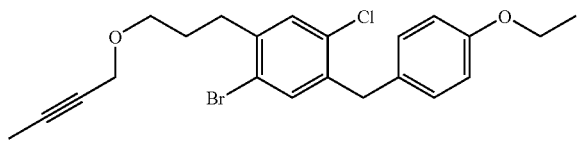

To a stirred solution of 3-(2-bromo-5-chloro-4-(4-ethoxybenzyl)phenyl)propan-1-ol (BL) (0.268 g, 0.70 mmol) in 5 mL of THF was added NaH (0.034 g, 0.84 mmol, 60%) and stirred for 40 min. 1-bromo-2-butyne (0.094 mL, 1.05 mmol) was added and the mixture was stirred overnight at room temperature. The reaction was quenched with water and extracted with ethyl acetate. The combined organic layers were washed with water and brine, dried over $Na_2SO_4$, concentrated and purified by preparative TLC (eluting with EtOAc:PE=1:10) to obtain 0.2 g of intermediate BM.

Preparation of (3R,4S,5S,6R)-2-(2-(3-(but-2-ynyloxy)propyl)-4-chloro-5-(4-ethoxybenzyl)phenyl)-6-(hydroxymethyl)-2-methoxytetrahydro-2H-pyran-3,4,5-triol (Intermediate BN)

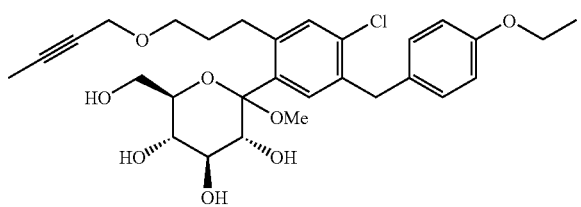

To a stirred −78° C. solution of 1-bromo-2-(3-(but-2-ynyloxy)propyl)-4-chloro-5-(4-ethoxybenzyl)benzene (BM) (0.2 g, 0.459 mmol) in 3 mL of 1:2 dry THF:toluene under Ar was added 0.22 mL of 2.5M n-BuLi in hexane (precooled to −78° C.) dropwise to insure the temperature remained below −70° C. After stirring for 40 min, the solution was transferred by cannula to a stirred −78° C. solution of (3R,4S,5R,6R)-3,4,5-tris(trimethylsilyloxy)-6-((trimethylsilyloxy)methyl)-tetrahydropyran-2-one (0.279 g, 0.597 mmol) in 2.5 mL of toluene at a rate that maintained the reaction below −70° C. The mixture was stirred for 3 h at −78° C. prior to addition of $MeSO_3H$ (0.093 g, 0.964 mmol) in 2.5 mL of methanol below −75° C. After complete addition, the reaction solution was gradually warmed to room temperature and stirred overnight. After quenching by saturated aq. $NaHCO_3$, the aqueous layer was extracted twice with EtOAc. The combined organic portions were washed with brine and dried over $Na_2SO_4$. After concentration, the residue was purified by preparative TLC (eluting with EtOAc:PE=1:5) to obtain 0.11 g of intermediate BN.

Preparation of (2S,3R,4R,5S,6R)-2-(2-(3-(but-2-ynyloxy)propyl)-4-chloro-5-(4-ethoxybenzyl)phenyl)-6-(hydroxymethyl)tetrahydro-2H-pyran-3,4,5-triol (Compound BO)

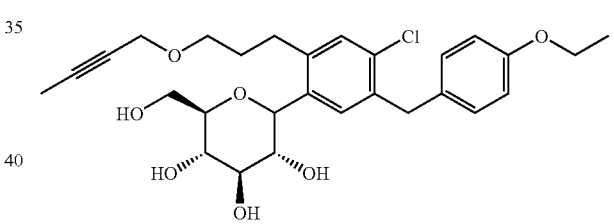

To a −20° C. solution of intermediate BN (0.11 g) in 3 mL of 1:1 anhydrous $CH_3CN:CH_2Cl_2$ was added $Et_3SiH$ (0.13 mL, 0.802 mmol). Then $BF_3.Et_2O$ (0.076 mL, 0.601 mmol) was added dropwise. After addition, the mixture was stirred for 3.5 h at −15° C., and then the reaction was quenched with saturated aqueous $NaHCO_3$. The volatiles were removed under reduced pressure, and the residue was extracted with EtOAc. The combined organic portions were washed with water and brine, dried over anhydrous $Na_2SO_4$, concentrated, and purified by preparative LC-MS to obtain compound BO (0.045 g). $^1$H-NMR ($CD_3OD$): δ 7.38 (s, 1H), 7.22 (s, 2H), 7.11~7.08 (d, J=11.6 Hz, 2H), 6.81~6.78 (d, J=11.6 Hz 1H), 4.44 (d, J=9.2 Hz, 2H), 4.10 (q, J=4.8, 2 Hz, 2H), 4.01~3.96 (m, 4H), 3.87~3.84 (m, 1H), 3.68~3.64 (m, 1H), 3.52~3.48 (m, 4H), 3.41~3.39 (m, 2H), 2.89~2.84 (dt, 1H), 2.74~2.69 (dt, 1H), 1.90~1.82 (m, 5H), 1.37~1.34 (t, J=7.2 Hz, 3H); MS ESI (m/z): 519 $(M+H)^+$.

Example 43

In Examples 43 and 44, the structures of compounds synthesized were confirmed using the following procedures: $^1$H-NMR data were acquired on a Varian Mercury 300 spectrometer at 300 MHz, with chemical shifts referenced to internal TMS. Liquid chromatography electrospray ionization mass spectrometry (LC-ESI-MS) analysis was performed on instrumentation consisting of Shimadzu LC-10AD vp series HPLC pumps and dual wavelength UV detector, a Gilson 215 autosampler, a Sedex 75c evaporative light scattering (ELS) detector, and a PE/Sciex API 150EX mass spectrometer. The ELS detector was set to a temperature of 40° C., a gain setting of 7, and a $N_2$ pressure of 3.3 atm. The Turbo IonSpray source was employed on the API 150 with an ion spray voltage of 5 kV, a temperature of 300° C., and orifice and ring voltages of 5 V and 175 V respectively. Positive ions were scanned in Q1 from 160 to 650 m/z. 5.0 μL injections were performed for each sample, on a Phenomenex Gemini 5 μm C18 column. Mobile phases consisted of 0.05% formic acid in both HPLC grade water (A) and HPLC grade acetonitrile (B) using the following gradients with a flow rate of 2 mL/min: 0.00 min, 95% A, 5% B; 4.00 min, 0% A, 100% B; 5.80 min, 0% A, 100% B; 6.00 min, 95% A, 5% B; 7.00 min, 95% A, 5% B.

Preparation of 1-bromo-4-chloro-5-(4-ethylbenzyl)-2-(2-(trifluoromethoxy)-ethoxy)benzene (Intermediate BP)

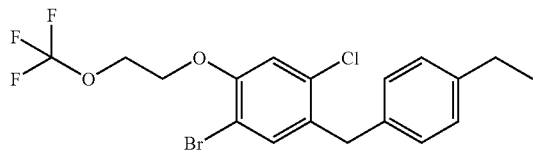

To a solution of 2-bromo-5-chloro-4-(4-ethylbenzyl)phenol (AT) (0.12 g, 0.38 mmol) in anhydrous $CH_3CN$ (4 mL), was added potassium tert-butoxide [1.0 M solution in tert-butanol] (380 μL, 0.38 mmol) followed by 2-(trifluoromethoxy)ethyl trifluoromethanesulfonate (0.10 g, 0.38 mmol) [prepared as described in the *Journal of Organic Chemistry*, 2001, 66, 1061-1063]. The reaction mixture was stirred for 15 h at room temperature, after which saturated $NH_4Cl$ was added and the mixture was partitioned between EtOAc and brine. The organic layer was dried with anhydrous $Na_2SO_4$, filtered and concentrated. The residue was purified by preparative TLC to give intermediate BP (0.06 g, 36%). $^1$H-NMR (CDCl$_3$, 300 MHz) δ 7.31 (s, 1H), 7.10 (m, 4H), 6.89 (s, 1H), 4.31 (m, 2H), 4.20 (m, 2H), 3.96 (2H), 2.61 (q, J=7.5 Hz, 2H), 1.22 (t, J=7.5 Hz, 3H).

Preparation of (2S,3R,4R,5S,6R)-2-(4-chloro-5-(4-ethylbenzyl)-2-(2-(trifluoromethoxy)ethoxy)phenyl)-6-(hydroxymethyl)tetrahydro-2H-pyran-3,4,5-triol (Compound BQ)

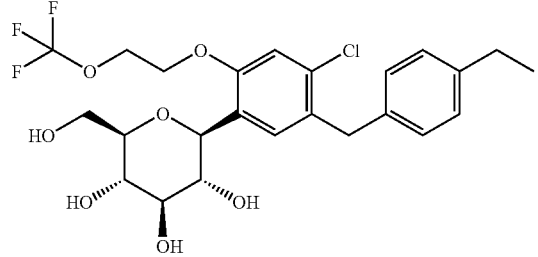

To a solution of 1-bromo-4-chloro-5-(4-ethylbenzyl)-2-(2-(trifluoromethoxy)-ethoxy)benzene (BP) (60 mg, 0.14 mmol) and (3R,4S,5R,6R)-3,4,5-tris(trimethylsilyloxy)-6-((trimethylsilyloxy)methyl)-tetrahydropyran-2-one (0.19 g, 0.41 mmol) in anhydrous THF (2 mL), was added n-BuLi (2.5 M, 0.11 mL) in a dropwise fashion at −78° C. over 15 min. The resulting solution was stirred at −78° C. for 1 h. Methanesulfonic acid (20 μL in 0.5 mL MeOH) was added and the mixture was allowed to warm to room temperature and stirred overnight. The reaction mixture was partitioned between EtOAc and saturated NaHCO$_3$. The organic layer was dried with anhydrous Na$_2$SO$_4$, filtered and concentrated. The residue was purified by preparative TLC eluting with 5% MeOH in CH$_2$Cl to collect the crude product. To a solution of the crude product (10 mg, 0.018 mmol) in anhydrous CH$_2$Cl$_2$ (2 mL) at 0° C. was added Et$_3$SiH (6.3 mg, 0.05 mmol) and BF$_3$.Et$_2$O (3.7 mg, 0.05 mmol). After stirring the resulting mixture for 1 h at 0° C., it was partitioned between water and EtOAc. The organic layer was dried over Na$_2$SO$_4$ and evaporated under vacuum. The residue was purified by preparative HPLC to give compound BQ. $^1$H-NMR (CDCl$_3$, 300 MHz) δ 7.21 (s, 1H), 7.07 (m, 4H), 6.89 (s, 1H), 4.29 (d, J=3.9 Hz, 1H), 4.17 (m, 2H), 4.01 (m, 2H), 3.81 (m, 2H), 3.76 (m, 1H), 3.74-3.49 (m, 6H), 2.61 (m, 3H), 1.20 (m, 3H).

Example 44

Preparation of 1-bromo-4-chloro-5-(4-ethylbenzyl)-2-(2-(2,2,2-trifluoroethoxy)ethoxy)benzene (Intermediate BR)

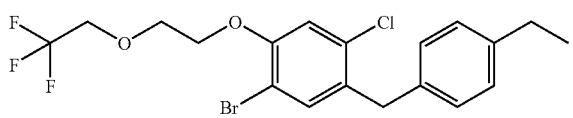

To a solution of 2-(2-bromo-5-chloro-4-(4-ethylbenzyl)phenoxy)ethanol (AU) (0.53 g, 1.4 mmol) in anhydrous CH$_2$Cl$_2$ (4 mL), was added 2,2,2-trifluoroethanol (0.43 g, 4.3 mmol) and triphenylphosphine polystyrene resin (0.57 g, 2.2 mmol). The resulting mixture was stirred overnight at room temperature, after which it was heated for 2 h at 45° C. The mixture was absorbed onto Celite and purified using silica gel column chromatography eluting with a gradient of EtOAc in hexanes to give intermediate BR. $^1$H-NMR (CDCl$_3$, 300 MHz) δ 7.36 (s, 1H), 7.14 (m, 4H), 6.94 (s, 1H), 4.17-4.01 (m, 8H), 2.67 (q, J=7.5 Hz, 2H), 1.27 (t, J=7.5 Hz, 3H).

Preparation of (2S,3R,4R,5S,6R)-2-(4-chloro-5-(4-ethylbenzyl)-2-(2-(2,2,2-trifluoroethoxy)ethoxy)phenyl)-6-(hydroxymethyl)tetrahydro-2H-pyran-3,4,5-triol (Compound BS)

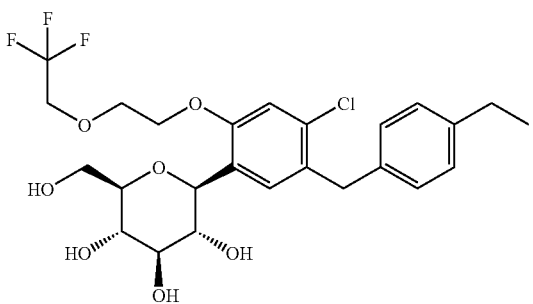

To a solution of 1-bromo-4-chloro-5-(4-ethylbenzyl)-2-(2-(2,2,2-trifluoroethoxy)ethoxy)benzene (BR) (96 mg, 0.21 mmol) and (3R,4S,5R,6R)-3,4,5-tris(trimethylsilyloxy)-6-((trimethylsilyloxy)methyl)-tetrahydropyran-2-one (0.20 g, 0.43 mmol) in anhydrous THF (3 mL), was added n-BuLi (1.6 M, 0.40 mL) in a dropwise fashion at −78° C. over 15 min. The resulting solution was stirred at −78° C. for 30 min. After quenching with methanesulfonic acid (61 µL in 1.0 mL MeOH), the mixture was allowed to warm to room temperature and stirred overnight. The reaction mixture was filtered through silica and purified by preparative TLC eluting with 7% MeOH in CH$_2$Cl$_2$ to collect the crude product. To a solution of the crude product in a mixture of 1:1 CH$_3$CN:CH$_2$Cl$_2$ (4 mL) was added Et$_3$SiH (200 µL), followed by cooling to −40° C. To the cooled mixture was added BF$_3$.Et$_2$O (40 µL), and it was allowed to warm to 0° C. over 2 h. Triethylamine (100 µL) was then added, the mixture was evaporated, and the residue was purified by preparative HPLC to give compound BS. $^1$H-NMR (CD$_3$OD, 300 MHz) δ 7.32 (s, 1H), 7.04 (m, 5H), 4.59 (d, J=9.3 Hz, 1H), 416-3.96 (m, 8H), 3.66-3.30 (m, 7H), 2.57 (q, J=7.5, 2H), 1.19 (t, J=7.2 Hz, 3H); MS ESI m/z 532.8 (M−1).

Example 45

Figure 15:
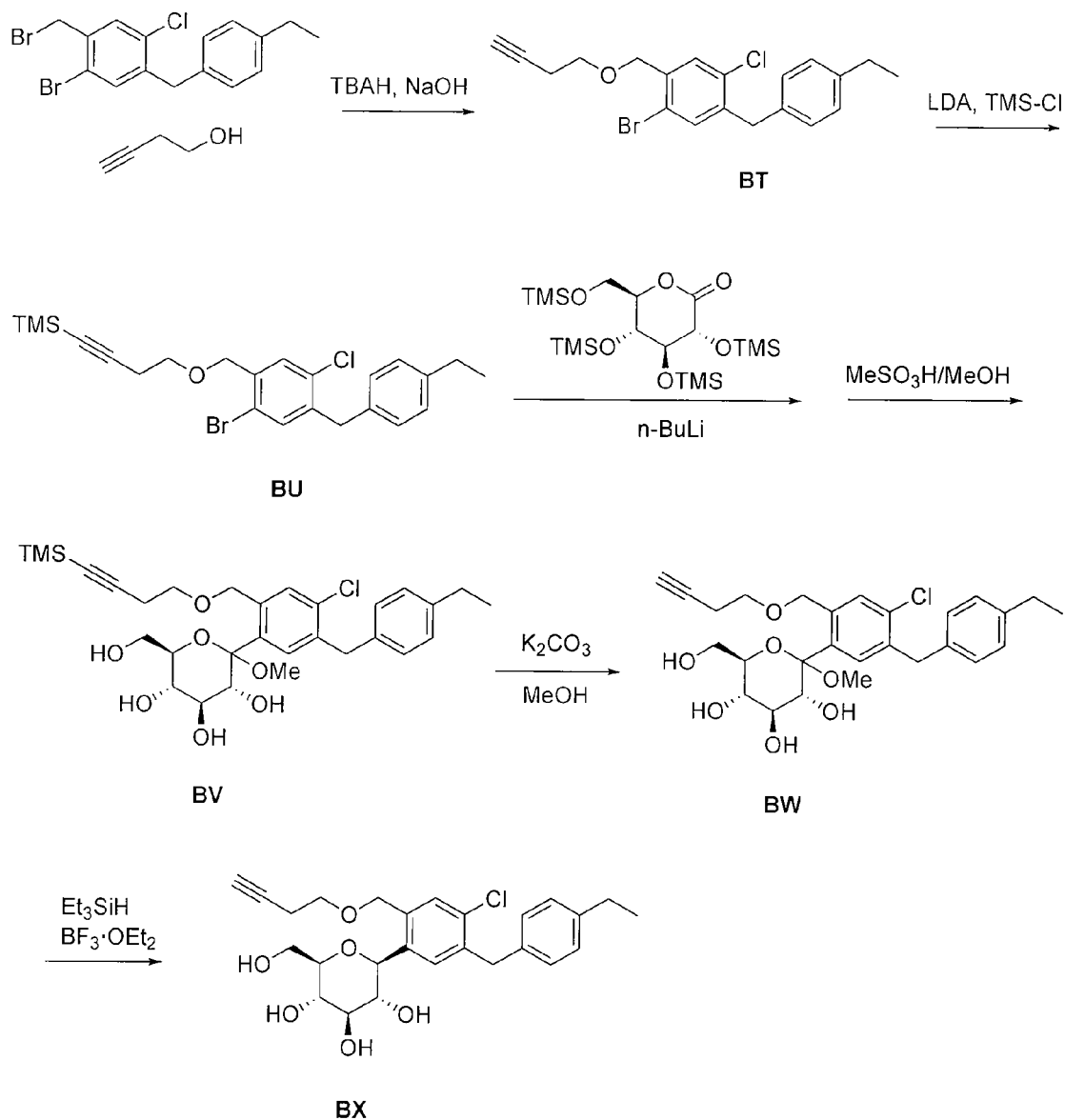

This example illustrates the preparation of compound BX according to the approach provided in FIG. 15. The general method is applicable to other compounds of the present invention.

Preparation of 1-bromo-2-((but-3-ynyloxy)methyl)-4-chloro-5-(4-ethylbenzyl)benzene (Intermediate BT)

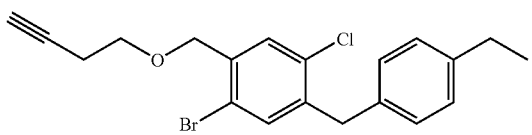

To a solution of 1-bromo-2-(bromomethyl)-4-chloro-5-(4-ethylbenzyl)benzene (200 mg, 0.497 mmol) in toluene (2 mL) was added NaOH (60 mg, 1.5 mmol), but-3-yn-1-ol (53 mg, 1.17 mmol) and TBAI (8.5 mg, 0.023 mmol) successively. After stirring overnight at 70° C., the solution was diluted with water. The solution was extracted with ethyl acetate and the extracts were washed with a saturated solution of NH$_4$Cl, followed by drying over Na$_2$SO$_4$. The solution was concentrated and the resulting residue was purified by preparative TLC to afford 96 mg of title product.

Preparation of (4-(2-bromo-5-chloro-4-(4-ethylbenzyl)benzyloxy)but-1-ynyl)trimethylsilane (Intermediate BU)

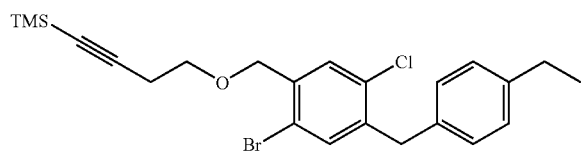

To a cooled solution (−78° C.) of 1-bromo-2-((but-3-ynyloxy)methyl)-4-chloro-5-(4-ethylbenzyl)benzene (BT) (96 mg, 0.245 mmol) was added LDA (2M in THF, 0.18 mL, 0.36 mmol). After stirring for 20 min, TMS-Cl (50 µL, 0.393 mmol) was added. After stirring for another 2.5 h, additional TMS-Cl (30 µL, 0.236 mmol) was added. The reaction solution was stirred at −78° C. for 70 min and then warmed to room temperature with stirring for 1.5 h. Water was added and the mixture was extracted with ethyl acetate and the extracts were washed with brine, and dried over Na$_2$SO$_4$. The solution was concentrated and the resulting residue was purified by preparative TLC to afford 72 mg of title product.

Preparation of (3R,4S,5S,6R)-2-(4-chloro-5-(4-ethylbenzyl)-2-((4-(trimethylsilyl)but-3-ynyloxy)methyl)phenyl)-6-(hydroxymethyl)-2-methoxytetrahydro-2H-pyran-3,4,5-triol (Intermediate BV)

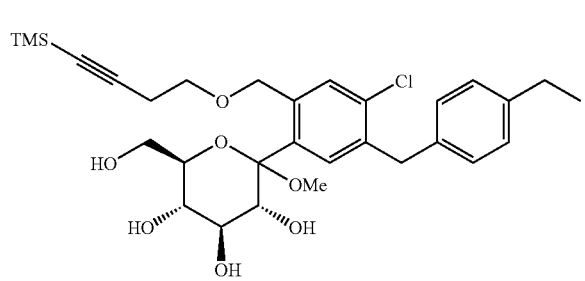

(4-(2-bromo-5-chloro-4-(4-ethylbenzyl)benzyloxy)but-1-ynyl)trimethylsilane (BU) (72 mg) was condensed with (3R,4S,5R,6R)-3,4,5-tris(trimethylsilyloxy)-6-((trimethylsilyloxy)methyl)-tetrahydropyran-2-one using methods analogous to those for the preparation of intermediate H described in Example 1 above. From this procedure 94 mg of crude title product was obtained. LC-MS (m/z): 621 [M+HCO$_2$]$^-$.

Preparation of (3R,4S,5S,6R)-2-(2-((but-3-ynyloxy)methyl)-4-chloro-5-(4-ethylbenzyl)phenyl)-6-(hydroxymethyl)-2-methoxytetrahydro-2H-pyran-3,4,5-triol (Intermediate BW)

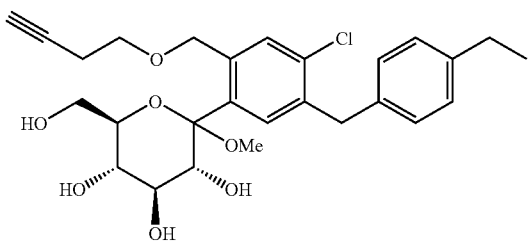

To a solution of the crude product from the previous step (BV) in MeOH (1 mL) was added $K_2CO_3$ (33 mg, 0.239 mmol). The mixture was stirred overnight and then the volatiles were removed. The resulting residue was taken up with water, the solution was extracted with ethyl acetate and the extracts were washed with brine, followed by drying over $Na_2SO_4$. The solution was concentrated and the resulting residue was purified by preparative HPLC to afford 12 mg of title product. LC-MS (m/z): 549 [M+HCO$_2$]$^-$.

Preparation of (2S,3R,4R,5S,6R)-2-(2-((but-3-ynyloxy)methyl)-4-chloro-5-(4-ethylbenzyl)phenyl)-6-(hydroxymethyl)tetrahydro-2H-pyran-3,4,5-triol (Compound BX)

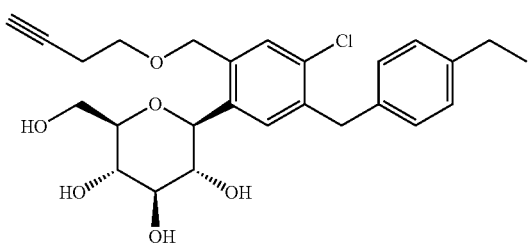

To a cooled solution (−30° C.) of (3R,4S,5S,6R)-2-(2-((but-3-ynyloxy)methyl)-4-chloro-5-(4-ethylbenzyl)phenyl)-6-(hydroxymethyl)-2-methoxytetrahydro-2H-pyran-3,4,5-triol (BW) (12 mg, 0.0238 mmol) in 0.5 mL of 1:1 $CH_2Cl_2$:$CH_3CN$ was added $Et_3SiH$ (16 μL, 0.1 mmol) followed by addition of $BF_3 \cdot OEt_2$ (10 μL, 0.0789 mmol). After stirring for about 4 h, the reaction was quenched with a saturated solution of $NaHCO_3$. The solution was extracted with ethyl acetate and the extracts were washed with brine, followed by drying over $Na_2SO_4$. The solution was concentrated and the resulting residue was purified by preparative HPLC to afford 3.5 mg of title product. $^1$H-NMR (CD$_3$OD, 400 MHz) δ 7.47 (s, 1H), 7.45 (s, 1H), 7.10 (s, 4H), 4.80 (d, J=12.4 Hz, 1H), 4.61 (d, J=12.4 Hz, 1H), 4.49 (d, J=8.8 Hz, 1H), 4.10 (d, J=15.0 Hz, 1H), 4.05 (d, J=15.0 Hz, 1H), 3.88 (dd, J=12.0, 2.0 Hz, 1H), 3.70-3.64 (m, 3H), 3.50 (t, J=8.4 Hz, 1H), 3.46-3.40 (m, 3H), 2.60 (q, J=7.4 Hz, 2H), 2.53-2.49 (m, 2H), 2.30 (t, J=2.6 Hz, 1H), 1.21 (t, J=7.4 Hz, 3H); LC-MS (m/z): 475 [M+H]$^+$, 519 [M+HCO$_2$]$^-$.

Example 46

Preparation of (2R,3R,4R,5S,6S)-3,4,5-tris(benzyloxy)-2-(benzyloxymethyl)-6-(4-chloro-5-(4-ethylbenzyl)-2-((2-fluoroethoxy)methyl)phenyl)tetrahydro-2H-pyran (Intermediate BY)

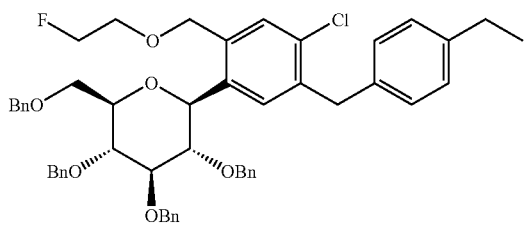

To a solution of 2-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)ethanol (intermediate O-3) (60 mg, 0.07 mmol) in 5 mL of $CH_2Cl_2$ at −78° C., was added dropwise DAST (17 mg, 0.011 mmol). The resulting solution was slowly warmed to room temperature and stirred for 3 h. The reaction was quenched by addition of MeOH (2 mL), the solution was evaporated to dryness, and the residue was purified by preparative TLC to obtain (2R,3R,4R,5S,6S)-3,4,5-tris(benzyloxy)-2-(benzyloxymethyl)-6-(4-chloro-5-(4-ethylbenzyl)-2-((2-fluoromethoxy)methyl)phenyl)tetrahydro-2H-pyran (intermediate BY) (30 mg, 0.07 mmol, yield 49.9%).

Preparation of (2S,3R,4R,5S,6R)-2-(4-chloro-5-(4-ethylbenzyl)-2-((2-fluoroethoxy)methyl)phenyl)-6-(hydroxymethyl)tetrahydro-2H-pyran-3,4,5-triol (Compound BZ)

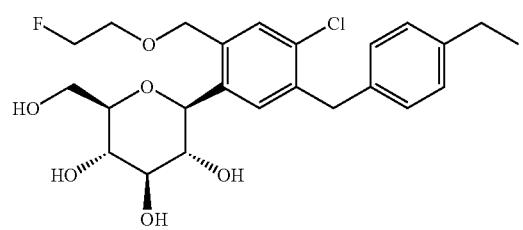

Compound BZ was prepared from intermediate BY by debenzylation using methods analogous to those described in Example 6 above. $^1$H-NMR (DMSO-d$_6$, 300 MHz) δ 7.45 (s, 1H), 7.43 (s, 1H), 7.06 (s, 4H), 4.81 (m, 1H), 4.65 (m, 2H), 4.48 (m, 2H), 4.05 (m, 2H), 3.82 (m, 2H), 3.70 (m, 2H), 3.96 (m, 4H), 2.58 (dd, J=7.8 Hz, 2H), 1.19 (t, J=7.8 Hz, 3H); MS (m/z) (ESI$^+$) 469 [M+1]$^+$, 486 [M+18]$^+$, (ESI)$^-$513 [M+45]$^-$.

Example 47

Preparation of (2R,3R,4R,5S,6S)-3,4,5-tris(benzyloxy)-2-(benzyloxymethyl)-6-(4-chloro-2-((2,2-difluoropropoxy)methyl)-5-(4-ethylbenzyl)phenyl)tetrahydro-2H-pyran (Intermediate CA)

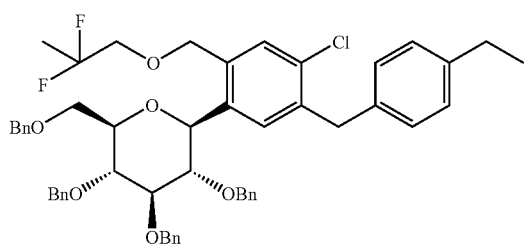

To a solution of 1-(5-chloro-4-(4-ethylbenzyl)-2-((2S,3S,4R,5R,6R)-3,4,5-tris(benzyloxy)-6-(benzyloxymethyl)tetrahydro-2H-pyran-2-yl)benzyloxy)propan-2-one (intermediate T-1) (60 mg, 0.07 mmol) in 6 mL of $CH_2Cl_2$ at −78° C., was added dropwise DAST (1.22 mL, 0.18 mmol). The resulting solution was slowly warmed to room temperature and stirred for 3 h. The reaction was quenched by addition of MeOH (2 mL), the solution was evaporated to dryness, and the residue was purified by preparative TLC to obtain (2R,3R,4R,5S,6S)-3,4,5-tris(benzyloxy)-2-(benzyloxymethyl)-6-(4-chloro-2-((2,2-difluoropropoxy)methyl)-5-(4-ethylbenzyl)phenyl)tetrahydro-2H-pyran (intermediate CA) (42 mg, 0.048 mmol, yield 68.1%).

Preparation of (2S,3R,4R,5S,6R)-2-(4-chloro-2-((2,2-difluoropropoxy)methyl)-5-(4-ethylbenzyl)phenyl)-6-(hydroxymethyl)tetrahydro-2H-pyran-3,4,5-triol (Compound CB)

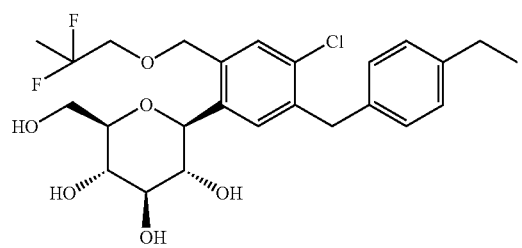

Compound CB was prepared from intermediate CA by debenzylation using methods analogous to those described in Example 6 above. $^1$H-NMR (DMSO-$d_6$, 300 MHz) δ 7.46 (s, 1H), 7.41 (s, 1H), 7.08 (s, 4H), 4.80 (s, 1H), 4.62 (m, 2H), 4.45 (m, 1H), 4.06 (m, 2H), 3.83 (s, 1H), 3.67 (t, J=12.3 Hz, 2H), 3.40 (m, 4H), 2.58 (dd, J=7.8 Hz, 2H), 1.64 (t, J=18.4 Hz, 3H), 1.18 (t, J=7.8 Hz, 3H); MS (m/z) (ESI)$^+$518 [M+18]$^+$, (ESI)$^-$545 [M+45]$^-$.

Example 48

Preparation of (2S,3R,4R,5S,6R)-2-(4-chloro-5-(4-ethoxybenzyl)-2-((prop-2-ynyloxy)methyl)phenyl)-6-(hydroxymethyl)tetrahydro-2H-pyran-3,4,5-triol (Compound CC)

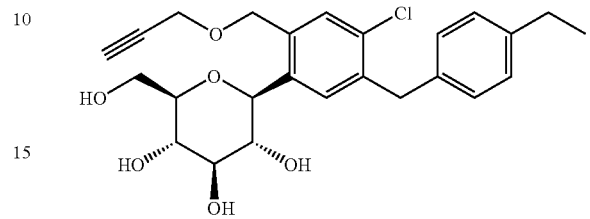

To a stirred solution of (2R,3R,4R,5S,6S)-2-(acetoxymethyl)-6-(4-chloro-5-(4-ethoxybenzyl)-2-((prop-2-ynyloxy)methyl)phenyl)tetrahydro-2H-pyran-3,4,5-triyl triacetate (prepared using methods analogous to those in Example 1 and Example 5 above, 251 mg, 0.39 mmol) in THF:MeOH:$H_2O$ (2:3:1, 6.0 mL) at 15° C., was added LiOH—$H_2O$ (19.7 mg, 0.47 mmol). After stirring for 12 h at room temperature, the reaction was complete, as indicated by HPLC. The reaction mixture was concentrated and the residue was dissolved in 20 mL of ethyl acetate. The organic layer was washed with brine (20 mL), 5% KHSO4 in brine (20 mL), dried over anhydrous sodium sulfate, evaporated, and the residue was purified by preparative TLC (PE:EtOAc:MeOH=8:80:1, $R_f$=0.45) to obtain 156 mg of title compound as a white solid (yield 84%; purity 99.2%, as determined by HPLC). $^1$H-NMR (CD$_3$OD, 400 MHz) δ 7.48 (s, 1H), 7.42 (s, 1H), 7.11 (s, 4H), 4.86 (d, J=12.4 Hz, 1H), 4.60 (d, J=12.4 Hz, 1H), 4.52 (d, J=9.2 Hz, 1H), 4.20 (s, 2H), 4.12 (d, J=14.8 Hz, 1H), 4.06 (d, J=14.8 Hz, 1H), 3.98 (q, J=6.8 Hz, 2H), 3.86 (d, J=12.4 Hz, 1H), 3.70-3.66 (m, 1H), 3.52-3.41 (m, 4H), 2.63 (s, 1H), 1.36 (t, J=6.8 Hz, 3H); LC-MS (m/z) 477 [(M+1)$^+$], 521 [(M+45)$^-$].

Example 49

Preparation of ((2R,3S,4R,5R,6S)-6-(4-chloro-5-(4-ethoxybenzyl)-2-((prop-2-ynyloxy)methyl)phenyl)-3,4,5-trihydroxytetrahydro-2H-pyran-2-yl)methyl acetate (Compound CD)

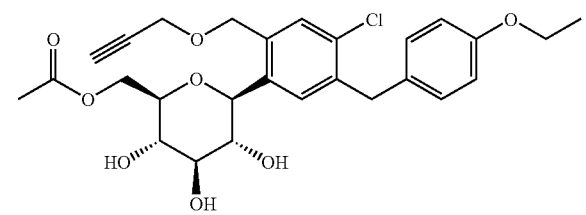

To a stirred solution of (2R,3R,4R,5S,6S)-2-(acetoxymethyl)-6-(4-chloro-5-(4-ethoxybenzyl)-2-((prop-2-ynyloxy)methyl)phenyl)tetrahydro-2H-pyran-3,4,5-triyl triacetate (prepared using methods analogous to those in Example 1 and Example 5 above, 251 mg, 0.39 mmol) in THF:MeOH:$H_2O$ (2:3:1, 6.0 mL) at 15° C., was added LiOH.$H_2O$ (16.4 mg, 0.39 mmol). After stirring for 5 h at room temperature, the reaction was complete, as indicated by HPLC. The reaction mixture was concentrated and the residue was dissolved in 20 mL of ethyl acetate. The organic layer was washed with brine (20 mL), 5% KHSO4 in brine (20 mL), dried over anhydrous sodium sulfate, evaporated, and the residue was purified by preparative TLC (PE:EtOAc:MeOH=8:80:1, $R_f$=0.45) to afford 160 mg of title compound as a white solid (yield 79.2%; purity 99.1%, as determined by HPLC). $^1$H-NMR (CD$_3$OD, 400 MHz) δ 7.48 (s, 1H), 7.40 (s, 1H), 7.12 (s, 4H), 4.85 (d, J=12.0 Hz, 1H), 4.62 (d, J=12.0 Hz, 1H), 4.51 (d, J=9.2 Hz, 1H), 4.23 (s, 2H), 4.10 (d, J=14.8 Hz, 1H), 4.05 (d, J=14.8 Hz, 1H), 3.96 (q, J=6.8 Hz, 2H), 3.88 (d, J=12.4 Hz, 1H), 3.71-3.67 (m, TH), 3.52-3.41 (m, 4H), 2.94 (s, 1H), 2.15 (s, 3H), 1.34 (t, J=6.8 Hz, 3H); LC-MS (m/z) 519 [(M+1)$^+$], 563 [(M+45)$^-$].

Example 50

The SGLT inhibitory effects of the compounds of the present invention were demonstrated by the following procedures.

Preparation of Human SGLT2 Expression Vector

A full-length cDNA clone expressing human SGLT2 (GenScript Corporation) was subcloned into Hind HIII and Not I sites of pEAK15 expression vector. Clones harboring the cDNA inserts were identified by restriction analysis.

Preparation of a Cell Line Stably Expressing Human SGLT2

Plasmid containing human SGLT2 was linearized with Nsi I and purified by agarose gel electrophoresis. Using Lipofectamine 2000 Transfection Reagent (Invitrogen Corporation), DNA was transfected into HEK293.ETN cells and cultured in Dulbecco's Modified Eagle Medium (DMEM) containing 10% fetal bovine serum (FBS) at 37° C. under 5% CO$_2$ for 24 h. Transfectants were selected in the same growth medium supplemented with puromycin (Invitrogen Corporation) for two weeks. Puromycin-resistant cells were recovered and seeded on a fresh 96-well plate (single cell per well) and cultured in the presence of puromycin until cells became confluent. Puromycin-resistant clones were evaluated for SGLT2 activity in the methyl-α-D-[U-$^{14}$C]glucopyranoside uptake assay described below. The clone that exhibited the highest signal-to-background ratio was used for the methyl-α-D-[U-$^{14}$C]glucopyranoside uptake assay.

Preparation of Human SGLT1 Expressing Cells

Full-length human SGLT1 cDNA on pDream2.1 expression vector was obtained from GenScript Corporation and propagated in *Escherichia coli* strain DH5α using Luria-Bertani (LB) medium containing ampicillin. Plasmid DNA was isolated using the QIAGEN Plasmid Midi Kit (QIAGEN Inc.). Human SGLT1 expression plasmid DNA was transfected into COS-7 cells (American Type Culture Collection) using Lipofectamine 2000 Transfection Reagent according to a manufacturer suggested protocol. Transfected cells were stored in DMEM containing 10% dimethyl sulfoxide (DMSO) at −80° C.

Methyl-α-D-[U-$^{14}$C]Glucopyranoside Uptake Assay

Cells expressing SGLT1 or SGLT2 were seeded on 96-well ScintiPlate scintillating plates (PerkinElmer, Inc.) in DMEM containing 10% FBS (1×10$^5$ cells per well in 100 µL medium) incubated at 37° C. under 5% CO$_2$ for 48 h prior to the assay. Cells were washed twice with 150 µL of either sodium buffer (137 mM NaCl, 5.4 mM KCl, 2.8 mM CaCl$_2$, 1.2 mM MgCl$_2$, 10 mM tris(hydroxymethyl)aminomethane/N2-hydroxyethylpiperazine-N'-ethanesulfonic acid [Tris/Hepes], pH 7.2) or sodium-free buffer (137 mM N-methyl-glucamine, 5.4 mM KCl, 2.8 mM CaCl$_2$, 1.2 mM MgCl$_2$, 10 mM Tris/Hepes, pH 7.2). Test compound in 50 µL each of sodium or sodium-free buffer containing 40 µCi/L methyl-α-D-[U-$^{14}$C]glucopyranoside (Amersham Biosciences/GE Healthcare), either with (symbols in parentheses) or without (symbols without parentheses) 25% human serum, was added per well of a 96-well plate and incubated at 37° C. with shaking for either 2 h (SGLT1 assay) or 1.5 h (SGLT2 assay). Cells were washed twice with 150 µL of wash buffer (137 mM N-methylglucamine, 10 mM Tris/Hepes, pH 7.2) and methyl-α-D-[U-$^{14}$C] glucopyranoside uptake was quantitated using a TopCount scintillation counter (PerkinElmer, Inc.). Sodium-dependent glucopyranoside uptake was measured by subtracting the values obtained with sodium-free buffer from those obtained using sodium buffer (average of triplicate determinations).

TABLE 1

| Compound | IC$_{50}$* SGLT2 | SGLT1 |
|---|---|---|
| I | + | +++ |
| K | + | +++ |
| L | + | +++ |
| M | + | +++ |
| N | + | +++ |
| O | + | ++ |
| R | + | +++ |
| S | + | +++ |
| T | + | ++ |
| W | + | +++ |
| AD | + | +++ |
| AG | + | ++ |
| AH | + | ++ |
| AI | + | +++ |
| AK | + | +++ |
| AL | + | +++ |
| AM | + | +++ |
| AN | + | ++ |
| AO | + | +++ |
| AW | + | +++ |
| AX | (+) | (+++) |
| AY | + | +++ |
| AZ | + | +++ |
| BA | (+) | (+++) |
| BB | (+) | (+++) |
| BC | (+) | (+++) |
| BD | + | +++ |
| BF | (+) | (+++) |
| BG | (+) | (+++) |
| BH | (+) | (++) |
| BO | (+) | (+++) |
| BQ | (+) | (+++) |
| BS | (+) | (+++) |
| BZ | + | +++ |
| CB | + | +++ |
| CC | (+) | (+++) |
| CD | (+) | (+++) |

*Key:
+ <1 µM
++ 1 µM to 10 µM
+++ >10 µM
( ) indicates incubation with 25% human serum

What is claimed is:

1. A compound having the formula:

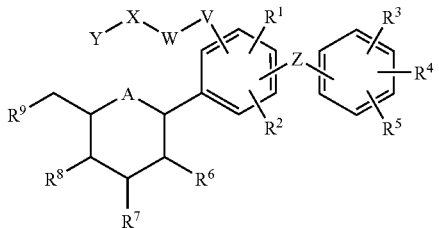

wherein
- A is a member selected from the group consisting of oxygen; sulfur; SO; $SO_2$; methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy; $C_3$-$C_5$ 1,1-cycloalkylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; and $NR^a$;
- V is a member selected from the group consisting of oxygen; sulfur; SO; $SO_2$; and a single bond;
- W is a member selected from the group consisting of $C_1$-$C_6$ alkylene, $C_2$-$C_6$ alkenylene, $C_2$-$C_6$ alkynylene, $C_3$-$C_{10}$ cycloalkylene and $C_5$-$C_{10}$ cycloalkenylene;
  - wherein each alkylene, alkenylene, alkynylene, cycloalkylene and cycloalkenylene group of W is optionally partly or completely fluorinated and is optionally mono- or disubstituted by identical or different substituents selected from chlorine, hydroxy, $C_1$-$C_3$ alkyl, $C_1$-$C_3$ alkoxy, $C_3$-$C_6$ cycloalkyl, $C_3$-$C_6$ cycloalkyloxy, $C_5$-$C_{10}$ cycloalkenyl and $C_5$-$C_{10}$ cycloalkenyloxy, and in cycloalkylene and cycloalkenylene groups of W, one or two methylene groups are optionally replaced independently of one another by O, S, CO, SO, $SO_2$ or $NR^b$, and one or two methyne groups of W are optionally replaced by N;
- X is (i) a member selected from the group consisting of oxygen; sulfur; SO; and $SO_2$; or (ii) $NR^a$;
- when X is (i), Y is a member selected from the group consisting of $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, $C_5$-$C_{10}$ cycloalkenyl, ($C_5$-$C_{10}$ cycloalkenyl) $C_1$-$C_3$ alkyl, ($C_3$-$C_{10}$ cycloalkyl)$C_2$-$C_4$ alkenyl, $C_3$-$C_6$ cycloalkylidenmethyl, ($C_5$-$C_{10}$ cycloalkenyl)$C_2$-$C_4$ alkenyl, ($C_1$-$C_4$ alkyloxy)$C_1$-$C_3$ alkyl, ($C_2$-$C_4$ alkenyloxy) $C_1$-$C_3$ alkyl, ($C_3$-$C_{10}$ cycloalkyloxy)$C_1$-$C_3$ alkyl, ($C_5$-$C_{10}$ cycloalkenyloxy)$C_1$-$C_3$ alkyl, ($C_1$-$C_4$ alkylamino) $C_1$-$C_3$ alkyl, di-($C_1$-$C_3$ alkylamino)$C_1$-$C_3$ alkyl, ($C_1$-$C_6$ alkyl)carbonyl($C_1$-$C_3$)alkyl, ($C_2$-$C_6$ alkenyl)carbonyl ($C_1$-$C_3$)alkyl, ($C_2$-$C_6$ alkynyl)carbonyl($C_1$-$C_3$)alkyl, (arylcarbonyl)$C_1$-$C_3$ alkyl, (heteroarylcarbonyl)$C_1$-$C_3$ alkyl, ($C_1$-$C_6$ alkylsulfonyl)$C_1$-$C_3$ alkyl, ($C_2$-$C_6$ alkenylsulfonyl)$C_1$-$C_3$ alkyl, ($C_2$-$C_6$ alkynylsulfonyl)$C_1$-$C_3$ alkyl, (arylsulfonyl)$C_1$-$C_3$ alkyl, (heteroarylsulfonyl) $C_1$-$C_3$ alkyl, ($C_1$-$C_6$ alkyl)aminocarbonyl($C_1$-$C_3$)alkyl, ($C_2$-$C_6$ alkenyl)aminocarbonyl($C_1$-$C_3$)alkyl, ($C_2$-$C_6$ alkynyl)aminocarbonyl($C_1$-$C_3$)alkyl, (arylaminocarbonyl)$C_1$-$C_3$ alkyl, (heteroarylaminocarbonyl)$C_1$-$C_3$ alkyl, ($C_1$-$C_6$ alkyl)carbonyl, ($C_2$-$C_6$ alkenyl)carbonyl, ($C_2$-$C_6$ alkynyl)carbonyl, arylcarbonyl and heteroarylcarbonyl;

wherein alkyl, alkenyl, alkynyl, cycloalkyl and cycloalkenyl groups or portions of Y are optionally partly or completely fluorinated and optionally are mono- or disubstituted by identical or different substituents selected from the group consisting of chlorine, hydroxy, $C_1$-$C_3$ alkyl, $C_1$-$C_3$ alkoxy, $C_3$-$C_6$ cycloalkyl, $C_3$-$C_6$ cycloalkyloxy, $C_5$-$C_{10}$ cycloalkenyl, $C_5$-$C_{10}$ cycloalkenyloxy, and $NR^bR^c$, and in cycloalkyl and cycloalkenyl groups or portions of Y, one or two methylene groups are optionally replaced independently of one another by O, S, CO, SO, $SO_2$ or $NR^b$, and one or two methyne groups are optionally replaced by N, wherein the heterocycle formed by said optional replacement is other than heteroaryl, and wherein when V is a member selected from the group consisting of oxygen, sulfur and a single bond and W is a member selected from the group consisting of $C_1$-$C_6$ alkylene, $C_2$-$C_6$ alkenylene and $C_2$-$C_6$ alkynylene, then Y is other than $C_1$-$C_6$ alkyl;

- when X is (ii), Y is a member selected from the group consisting of $C_1$-$C_6$ alkylsulfonyl, $C_2$-$C_6$ alkenylsulfonyl, $C_2$-$C_6$ alkynylsulfonyl, arylsulfonyl, heteroarylsulfonyl, $C_1$-$C_6$ alkylsulfinyl, arylsulfinyl, heteroarylsulfinyl, ($C_1$-$C_6$ alkyl)carbonyl, ($C_2$-$C_6$ alkenyl)carbonyl, ($C_2$-$C_6$ alkynyl)carbonyl, arylcarbonyl, heteroarylcarbonyl, ($C_1$-$C_6$ alkyl)aminocarbonyl, ($C_2$-$C_6$ alkenyl)aminocarbonyl, ($C_2$-$C_6$ alkynyl)aminocarbonyl, arylaminocarbonyl, heteroarylaminocarbonyl, ($C_1$-$C_6$ alkylsulfonyl)$C_1$-$C_3$ alkyl, ($C_2$-$C_6$ alkenylsulfonyl)$C_1$-$C_3$ alkyl, ($C_2$-$C_6$ alkenylsulfonyl)$C_1$-$C_3$ alkyl, (arylsulfonyl)$C_1$-$C_3$ alkyl, (heteroarylsulfonyl)$C_1$-$C_3$ alkyl, ($C_1$-$C_6$ alkylsulfinyl)$C_1$-$C_3$ alkyl, (arylsulfinyl)$C_1$-$C_3$ alkyl, (heteroarylsulfinyl)$C_1$-$C_3$ alkyl, ($C_1$-$C_6$ alkyl)aminocarbonyl($C_1$-$C_3$)alkyl, ($C_2$-$C_6$ alkenyl)aminocarbonyl($C_1$-$C_3$)alkyl, ($C_2$-$C_6$ alkynyl)aminocarbonyl($C_1$-$C_3$)alkyl, (arylaminocarbonyl)$C_1$-$C_3$ alkyl and (heteroarylaminocarbonyl)$C_1$-$C_3$ alkyl;

wherein alkyl, alkenyl and alkynyl portions of Y are optionally partly or completely fluorinated, and when $R^a$ is H or ($C_1$-$C_4$ alkyl)carbonyl, then Y is other than ($C_1$-$C_6$ alkyl)carbonyl or arylcarbonyl;

- Z is a member selected from the group consisting of oxygen; sulfur; SO; $SO_2$; 1,1-cyclopropylene; carbonyl; and methylene optionally substituted with one to two substituents independently selected from the group consisting of halo, hydroxy, $C_1$-$C_6$ alkyl, $C_1$-$C_6$ alkoxy, $C_3$-$C_6$ cycloalkyl and $C_3$-$C_6$ cycloalkyloxy;

- $R^1$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$) alkyl, ($C_2$-$C_4$ alkenyl)$C_1$-$C_3$ alkyloxy, ($C_2$-$C_4$ alkynyl) $C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy) $C_1$-$C_3$ alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, aryl, heteroaryl, ($C_1$-$C_4$ alkyl)carbonyl, arylcarbonyl, heteroarylcarbonyl, hydroxycarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano and nitro;

wherein alkyl, alkenyl, alkynyl, cycloalkyl and cycloalkenyl groups or portions of $R^1$ are optionally partly or completely fluorinated and are optionally mono- or disubstituted by identical or different substituents selected from the group consisting of chlorine, hydroxy, $C_1$-$C_3$ alkoxy and $C_1$-$C_3$ alkyl, and in cycloalkyl and cycloalkenyl groups or portions of $R^1$, one or two methylene groups are optionally replaced independently of one another by O, S, CO, SO or $SO_2$, and in N-heterocycloalkyl groups or portions of $R^1$, a methylene group is optionally replaced by CO or $SO_2$;

$R^2$ is a member selected from the group consisting of hydrogen, halo, hydroxy, $C_1$-$C_4$ alkyl, $C_2$-$C_6$ alkenyl, $C_2$-$C_6$ alkynyl, $C_3$-$C_{10}$ cycloalkyl, $C_5$-$C_{10}$ cycloalkenyl, $C_1$-$C_4$ alkyloxy, $C_3$-$C_{10}$ cycloalkyloxy, cyano and nitro; wherein alkyl and cycloalkyl groups or portions of $R^2$ are optionally mono- or polysubstituted by fluorine, or in the event that $R^1$ and $R^2$ are bound to adjacent C atoms of the phenyl ring, $R^1$ and $R^2$ are optionally joined together to form a $C_3$-$C_5$ alkylene, $C_3$-$C_5$ alkenylene or butadienylene bridge, which is optionally partly or completely fluorinated and optionally mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methyne groups optionally may be replaced by N;

$R^3$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$)cycloalkyl-($C_1$-$C_3$)alkyl, $C_5$-$C_{10}$ cycloalkenyl, ($C_5$-$C_{10}$)cycloalkenyl-($C_1$-$C_3$)alkyl, ($C_1$-$C_4$ alkyloxy)$C_1$-$C_3$ alkyl, ($C_3$-$C_{10}$ cycloalkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_3$-$C_{10}$ cycloalkyl)$C_2$-$C_4$ alkenyl, $C_3$-$C_6$ cycloalkylidenmethyl, aryl, heteroaryl, ($C_1$-$C_4$ alkyl)carbonyl, arylcarbonyl, heteroarylcarbonyl, aminocarbonyl, ($C_1$-$C_4$ alkyl)aminocarbonyl, di-($C_1$-$C_3$ alkyl)aminocarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, hydroxycarbonyl, ($C_1$-$C_4$ alkyloxy)carbonyl, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, heteroarylcarbonylamino, $C_1$-$C_4$ alkylsulfonylamino, arylsulfonylamino, $C_1$-$C_6$ alkyloxy, $C_3$-$C_{10}$ cycloalkyloxy, $C_5$-$C_7$ cycloalkenyloxy, aryloxy, heteroaryloxy, ($C_2$-$C_4$ alkenyl)$C_1$-$C_3$ alkyloxy, ($C_2$-$C_4$ alkynyl)$C_1$-$C_3$ alkyloxy, (aryl)$C_1$-$C_3$ alkyloxy, (heteroaryl)$C_1$-$C_3$ alkyloxy, $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, amino, hydroxy, cyano and nitro;

wherein alkyl, alkenyl, alkynyl, cycloalkyl and cycloalkenyl groups or portions of $R^3$ are optionally partly or completely fluorinated and are optionally mono- or disubstituted by identical or different substituents selected from chlorine, hydroxy, $C_1$-$C_3$ alkoxy and $C_1$-$C_3$ alkyl, and in cycloalkyl and cycloalkenyl groups or portions of $R^3$, one or two methylene groups are optionally replaced independently of one another by O, S, CO, SO or $SO_2$, and in N-heterocycloalkyl groups or portions of $R^3$, a methylene group is optionally replaced by CO or $SO_2$;

$R^4$ is a member selected from the group consisting of hydrogen, halo, cyano, nitro, hydroxy, $C_1$-$C_3$ alkyl, $C_3$-$C_{10}$ cycloalkyl, $C_1$-$C_3$ alkyloxy or $C_3$-$C_{10}$ cycloalkyloxy, wherein alkyl and cycloalkyl groups or portions of $R^4$ are optionally mono- or polysubstituted by fluorine, and when $R^3$ and $R^4$ are bound to adjacent C atoms of the phenyl ring, $R^3$ and $R^4$ are optionally joined to form a $C_3$-$C_5$ alkylene, $C_3$-$C_5$ alkenylene or butadienylene bridge, which is optionally partly or completely fluorinated and is optionally mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methyne groups are optionally replaced by N;

$R^5$ is a member selected from the group consisting of hydrogen, halo, cyano, nitro, hydroxy, $C_1$-$C_3$ alkyl, $C_3$-$C_{10}$ cycloalkyl and $C_1$-$C_3$ alkyloxy, wherein alkyl and cycloalkyl groups or portions of $R^5$ are optionally mono- or polysubstituted by fluorine;

$R^6$, $R^7$, $R^8$ and $R^9$ are each independently selected from the group consisting of hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, ($C_3$-$C_{10}$ cycloalkyl)carbonyloxy, hydrogen, halo, $C_1$-$C_6$ alkyl, $C_2$-$C_6$ alkenyl, $C_2$-$C_6$ alkynyl, ($C_3$-$C_{10}$)cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, $C_3$-$C_7$ cycloalkyloxy, $C_5$-$C_7$ cycloalkenyloxy, aryloxy, heteroaryloxy, ($C_3$-$C_7$)cycloalkyl-($C_1$-$C_3$)alkyloxy, ($C_5$-$C_7$)cycloalkenyl-($C_1$-$C_3$)alkyloxy, aryl-($C_1$-$C_3$)alkyloxy, heteroaryl-($C_1$-$C_3$)alkyloxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkyloxy)carbonyl, aminocarbonyl-($C_1$-$C_3$) alkyl, ($C_1$-$C_4$ alkyl)aminocarbonyl-($C_1$-$C_3$)alkyl, di-($C_1$-$C_3$ alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$) alkyl, ($C_3$-$C_7$)cycloalkyloxy-($C_1$-$C_3$)alkyl, ($C_5$-$C_7$)cycloalkenyloxy-($C_1$-$C_3$)alkyl, aryloxy-($C_1$-$C_3$)alkyl, heteroaryloxy-($C_1$-$C_3$)alkyl, $C_1$-$C_4$ alkylsulfonyloxy, arylsulfonyloxy, aryl-($C_1$-$C_3$)alkyl-sulfonyloxy, trimethylsilyloxy, t-butyldimethylsilyloxy, and cyano;

wherein alkyl, alkenyl, alkynyl, cycloalkyl and cycloalkenyl groups or portions of $R^6$, $R^7$, $R^8$ and $R^9$ are optionally partly or completely fluorinated and are optionally mono- or disubstituted by identical or different substituents selected from the group consisting of chlorine, hydroxy, $C_1$-$C_3$ alkoxy and $C_1$-$C_3$ alkyl, and in cycloalkyl and cycloalkenyl groups or portions of $R^6$, $R^7$, $R^8$ and $R^9$, one or two methylene groups are optionally replaced independently of one another by $NR^b$, O, S, CO, SO or $SO_2$;

each $R^a$ is a member independently selected from the group consisting of H, $C_1$-$C_6$ alkyl, $C_3$-$C_6$ cycloalkyl and ($C_1$-$C_4$ alkyl)carbonyl, wherein alkyl and cycloalkyl groups or portions of $R^a$ are optionally partly or completely fluorinated;

each $R^b$ is a member independently selected from the group consisting of H, $C_1$-$C_4$ alkyl and ($C_1$-$C_4$ alkyl)carbonyl, wherein alkyl groups or portions of $R^b$ are optionally partly or completely fluorinated;

each $R^c$ is a member independently selected from the group consisting of H, $C_1$-$C_4$ alkyl, $C_3$-$C_6$ cycloalkyl, $CHR^dR^e$, $SO_2R^d$, $C(O)OR^d$ and $C(O)NR^dR^e$, wherein alkyl and cycloalkyl groups of $R^c$ are optionally partly or completely fluorinated; and $R^d$ and $R^e$ each independently represent H or $C_1$-$C_6$ alkyl, wherein alkyl groups of $R^d$ and $R^e$ are optionally partly or completely fluorinated; and pharmaceutically acceptable salts thereof.

2. A compound of claim 1, wherein A is oxygen or sulfur.

3. A compound of claim 1, wherein A is oxygen.

4. A compound of claim 1, wherein V is selected from the group consisting of oxygen, sulfur and a single bond.

5. A compound of claim 1, wherein V is oxygen or a single bond.

6. A compound of claim 1, wherein W is selected from the group consisting of $C_1$-$C_6$ alkylene and $C_3$-$C_{10}$ cycloalkylene; wherein each alkylene and cycloalkylene group of W is optionally partly or completely fluorinated and is optionally mono- or disubstituted by identical or different substituents selected from chlorine, hydroxy, $C_1$-$C_3$ alkyl and $C_1$-$C_3$ alkoxy, and in cycloalkylene groups of W, one or two methylene groups are optionally replaced independently of one another by O, S, CO, SO, $SO_2$ or $NR^b$.

7. A compound of claim 1, wherein W is $C_1$-$C_6$ alkylene.

8. A compound of claim 1, wherein X is oxygen or sulfur.

9. A compound of claim 1, wherein Y is selected from the group consisting of $C_1$-$C_6$ alkyl, $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, $C_5$-$C_{10}$ cycloalkenyl, ($C_1$-$C_4$ alkyloxy)$C_1$-$C_3$ alkyl, ($C_2$-$C_4$ alkenyloxy)$C_1$-$C_3$ alkyl and ($C_3$-$C_{10}$ cycloalkyloxy)$C_1$-$C_3$ alkyl, wherein alkyl, alkenyl, alkynyl, cycloalkyl and cycloalkenyl groups or portions of Y are optionally partly or completely fluorinated and optionally are mono- or disubstituted by identical or different substituents selected from the group consisting of chlorine, hydroxy, $C_1$-$C_3$ alkyl and $C_1$-$C_3$ alkoxy, and in cycloalkyl and cycloalkenyl groups or portions of Y, one or two methylene groups are optionally replaced independently of one another by O, S, CO, SO, $SO_2$ or $NR^b$, and one or two methyne groups are optionally replaced by N, wherein the heterocycle formed by said optional replacement is other than heteroaryl.

10. A compound of claim 1, wherein Z is selected from the group consisting of oxygen, sulfur and methylene, optionally substituted with one or two substituents selected from the group consisting of halo, hydroxy, $C_1$-$C_6$ alkyl, $C_1$-$C_6$ alkoxy, $C_3$-$C_6$ cycloalkyl and $C_3$-$C_6$ cycloalkyloxy.

11. A compound of claim 1, wherein Z is methylene.

12. A compound of claim 1, wherein $R^1$ is a member selected from the group consisting of hydrogen, halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino) $C_1$-$C_3$ alkyl, $C_1$-$C_6$ alkyloxy, $C_3$-$C_{10}$ cycloalkyloxy, hydroxy, cyano and nitro, wherein alkyl and cycloalkyl groups or portions of $R^1$ are optionally partly or completely fluorinated.

13. A compound of claim 1, wherein $R^1$ is a member selected from the group consisting of hydrogen, halo and $C_1$-$C_6$ alkyl.

14. A compound of claim 1, wherein $R^2$ is a member selected from the group consisting of hydrogen, hydroxy, halo, $C_1$-$C_4$ alkyl and $C_1$-$C_4$ alkyloxy.

15. A compound of claim 1, wherein $R^2$ is hydrogen or halo.

16. A compound of claim 1, wherein $R^3$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano and nitro, wherein alkyl and cycloalkyl groups or portions of $R^3$ are optionally partly or completely fluorinated, and in cycloalkyl groups of $R^3$ one or two methylene groups are optionally replaced independently of one another by O, S, CO, SO or $SO_2$.

17. A compound of claim 1, wherein $R^3$ is a member selected from the group consisting of hydrogen, halo, hydroxy, $C_1$-$C_6$ alkyl, $C_1$-$C_6$ alkyloxy, $C_2$-$C_6$ alkenyl, $C_2$-$C_6$ alkynyl, $C_3$-$C_{10}$ cycloalkyl and $C_3$-$C_{10}$ cycloalkyloxy, wherein alkyl and cycloalkyl groups or portions of $R^3$ are optionally partly or completely fluorinated, and in cycloalkyl groups of $R^3$ a methylene group is optionally replaced by O, S, CO, SO or $SO_2$.

18. A compound of claim 1, wherein $R^4$ and $R^5$ are each independently selected from the group consisting of hydrogen, halo, cyano, hydroxy, nitro, $C_1$-$C_3$ alkyl, $C_1$-$C_3$ alkyloxy and $C_3$-$C_{10}$ cycloalkyl.

19. A compound of claim 1, wherein $R^4$ and $R^5$ are each independently selected from the group consisting of hydrogen, halo and hydroxy.

20. A compound of claim 1, wherein $R^6$, $R^7$, $R^8$ and $R^9$ are each independently selected from the group consisting of hydroxy, halo, ($C_1$-$C_6$ alkyl)carbonyloxy, ($C_1$-$C_6$ alkyl)oxycarbonyloxy, arylcarbonyloxy, aryl-($C_1$-$C_3$ alkyl)carbonyloxy, ($C_3$-$C_{10}$ cycloalkyl)carbonyloxy, $C_1$-$C_6$ alkyl, $C_1$-$C_6$ alkyloxy, ($C_3$-$C_7$)cycloalkyloxy, aryloxy and ($C_3$-$C_7$)cycloalkyl-($C_1$-$C_3$)alkyloxy, wherein alkyl and cycloalkyl groups or portions of each of $R^6$, $R^7$, $R^8$ and $R^9$ are optionally partly or completely fluorinated.

21. A compound of claim 1, wherein $R^6$, $R^7$, $R^8$ and $R^9$ are each hydroxyl.

22. A compound of claim 1, having the formula:

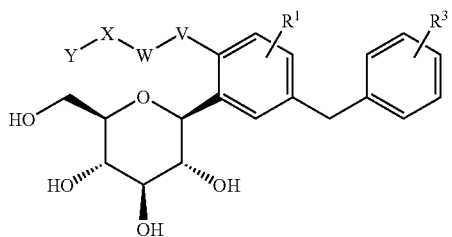

wherein

V is oxygen or a single bond; W is $C_1$-$C_6$ alkylene; X is oxygen or sulfur; Y is a member selected from the group consisting of $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, $C_5$-$C_{10}$ cycloalkenyl, ($C_1$-$C_4$ alkyloxy)$C_1$-$C_3$ alkyl, ($C_2$-$C_4$ alkenyloxy)$C_1$-$C_3$ alkyl and ($C_3$-$C_{10}$ cycloalkyloxy) $C_1$-$C_3$ alkyl; wherein alkyl, alkenyl, alkynyl, cycloalkyl and cycloalkenyl groups or portions of Y are optionally partly or completely fluorinated and are optionally mono- or disubstituted by identical or different substituents selected from chlorine, hydroxy, $C_1$-$C_3$ alkyl and $C_1$-$C_3$ alkoxy, and in cycloalkyl and cycloalkenyl groups or portions of Y, one or two methylene groups are optionally replaced independently of one another by O, S, CO, SO, $SO_2$ or $NR^b$, and one or two methyne groups are optionally replaced by N, wherein the heterocycle formed by said optional replacement is other than heteroaryl;

$R^1$ is selected from the group consisting of hydrogen, halo, $C_1$-$C_6$ alkyl and $C_3$-$C_{10}$ cycloalkyl; and $R^3$ is selected from the group consisting of hydrogen, halo, hydroxy, $C_1$-$C_6$ alkyl, $C_1$-$C_6$ alkyloxy, $C_2$-$C_6$ alkenyl, $C_2$-$C_6$ alkynyl, $C_3$-$C_{10}$ cycloalkyl and $C_3$-$C_{10}$ cycloalkyloxy, wherein alkyl and cycloalkyl groups or portions of $R^3$ are optionally partly or completely fluorinated, and in cycloalkyl groups of $R^3$ a methylene group is optionally replaced by O, S, CO, SO or $SO_2$.

23. A compound of claim 1, having the formula:

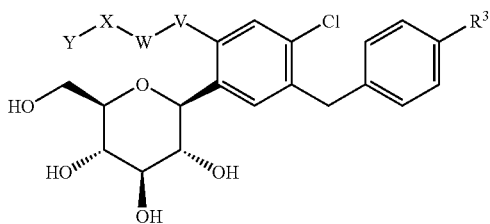

wherein

V is oxygen or a single bond; W is $C_1$-$C_6$ alkylene; X is oxygen or sulfur; Y is a member selected from the group consisting of $C_1$-$C_6$ haloalkyl, $C_1$-$C_6$ hydroxyalkyl, $C_2$-$C_6$ alkenyl, $C_2$-$C_6$ alkynyl, $C_3$-$C_{10}$ cycloalkyl, ($C_1$-$C_4$ alkyloxy)$C_1$-$C_3$ alkyl, ($C_2$-$C_4$ alkenyloxy)$C_1$-$C_3$ alkyl and ($C_3$-$C_{10}$ cycloalkyloxy)$C_1$-$C_3$ alkyl; wherein alkyl, alkenyl, alkynyl and cycloalkyl groups or portions of Y are optionally partly or completely fluorinated and are optionally mono- or disubstituted by identical or different substituents selected from chlorine, hydroxy, $C_1$-$C_3$ alkyl and $C_1$-$C_3$ alkoxy, and in cycloalkyl groups or portions of Y, one or two methylene groups are optionally replaced independently of one another by O, S, CO or $NR^b$;

$R^3$ is selected from the group consisting of ethyl, ethenyl, ethynyl and ethoxy.

24. A compound according to claim 1, which is isotopically labeled.

25. A pharmaceutical composition comprising a pharmaceutically acceptable excipient and a compound according to claim 1.

26. A pharmaceutical combination comprising a compound of claim 1, and at least one therapeutic agent selected from the group consisting of an antidiabetic agent, a lipid-lowering/lipid-modulating agent, an agent for treating diabetic complications, an anti-obesity agent, an antihypertensive agent, an antihyperuricemic agent, and an agent for treating chronic heart failure and atherosclerosis.

27. The pharmaceutical combination of claim 26, wherein the therapeutic agent is at least one antidiabetic agent.

28. The pharmaceutical combination of claim 27, wherein the antidiabetic agent is selected from the group consisting of insulin, a sulfonylurea, an insulin secretion enhancer, a biguanide, a sulfonylurea/biguanide combination, a meglitinide, a thiazolidinedione, a thiazolidinedione/biguanide combination, an oxadiazolidinedione, a PPAR-gamma agonist, a PPAR-alpha/gamma dual agonist, a PPAR-alpha/gamma/delta pan agonist, a retinoid X receptor agonist, an alpha-glucosidase inhibitor, a stimulant of insulin receptor tyrosine kinase, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose 1,6-bisphosphatase inhibitor, a pyruvate dehydrogenase inhibitor, an imidazoline derivative, a hepatic gluconeogenesis inhibitor, D-chiroinositol, a glycogen synthase kinase-3 inhibitor, an incretin mimetic, a glucagon receptor antagonist, GLP-1, a GLP-1 analog, a GLP-1 receptor agonist, amylin, an amylin analog or agonist, an aP2 inhibitor, a beta-3 adrenergic receptor agonist and an insulin sensitivity enhancer.

29. The pharmaceutical combination of claim 28, wherein the antidiabetic agent is selected from the group consisting of insulin, metformin, glyburide, glimepiride, glipyride, glipizide, chlorpropamide, gliclazide, acarbose, miglitol, pioglitazone, rosiglitazone, isaglitazone, netoglitazone, rivoglitazone, repaglinide, nateglinide, exenatide, muraglitazar, naveglitazar, tesaglitazar, peliglitazar, farglitazar, metaglidasen, sitagliptin, vildagliptin, denagliptin, saxagliptin, solabegron and pramlintide.

30. The pharmaceutical combination of claim 26, wherein the therapeutic agent is at least one anti-obesity agent selected from the group consisting of a serotonin-norepinephrine reuptake inhibitor, a norepinephrine-dopamine reuptake inhibitor, a selective serotonin reuptake inhibitor, a selective norepinephrine reuptake inhibitor, a norepinephrine releasing stimulant, an anorexiant, a dopamine agonist, an $H_3$-histamine antagonist, a 5-HT2c receptor agonist, a beta-3 adrenergic receptor agonist, a cholecystokinin agonist, a lipase inhibitor, an antidepressant/acetylcholinesterase inhibitor combination, an anti-epileptic agent, leptin, a leptin analog or leptin receptor agonist, an NPY receptor antagonist or modulator, ciliary neurotrophic factor, a thyroid hormone receptor-beta agonist, a cannabinoid CB1 receptor antagonist, a melanin-concentrating hormone receptor antagonist, a melanocortin-4 receptor agonist and a selective muscarinic receptor $M_1$ antagonist.

31. The pharmaceutical combination of claim 30, wherein the anti-obesity agent is at least one agent selected from the group consisting of rimonabant, orlistat, sibutramine, topiramate, zonisamide, dextroamphetamine, phentermine, phenylpropanolamine, diethylpropion, mazindol, doprexin and Axokine.

32. The pharmaceutical combination of claim 26, wherein the therapeutic agent is at least one lipid-lowering/lipid-modulating agent selected from the group consisting of a hydroxymethylglutaryl coenzyme A reductase inhibitor, a fibric acid derivative, a PPAR-alpha agonist, a PPAR-delta agonist, an acyl-coenzyme A:cholesterol acyltransferase inhibitor, probucol, a thyroid hormone receptor agonist, a cholesterol absorption inhibitor, a lipase inhibitor, a lipoprotein-associated phospholipase A2 inhibitor, a microsomal triglyceride transfer protein inhibitor, a low density lipoprotein receptor activator, a lipoxygenase inhibitor, a carnitine palmitoyl-transferase inhibitor, a squalene synthase inhibitor, a nicotinic acid derivative, a bile acid sequestrant, a sodium/bile acid cotransporter inhibitor, and a cholesterol ester transfer protein inhibitor.

33. The pharmaceutical combination of claim 32, wherein the lipid-lowering/lipid-modulating agent is at least one agent selected from the group consisting of pravastatin, lovastatin, simvastatin, atorvastatin, cerivastatin, fluvastatin, nisvastatin, visastatin, atavastatin, rosuvastatin, colestipol, cholestyramine, colestilan, colesevelam, fenofibrate, gemfibrozil, clofibrate, avasimibe, eflucimibe, eldacimibe, lecimibide, liothyronine, levothyroxine, rilapladib, darapladib, etomoxir, acipimox and torcetrapib.

34. A method for treating type 1 or type 2 diabetes mellitus, hyperglycemia, diabetic complications, insulin resistance, metabolic syndrome, hyperinsulinemia, hypertension, hyperuricemia, obesity, edema, dyslipidemia, chronic heart failure or atherosclerosis, which comprises administering an effective amount of a compound of any of claim 1 to a subject in need thereof.

35. The method of claim 34, further comprising administering, concurrently or sequentially, a therapeutically effective amount of at least one additional therapeutic agent selected from the group consisting of an antidiabetic agent, a lipid-lowering/lipid-modulating agent, an agent for treating diabetic complications, an anti-obesity agent, an antihypertensive agent, an antihyperuricemic agent, and an agent for treating chronic heart failure or atherosclerosis.

36. A method for treating type 1 or type 2 diabetes comprising administering a therapeutically effective amount of a compound of claim 1 alone or in combination with at least one other therapeutic agent selected from the group consisting of an antidiabetic agent, a lipid-lowering/lipid-modulating agent, an agent for treating diabetic complications, an anti-obesity agent, an antihypertensive agent, an antihyperuricemic agent, and an agent for treating chronic heart failure or atherosclerosis.

37. A compound of claim 1, selected from the group consisting of (2S, 3R,4R,5S,6R)-2-(2-(allyloxymethyl)-4-chloro-5-(4-ethylbenzyl)phenyl)-6-(hydroxymethyl)tetrahydro-2H-pyran-3,4,5-triol; 1-(5-chloro-4-(4-ethylbenzyl)-2-((2S,3R,4R,5S,6R)-3,4,5-trihydroxy-6-(hydroxymethyl) tetrahydro-2H-pyran-2-yl)benzyloxy)propan-2-one; (2S,3R, 4R,5S,6R)-2-(4-chloro-2-((2,3-dihydroxypropoxy)methyl)-5-(4-ethylbenzyl)phenyl)-6-(hydroxymethyl)tetrahydro-2H-pyran-3,4,5-triol; (2S,3R,4R,5S,6R)-2-(4-chloro-5-(4-ethylbenzyl)-2-((2-hydroxypropoxy)methyl)phenyl)-6-(hydroxymethyl)tetrahydro-2H-pyran-3,4,5-triol; (2S,3R, 4R,5S,6R)-2-(4-chloro-5-(4-ethylbenzyl)-2-((prop-2-ynyloxy)methyl)phenyl)-6-(hydroxymethyl)tetrahydro-2H-pyran-3,4,5-triol; (2S,3R,4R,5S,6R)-2-(4-chloro-5-(4-ethylbenzyl)-2-((2-hydroxyethoxy)methyl)phenyl)-6-(hydroxymethyl)tetrahydro-2H-pyran-3,4,5-triol; (2S,3R, 4R,5S,6R)-2-(4-chloro-2-((2,2-difluoroethoxy)methyl)-5-(4-ethylbenzyl)phenyl)-6-(hydroxymethyl)tetrahydro-2H-pyran-3,4,5-triol; (2S,3R,4R,5S,6R)-2-(4-chloro-5-(4-ethylbenzyl)-2-((2-methoxyethoxy)methyl)phenyl)-6-(hydroxymethyl)tetrahydro-2H-pyran-3,4,5-triol; (2S,3R, 4R,5S,6R)-2-(4-chloro-5-(4-ethylbenzyl)-2-((2-fluoropropoxy)methyl)phenyl)-6-(hydroxymethyl) tetrahydro-2H-pyran-3,4,5-triol; (2S,3R,4R,5S,6R)-2-(4-chloro-5-(4-ethylbenzyl)-2-((2-hydroxy-3-methoxypropoxy)methyl)phenyl)-6-(hydroxymethyl)tetrahydro-2H-pyran-3,4,5-triol; (2S,3R,4R,5S,6R)-2-(2-(2-(allyloxy)ethyl)-4-chloro-5-(4-ethylbenzyl)phenyl)-6-(hydroxymethyl)tetrahydro-2H-pyran-3,4,5-triol; (2S,3R,4R, 5S,6R)-2-(4-chloro-5-(4-ethylbenzyl)-2-(2-(2-hydroxyethoxy)ethyl)phenyl)-6-(hydroxymethyl) tetrahydro-2H-pyran-3,4,5-triol; (2S,3R,4R,5S,6R)-2-(4-chloro-5-(4-ethylbenzyl)-2-(2-(2-fluoroethoxy)ethyl) phenyl)-6-(hydroxymethyl)tetrahydro-2H-pyran-3,4,5-triol; (2S,3R,4R,5S,6R)-2-(4-chloro-2-(2-(2,2-difluoroethoxy) ethyl)-5-(4-ethylbenzyl)phenyl)-6-(hydroxymethyl)tetrahydro-2H-pyran-3,4,5-triol; (2S,3R,4R,5S,6R)-2-(4-chloro-5-(4-ethylbenzyl)-2-(2-(2,2,2-trifluoroethoxy)ethyl)phenyl)-6-(hydroxymethyl)tetrahydro-2H-pyran-3,4,5-triol; (2S,3R, 4R,5S,6R)-2-(4-chloro-5-(4-ethylbenzyl)-2-((3-hydroxypropoxy)methyl)phenyl)-6-(hydroxymethyl) tetrahydro-2H-pyran-3,4,5-triol; (2S,3R,4R,5S,6R)-2-(4-chloro-5-(4-ethylbenzyl)-2-(2-(prop-2-ynyloxy)ethyl) phenyl)-6-(hydroxymethyl)tetrahydro-2H-pyran-3,4,5-triol; (2S,3R,4R,5S,6R)-2-(2-(2-(but-2-ynyloxy)ethyl)-4-chloro-5-(4-ethylbenzyl)phenyl)-6-(hydroxymethyl)tetrahydro-2H-pyran-3,4,5-triol; (2S,3R,4R,5S,6R)-2-(4-chloro-5-(4-ethoxybenzyl)-2-(2-(prop-2-ynyloxy)ethyl)phenyl)-6-(hydroxymethyl)tetrahydro-2H-pyran-3,4,5-triol; (2S,3R, 4R,5S,6R)-2-(2-(2-(allyloxy)ethoxy)-4-chloro-5-(4-ethylbenzyl)phenyl)-6-(hydroxymethyl)tetrahydro-2H-pyran-3,4,5-triol; (2S,3R,4R,5S,6R)-2-(2-((but-2-ynyloxy) methyl)-4-chloro-5-(4-ethylbenzyl)phenyl)-6-(hydroxymethyl)tetrahydro-2H-pyran-3,4,5-triol; (2S,3R, 4R,5S,6R)-2-(2-((but-2-ynyloxy)methyl)-4-chloro-5-(4-ethoxybenzyl)phenyl)-6-(hydroxymethyl)tetrahydro-2H-pyran-3,4,5-triol; (2S,3R,4R,5S,6R)-2-(2-(allyloxymethyl)-4-chloro-5-(4-ethoxybenzyl)phenyl)-6-(hydroxymethyl) tetrahydro-2H-pyran-3,4,5-triol; (2S,3R,4R,5S,6R)-2-(2-((but-2-ynyloxy)methyl)-4-chloro-5-(4-methoxybenzyl) phenyl)-6-(hydroxymethyl)tetrahydro-2H-pyran-3,4,5-triol; (2S,3R,4R,5S,6R)-2-(5-(4-(allyloxy)benzyl)-2-(allyloxymethyl)-4-chlorophenyl)-6-(hydroxymethyl)tetrahydro-2H-pyran-3,4,5-triol; (2S,3R,4R,5S,6R)-2-(2-((but-2-ynyloxy) methyl)-4-chloro-5-(4-hydroxybenzyl)phenyl)-6-(hydroxymethyl)tetrahydro-2H-pyran-3,4,5-triol; ((2R,3S, 4R,5R,6S)-6-(4-chloro-5-(4-ethylbenzyl)-2-((prop-2-ynyloxy)methyl)phenyl)-3,4,5-trihydroxytetrahydro-2H-pyran-2-yl)methyl acetate; (2S,3R,4R,5S,6R)-2-(4-chloro-5-(4-ethylbenzyl)-2-(2-(prop-2-ynyloxy)ethoxy)phenyl)-6-(hydroxymethyl)tetrahydro-2H-pyran-3,4,5-triol; (2S,3R, 4R,5S,6R)-2-(2-(2-(but-2-ynyloxy)ethoxy)-4-chloro-5-(4-ethylbenzyl)phenyl)-6-(hydroxymethyl)tetrahydro-2H-pyran-3,4,5-triol; (2S,3R,4R,5S,6R)-2-(4-chloro-2-(2-(cyclopentyloxy)ethoxy)-5-(4-ethylbenzyl)phenyl)-6-(hydroxymethyl)tetrahydro-2H-pyran-3,4,5-triol; (2S,3R, 4R,5S,6R)-2-(4-chloro-5-(4-ethoxybenzyl)-2-(2-(2-fluoroethoxy)ethyl)phenyl)-6-(hydroxymethyl)tetrahydro-2H-pyran-3,4,5-triol; (2S,3R,4R,5S,6R)-2-(2-(3-(but-2-ynyloxy)propyl)-4-chloro-5-(4-ethoxybenzyl)phenyl)-6-(hydroxymethyl)tetrahydro-2H-pyran-3,4,5-triol; (2S,3R, 4R,5S,6R)-2-(4-chloro-5-(4-ethylbenzyl)-2-(2-(trifluoromethoxy)ethoxy)phenyl)-6-(hydroxymethyl) tetrahydro-2H-pyran-3,4,5-triol; (2S,3R,4R,5S,6R)-2-(4-chloro-5-(4-ethylbenzyl)-2-(2-(2,2,2-trifluoroethoxy) ethoxy)phenyl)-6-(hydroxymethyl)tetrahydro-2H-pyran-3, 4,5-triol; (2S,3R,4R,5S,6R)-2-(2-((but-3-ynyloxy)methyl)-4-chloro-5-(4-ethylbenzyl)phenyl)-6-(hydroxymethyl)

tetrahydro-2H-pyran-3,4,5-triol; (2S,3R,4R,5S,6R)-2-(4-chloro-5-(4-ethylbenzyl)-2-((2-fluoroethoxy)methyl)phenyl)-6-(hydroxymethyl)tetrahydro-2H-pyran-3,4,5-triol; (2S,3R,4R,5S,6R)-2-(4-chloro-2-((2,2-difluoropropoxy)methyl)-5-(4-ethylbenzyl)phenyl)-6-(hydroxymethyl)tetrahydro-2H-pyran-3,4,5-triol; (2S,3R,4R,5S,6R)-2-(4-chloro-5-(4-ethoxybenzyl)-2-((prop-2-ynyloxy)methyl)phenyl)-6-(hydroxymethyl)tetrahydro-2H-pyran-3,4,5-triol; and ((2R,3S,4R,5R,6S)-6-(4-chloro-5-(4-ethoxybenzyl)-2-((prop-2-ynyloxy)methyl)phenyl)-3,4,5-trihydroxytetrahydro-2H-pyran-2-yl)methyl acetate; or a pharmaceutically acceptable salt thereof.

* * * * *

UNITED STATES PATENT AND TRADEMARK OFFICE
CERTIFICATE OF CORRECTION

PATENT NO.         : 7,838,498 B2                                    Page 1 of 1
APPLICATION NO.    : 12/060767
DATED              : November 23, 2010
INVENTOR(S)        : Chen et al.

It is certified that error appears in the above-identified patent and that said Letters Patent is hereby corrected as shown below:

In the Claims:

Claim 22, Column 81, Line 10: please delete "ofY" and insert --of Y--.

Claim 23, Column 81, Line 47: please delete "ofY" and insert --of Y--.

Claim 23, Column 81, Line 51: please delete "ofY" and insert --of Y--.

Signed and Sealed this
First Day of March, 2011

David J. Kappos
*Director of the United States Patent and Trademark Office*